US010221417B2

(12) United States Patent
Thum et al.

(10) Patent No.: US 10,221,417 B2
(45) Date of Patent: Mar. 5, 2019

(54) LNCRNAS FOR THERAPY AND DIAGNOSIS OF ANGIOGENESIS

(71) Applicant: Medizinische Hochschule Hannover, Hannover (DE)

(72) Inventors: Thomas Thum, Hannover (DE); Jan Fiedler, Hannover (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 0 days.

(21) Appl. No.: 15/305,919

(22) PCT Filed: Apr. 22, 2015

(86) PCT No.: PCT/EP2015/058709
§ 371 (c)(1),
(2) Date: Oct. 21, 2016

(87) PCT Pub. No.: WO2015/162172
PCT Pub. Date: Oct. 29, 2015

(65) Prior Publication Data
US 2017/0037405 A1    Feb. 9, 2017

(30) Foreign Application Priority Data

Apr. 22, 2014   (EP) .................................... 14165398

(51) Int. Cl.
*C12N 15/113* (2010.01)
*C12Q 1/6883* (2018.01)

(52) U.S. Cl.
CPC .......... *C12N 15/113* (2013.01); *C12Q 1/6883* (2013.01); *C12N 2310/113* (2013.01); *C12N 2310/14* (2013.01); *C12N 2310/20* (2017.05); *C12N 2320/30* (2013.01); *C12Q 2600/158* (2013.01); *C12Q 2600/178* (2013.01)

(58) Field of Classification Search
CPC . C12N 15/113; C12N 15/79; C12Q 2600/178
See application file for complete search history.

(56) References Cited

U.S. PATENT DOCUMENTS

| | | | | |
|---|---|---|---|---|
| 7,745,391 B2* | 6/2010 | Mintz | ...................... | G06F 19/24 514/19.3 |
| 8,178,503 B2* | 5/2012 | Rigoutsos | ............... | G06F 19/22 514/44 A |
| 8,188,060 B2* | 5/2012 | Khvorova | ............. | C12N 15/111 514/44 A |
| 2003/0124535 A1* | 7/2003 | McCarthy | ................ | C12Q 1/26 435/6.13 |
| 2004/0005560 A1* | 1/2004 | Isogai | .................... | C07K 14/47 435/6.16 |
| 2007/0134655 A1* | 6/2007 | Bentwich | ............. | C12N 15/113 435/6.1 |
| 2011/0178283 A1* | 7/2011 | Rigoutsos | ........... | G06F 19/22 536/24.5 |

OTHER PUBLICATIONS

NIH-MGC EST sequencing project, 603021392F1 NIH_MGC_114 *Homo Sapiens* cDNA clone Image:5192110 5-, mRNA sequence established Jan. 10, 2011, GenBank [online] Bethesda, MD USA: United States National Library of Medicine [retrieved on 17 (Year: 2011).*
International Search Report and Written Opinion for International Patent Application PCT/EP2015/058709 dated Oct. 23, 2015.
Yuan, Sheng-Xian et al., "Long Noncoding RNA Associated With Microvascular Invasion in Hepatocellular Carcinoma Promotes Angiogenesis and Serves as a Predictor for Hepatocellular Carcinoma Patients' Poor Recurrence-Free Survival After Hepatectomy," Hepatology, (2012) 56 (6):2231-2241.
Yuan, Sheng-Xian et al., "Long Noncoding RNA Associated With Microvascular Invasion in Hepatocellular Carcinoma Promotes Angiogenesis and Serves as a Predictor for Hepatocellular Carcinoma Patients' Poor Recurrence-Free Survival After Hepatectomy," Retrieved from URL:http://onlinelibrary.wiley.com/doi/10.1002/hep.25895/suppinfo [retrieved on Sep. 1, 2014].
Zhou, Yunli et al., "MEG3 Noncoding RNA: A Tumor Suppressor," Journal of Molecular Endocrinology, (2012) 48 (3): R45-R53.
Huang, Jin-Lan et al., "Characteristics of Long non-coding RNA and its Relation to Hepatocellular Carcinoma," Carcinogenesis, (2013) 35 (3):507-514.
Gutschner, Tony et al., "The Hallmarks of Cancer: A Long non-coding RNA Point of View," RNA Biology, (2012) 9(6):703-719.
Li, Keguo et al., "A noncoding antisense RNA in tie-1 Locus Regulates tie-1 Function in vivo," Blood, (2010) 115(1):133-139.
Leung, Amy et al., "Novel Long Noncoding RNAs are Regulated by Angiotensin II in Vascular Smooth Muscle Cells," Circulation Research, (2013) 113(3):266-278.
Michalik, Katharina et al., "Long noncoding RNA MALAT1 Regulates Endothelial Cell Function and Vessel Growth," Circulation Research, (2014) 114(9):1389-1397.
Michalik, Katharina et al., "Long noncoding RNA MALAT1 Regulates Endothelial Cell Function and Vessel Growth—Supplementary Methods," Retrieved from URL:http://circres.ahajournals.org/content/114/9/1389/suppl/DC1 [retrieved on Sep. 1, 2014].

(Continued)

*Primary Examiner* — Brian Whiteman
(74) *Attorney, Agent, or Firm* — Hunton Andrews Kurth LLP

(57) ABSTRACT

The present invention relates to a pharmaceutical composition comprising (i) a compound promoting the expression and/or the activity of one or more long non-coding RNAs (lncRNAs) selected from SEQ ID NOs 1 to 22, preferably selected from SEQ ID NOs 1 to 3; and/or (ii) a compound inhibiting the expression and/or the activity of one or more lncRNAs selected from SEQ ID NOs 23 to 42. The present invention also relates to a pharmaceutical composition comprising (i) a compound promoting the expression and/or the activity of one or more lncRNAs selected from SEQ ID NOs 23 to 42; and/or (ii) a compound inhibiting the expression and/or the activity of one or more long non-coding RNAs (lncRNAs) selected from SEQ ID NOs 1 to 22, preferably selected from SEQ ID NOs 1 to 3.

8 Claims, 14 Drawing Sheets
Specification includes a Sequence Listing.

(56) References Cited

OTHER PUBLICATIONS

Michalik, Katharina et al., "Long noncoding RNA MALAT1 Regulates Endothelial Cell Function and Vessel Growth," Retrieved from URL:http://circres.ahajournals.org/lookup/suppl/doi:10.1161/CIRCRESAHA.114.303265/-/DC1 [retrieved on Sep. 2, 2014] Published online before print.

Matouk, Imad et al., "The H19 non-coding RNA is Essential for Human Tumor Growth," PLOS One, (2007) 2(9) E845:1-15.

Matouk, Imad et al., "The Oncofetal H19 RNA connection: Hypoxia, p53 and Cancer," Biochimica et Biophysica Acta. Molecular Cell Research, (2010) 1803(4):443-451.

Yang, Fan et al., "Reciprocal Regulation of HIF-1[alpha] and LincRNA-p21 Modulates the Warburg Effect," Molecular Cell, (2013) 53(1):88-100.

Yang, Fan et al., "Reciprocal Regulation of HIF-1[alpha] and LincRNA-p21 Modulates the Warburg Effect—Supplemental Information," (2013) Retrieved from URL:http://sciencedirect.com/science/article/pii/S1097276513008290 [retrieved on Sep. 3, 2014].

* cited by examiner

LINC00323 (lnc-DSCAM-1) transcripts

LINC00323-001 (lnc-DSCAM-1:1), 2088 bp
LINC00323-002 (lnc-DSCAM-1:3), 349 bp
LINC00323-003 (lnc-DSCAM-1:2), 580 bp Exon

A

Figure 2:
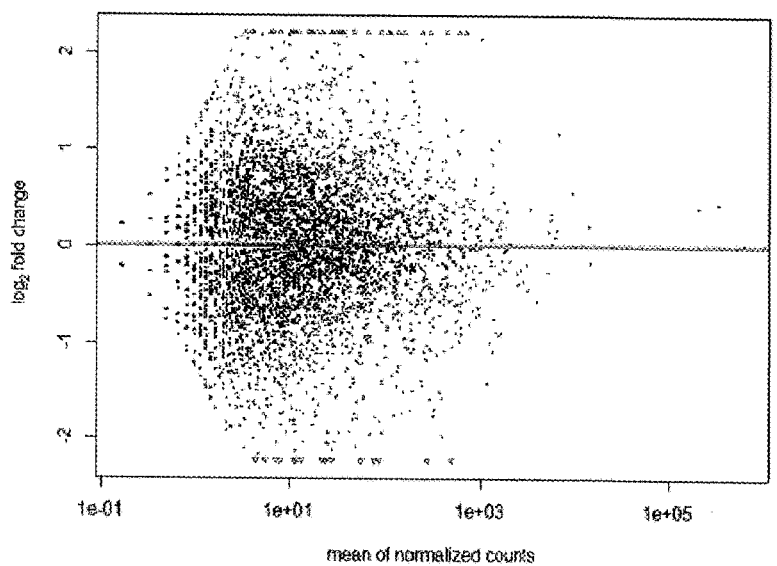

Figure 2 - continued
B
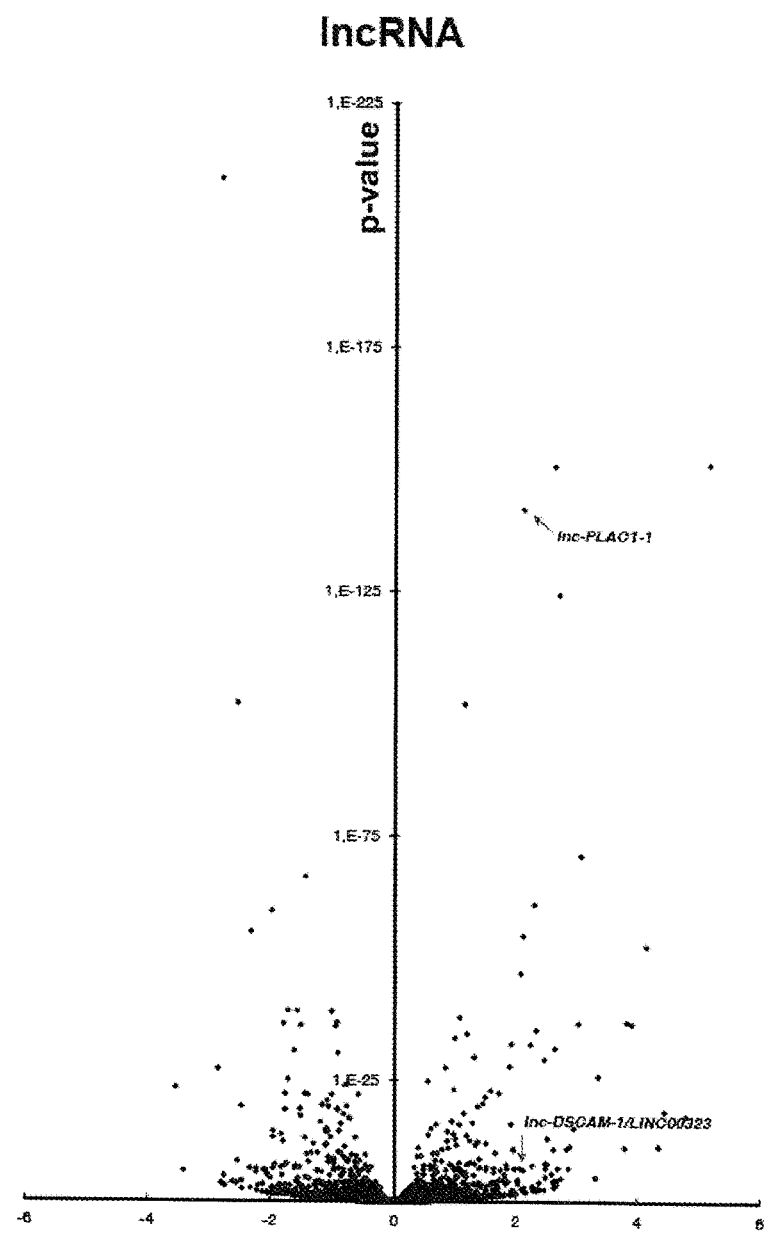

Figure 3:
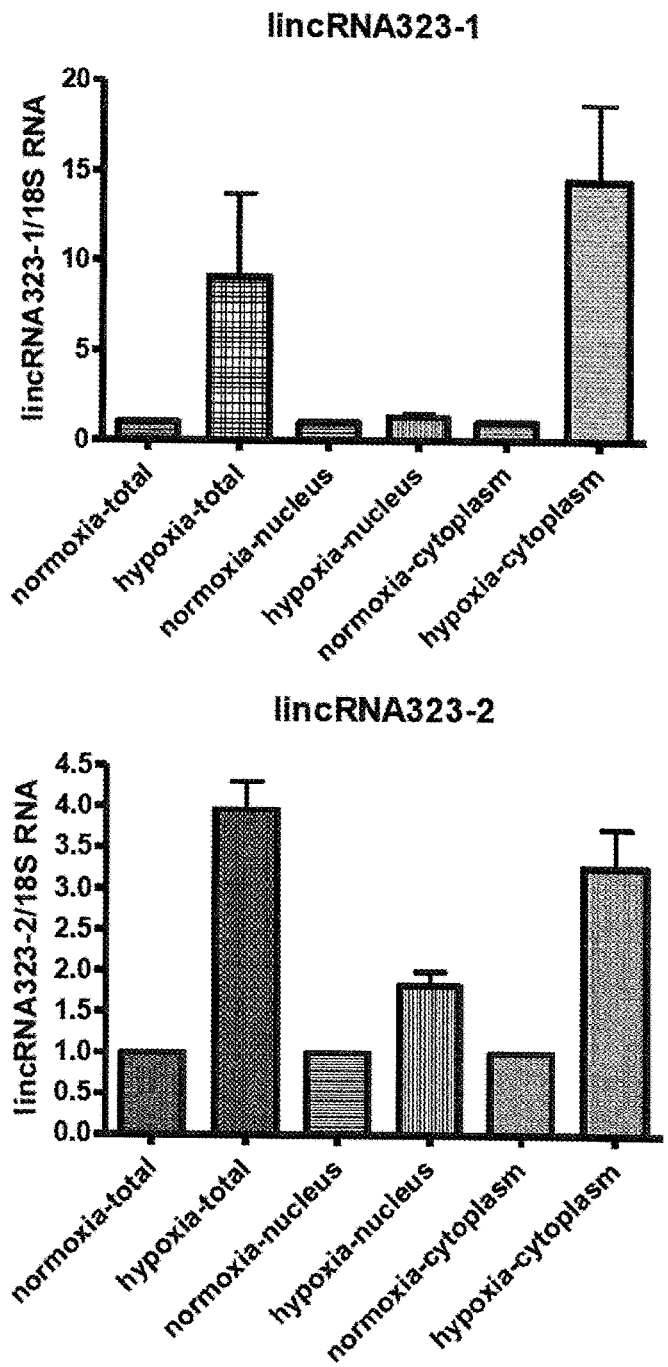

Figure 3-continued
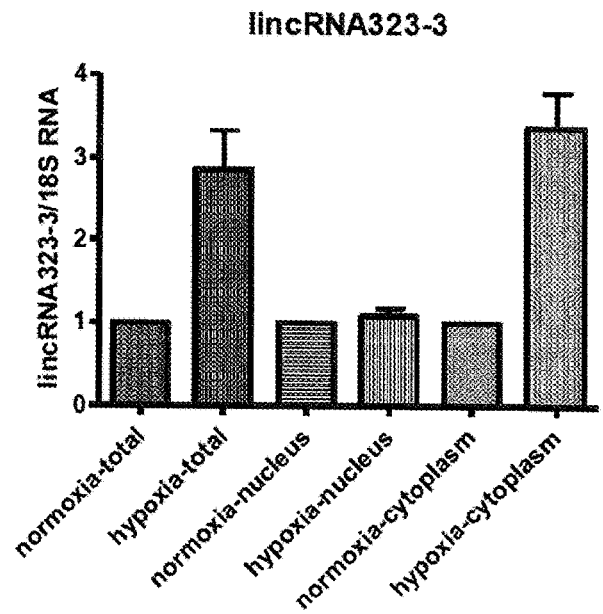
Figure 4
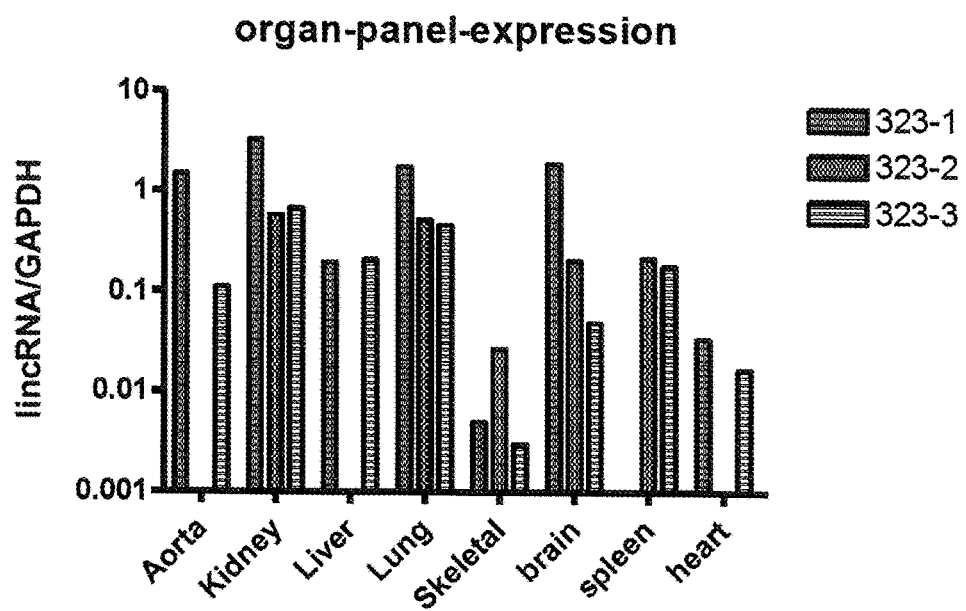

Figure 6:
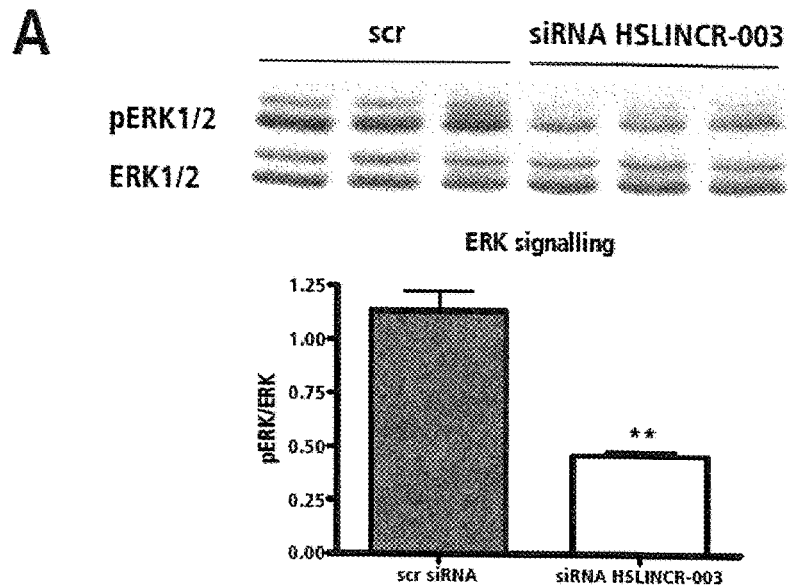

Figure 6 – continued
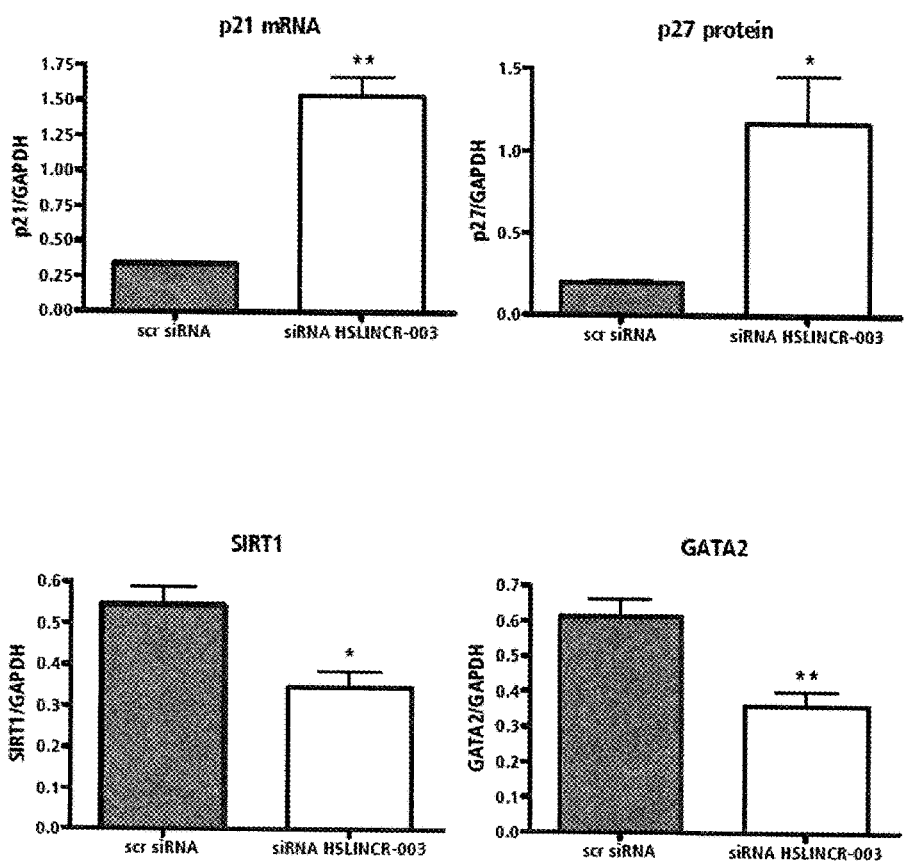
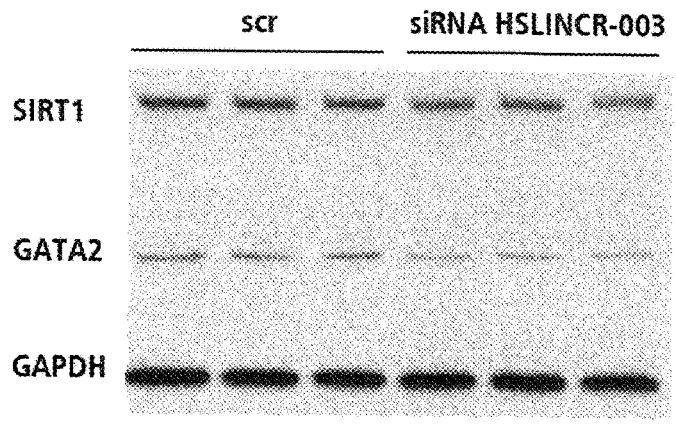

A

B

Figure 12:
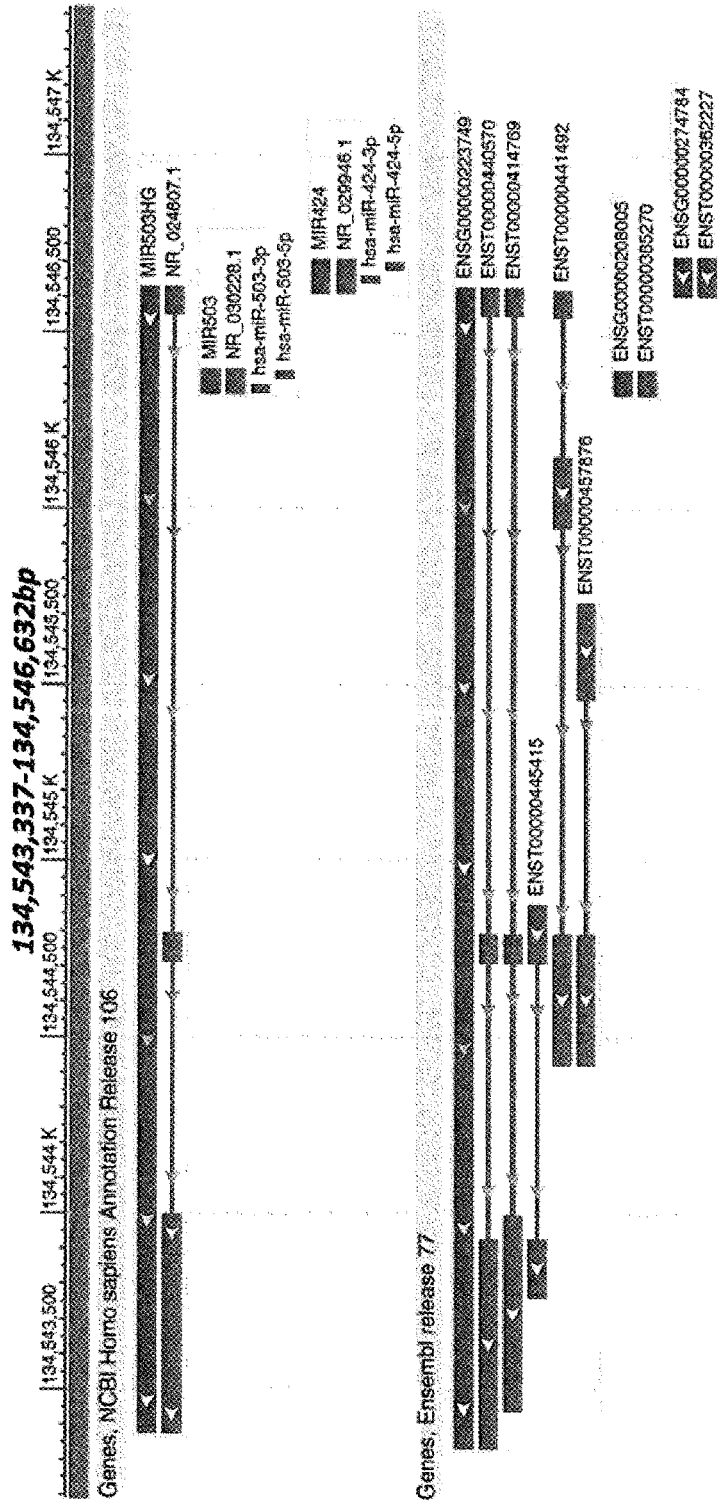

Figure 12 – continued
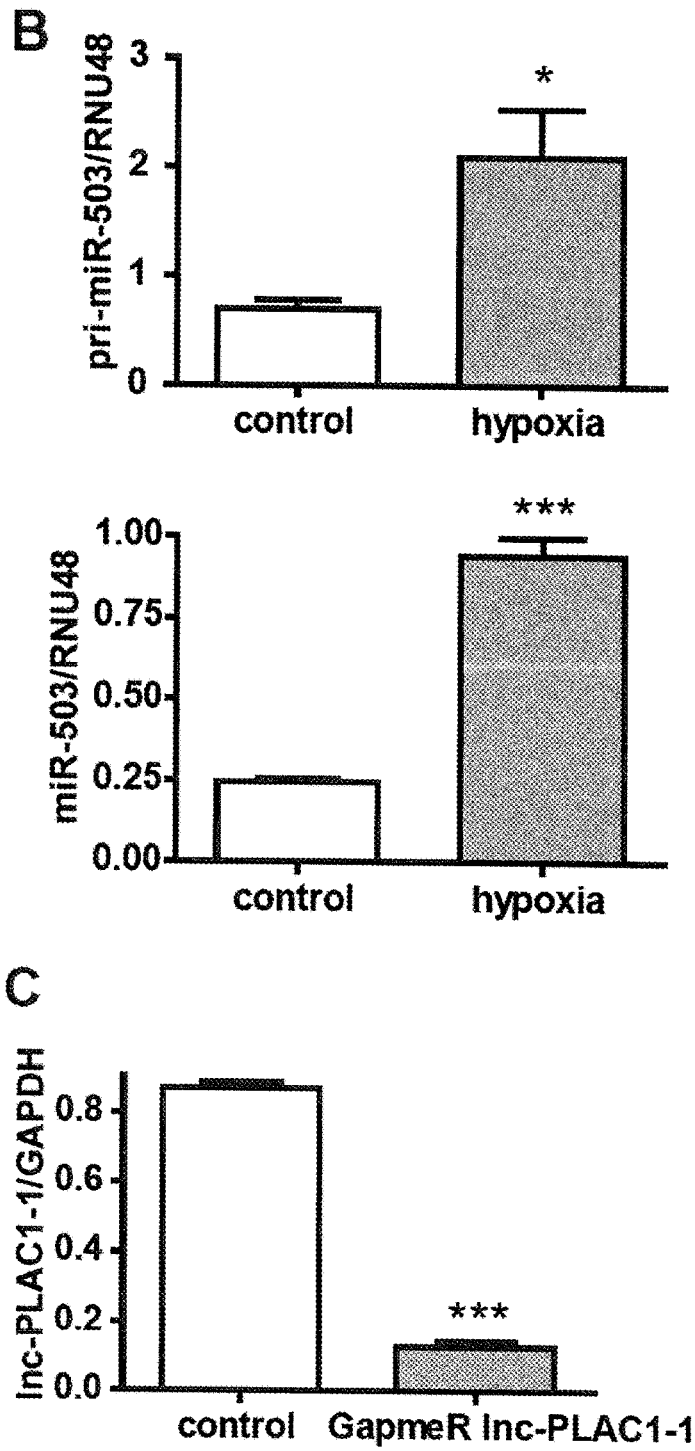

Figure 12 – continued
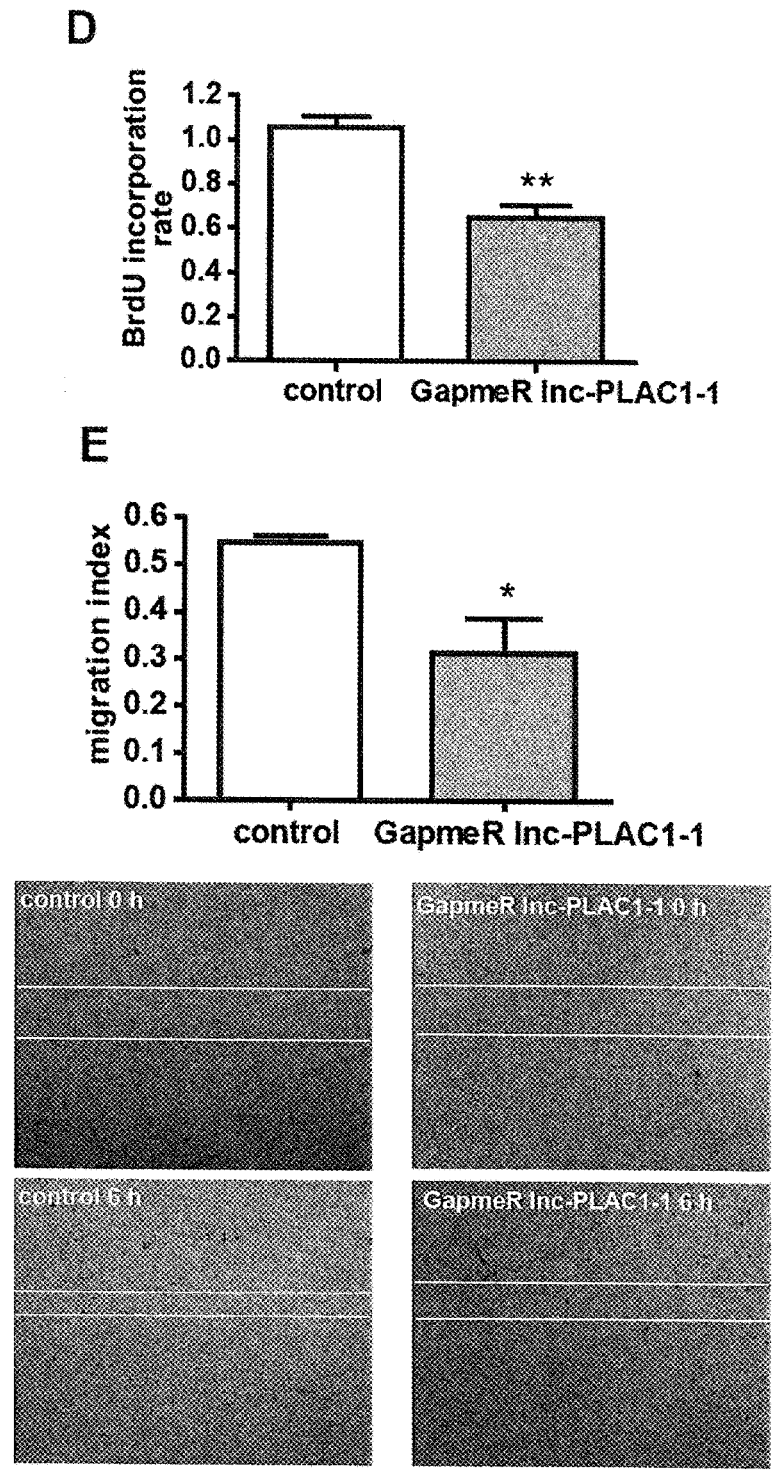

Figure 12 – continued
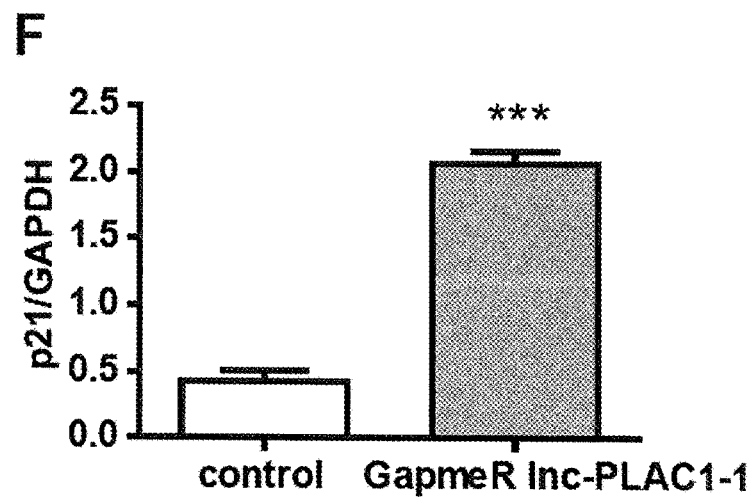
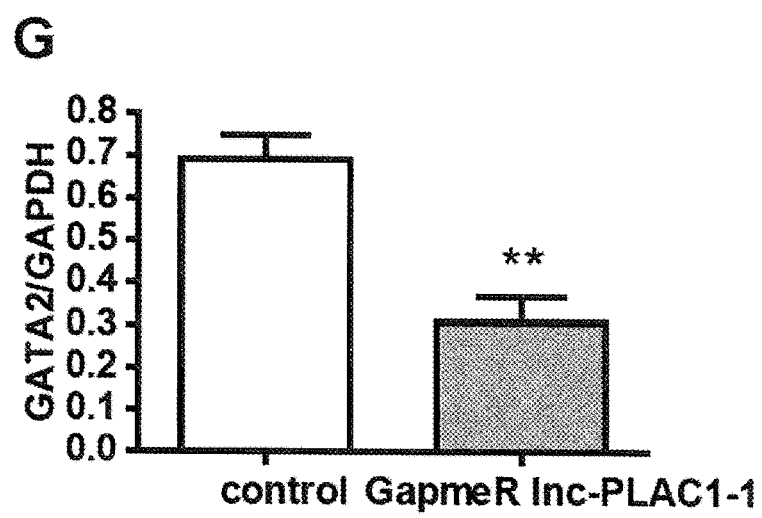
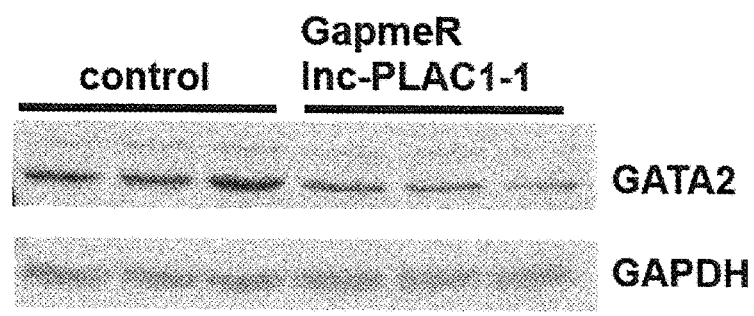

Figure 12 – continued
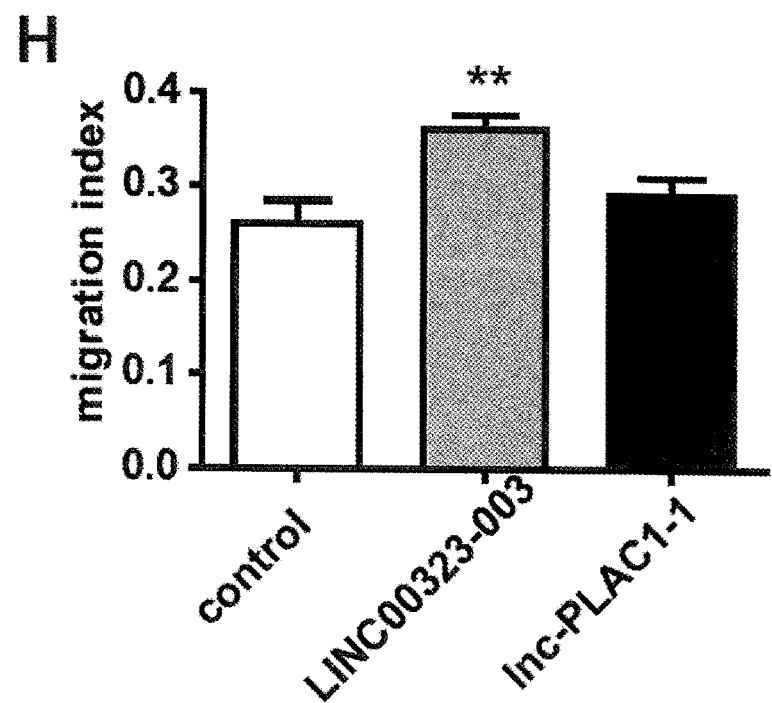

SEQUENCE LISTING

<160> NUMBER OF SEQ ID NOS: 52

<210> SEQ ID NO 1
<211> LENGTH: 580
<212> TYPE: DNA
<213> ORGANISM: Homo sapiens
<220> FEATURE:
<223> OTHER INFORMATION: lnc-DSCAM-1 isoform 3

<400> SEQUENCE: 1

```
aagtagtcga gctgaaaccc ctgaaaacaa tcgtaggacg atgacaaggt tttggcagct     60
gcaatcttaa agaccaggaa gtgagggtaa cagaagcaaa tcatcagtgc ctgtctttga    120
acttgatgaa actgtctcag cctcatgacc tgtggtacta gacagagacc acaacacctt    180
gtctatccag agtgtgggag cactgtgtgc agttagctcc tggaggcttg tcctcagtag    240
gcttagggca tgaggagccc tggaaagccc aggaccccat ggagggccct ggagaaacag    300
cacctgtggc tgagggggttc acaggcccag cgagatccac tcaggtgagg tcacctgtag    360
aggtcatgct gcggagtccc gagtccctga ttatattcaa gacgtggagc tctctttttc    420
ccgtcctgct ttctttccag aagtgcctca gatgcatcct cccttctct tttctccaca    480
tgaagacgtc actgaccatc ttctctggtt tgctttccaa caccgagcac caagtgcttc    540
aaaggtcatg gtgccctggg gccgagagct acttatgtgg                          580
```

<210> SEQ ID NO 2
<211> LENGTH: 349
<212> TYPE: DNA
<213> ORGANISM: Homo sapiens
<220> FEATURE:
<223> OTHER INFORMATION: lnc-DSCAM-1 isoform 2

<400> SEQUENCE: 2

```
gctgaaaccc ctgaaaacaa tcgtaggacg atgacaaggt tttggcagct gcaatcttaa     60
agaccaggaa gtgaggtgag gtcacctgta gaggtcatgc tgcggagtcc cgagtccctg    120
attatattca agacgtggag ctctctttt cccgtcctgc tttctttcca gaagtgcctc    180
agatgcatcc tccccttctc ttttctccac atgaagacgt cactgaccat cttctctggt    240
ttgctttcca acaccgagca caagtgcttc aaaggtcat ggtgccctgg ggccgagagc    300
tacttatgtg ggcatttata accaaataaa tattgaaatg cccacaaa                 349
```

<210> SEQ ID NO 3
<211> LENGTH: 2088
<212> TYPE: DNA
<213> ORGANISM: Homo sapiens
<220> FEATURE:
<223> OTHER INFORMATION: lnc-DSCAM-1 isoform 1

<400> SEQUENCE: 3

```
tttcaaggaa caacagagag atggtatttc cagacaaggg aataaattcc cggaagcaac     60
tggccaagga tgaaaatcc tggagaacag agtggaagaa acgcgtattc cacatttcct    120
gttgattttc tttcctccct aaacactgac ctcccgcagt cttcactagc aggtgaggtc    180
acctgtagag gtcatgctgc ggagtcccga gtccctgatt atattcaaga cgtggagctc    240
tctttttccc gtcctgcttt ctttccagaa gtgcctcaga tgcatcctcc ccttctcttt    300
tctccacatg aagacgtcac tgaccatctt ctctggtttg ctttccaaca ccgagcacca    360
agtgcttcaa aggtcatggt gccctggggc cgagagctac ttatgtgggc atttataacc    420
aaataaatat tgaaatggcc cacaaagcaa atgttagtgg taaccaacag cggtaaaact    480
```

-continued

```
gggtacatgg gaccctgaac cttcttgaat attccccatg agaccctggg ccgaccttcg      540
ggctttccag tgtgctcaga aaatcctccg tggctcccag ccccagctta gtctttcaac      600
ggtcctcgga ctgaagcaag agacaggaa ggaattgtcc aaggttttcc agcatgctga       660
gaacacttac catggtggag cctggcacgt actggctctt tgatgcatgt gtattggtct      720
caagtagcca gaagcatctc ctctgagagc ccttgccctc cagtttaaat ggcaaatgga      780
agggaatggg ttctggaagg ccccaggtgg gctggggtgg gttctggaga ccatcttcca      840
actcctgttc aggaggaggg ttggtcagat cagctctgtg ccacctggg ctctggaggg       900 gcgagatacg gcaggtgcg gccacaggag ggagagcacc atgtgcgggg aagcccaca        960 gctggaacca aaggcccca ggagggatcc tggctctgac atctcccagc cgtgtggcct       1020
tgggcaaggt ccctgacttg gacctcagcc tcctcatctg taaaacaggc agaacagtaa      1080
taccgacctt gtaggttgta tagagttcat atacatcaag cacttaccac agtgcctggc      1140
ggaccgcatg ccctaaacac acaatccgtg aaatgaatcc atcagcaagc agctgctagg      1200
ggcagtgtgg ggcagagagg cagctgcctg ctggaactgg ctgacaggag gatgagtgtg      1260
tggcaggagg aacgctctgc acagaggaca ctaggtagcg tcacctgtct cttaccctgt      1320
gtctccactg gaatggaatg tcagactcgc accatgcatt cctttccctg ccaaaacgcc      1380
tcctcttagc agtgagcaag aaagttgttc gagtggatga agccaaaagc ccatttggca      1440
agagtgctgt tttggaaaat gcttagcggt gtgggttggg atgaggtttt ctgtgccttt      1500
ccattatttc ttcagcttca tgtaaccctg actgagcaat gctcagcaga gtgaaggctg      1560
ggcagcagat ggacaagatt ttctcaaact cctttttaag ccaatttcaa aatagagaga      1620
gggaaaaatc cttgttttct cttttcggtt ttgagaggtt tcatatgcag acacaatttt      1680 aaatttatt ttttttgccc ccaatgagat gttttggagat ggtggtacta aacaggaag      1740 gaatttataa gtattgggga attttttcatc ccaattccca tatcctccta taattcaagg     1800
agtgaatggg tagtgttttt gttttttgtga gaggggtggc ggagggtaga gagagaaaga    1860
gagagagaca gagagagatt acatagaggt gtccaaaatg aacacagtaa aaaccagttt     1920
tgattaattc tgcaatatta agtaggcagc caaaaatttt ggtctgctta attcttagct     1980
catctaagtc tccagttgac tgattgattg attgaatgac ttattcaaca tgcgctagcc     2040
agacactggt ctagggccca ggaattcagc aataaatgaa acaagacc                   2088
```

<210> SEQ ID NO 4
<211> LENGTH: 1657
<212> TYPE: DNA
<213> ORGANISM: Homo sapiens
<220> FEATURE:
<223> OTHER INFORMATION: lnc-PLOD2-2

<400> SEQUENCE: 4

```
aacttgttct gttttcaac aaacaatata cttatttgca attaaatgaa aataaagcat       60
tgaattctga agtttagag aatgaccta gagatttta gtggttgtca gccttagcct        120
cctattaaaa tcatctggga actattaaaa gcatttaatg ttgtgaccct acctagacct     180
attaaattcc attctctggg gtgaagccag gccatcagtt attttaaaag ttctccaagt     240
gcttctaatg tgcagcacag gttgggagaa tctgatctag cttagcactt aaaggttata    300
gtgctaccac tacataacac ttctatattg agtttactgt agtatattaa tggagctatc    360
ttaagtggaa aatgtctgat caatcattaa atagcaatct aagtgaaatc tataactaaa    420
```

```
atttctatct ggaaagacaa aaagaaaaac caacttctct ttgagggtat gctatacccca    480 gagacttggc tagtgctaag gagggcatgg tagacttccc gaggtcacac aaagaacaag    540
cagctcatgc ttggttctac ccaatagtct gagtcccctc agtcactctg ttttagcctc    600
taaaccacta ggacgtgatt tgagaaattt catgaagcct caaggtgttc tttcaggtta    660
tttgtacaat ggggaagaaa atatctatag ttcaacctct ttcccatact catgacagat    720
cacctggcct gtgcttcagt attttacaga ttgttcatct gtggctgaaa agctcttatc    780
aaaatgctct tactttttatt gagctgataa agttgccatc ctaacttcta tccattggtt    840
ctggctctgc ctcctggagg aacacagact atgttgattg tcttttccct gtgttagcaa    900
tgcagatgga ttgtaatttt cctaaatctg ctcttcaaga aaagatttca agttttgaaa    960
accatatcat catcctgtcc tcggtgacac ctgtttctct cctttgtcaa catcaccttt   1020
cacaatgtgt cacctggata gcagatcgaa caacctggct ataatagtgg ttctgatagc   1080
ctcctttgat ctcgtcattg tattctagaa atgaagccca agattttatg tattttacc    1140 gcggtcatac cacgttgatt taaaagatca atgattttca agccaggctg acattaaaa    1200 tcacttggga gagctttgaa aaatatagc gatatcctgt tttacccttg atcaattaaa    1260
tcagaatctc tggggataag gcccaggtac agtgattttt aaaagtactt caatgaccct    1320
aatatgcatc taagtgagtt ctatccttaa atgtggtttc tctcaatttg taggtaaata    1380
caatattttg ttgttgtttg aatgtaaata tcaggcttttt gatctgttct agtttaatttt   1440 tctgataata gtagtcccag aattttcaaa tgcaattctt taagattgca atgaagttag    1500
aactcttacg ttactgttta tgtccacaaa atgtttagaa aagtttgaaa aggatttttga    1560 aaaagattaa cagtgttaat atttcttata ttgttgggtt tatgcataat ataatttggt    1620
taatatgtat cataaataaa agtattttaa gatcaca                             1657

<210> SEQ ID NO 5
<211> LENGTH: 1662
<212> TYPE: DNA
<213> ORGANISM: Homo sapiens
<220> FEATURE:
<223> OTHER INFORMATION: lnc-PTTG1-1

<400> SEQUENCE: 5
cactttaatg aagcttgaga cacatggcat tgccatgcaa tgattttttcc cccctcttca    60 cgggatcaga gggaactaat agaatgtgac aatgattctt tagcagggac tgctgaggct    120
tctggttcct ttttaagatc tgcagtgaaa gaagatgaga acatggata tgcccttctt      180 ttggtccccc tcttcctttta tttgatctct acttccttct ataaatatat tagggctaca    240
ttgtcccttt gtatttcaaa caaggcaaaa agaggttgta attacacttt actgcaatcc    300
tcagtttctc cagggaacag gaatgcaaag gctttgaagg cctctctatt tgctgacatg    360
gtcagctggg tgccatgggc caagtccttc tgttgccctc ctctgtcacc aagtaagcta    420
ggtcctttct gaggctcagg tttgctgtga tgatgatcac ttttaggcag aaggttagag    480
gcctcatgag tgctatatgg actttattag gctttagatt tgatggggaa taagggatgt    540
gatttgtctt ttgggaactc atctttgatt catcattgtc tcttggtatc ttggaatttc    600
catgtcatta cagtctacag aatgaaagag taacctgtcc cagaggagag gcaggtgaaa    660
gactccacag catgctcatt ctcattctgt cttctcagtg acaccgaggt ttactgagtg    720
cccactatgt gccaagcact gtgctcaggg cttttctttgt atgcatgatc tcagtgaatc    780
tcaccaagcc tcatctggaa aacggggaca aattaacaac aggatggcaa attgaaaaac    840
```

| | |
|---|---|
| acgtaaccat gttctacaga tggaaagggg tgcttggtta ttatgaaggc cccctcgcaa | 900 |
| gcgtgtggga catgggtgtg ttctctgggt tgtactgatc agatcaagga cctcccccac | 960 |
| ccttctcaca ctctgcccac ttccgcccct tgcttatcag acccttagcc agtgactcat | 1020 |
| tccagaacca gaaccttggt gaaatctcaa ccgacaccag atcggtgt cttcagtcct | 1080 |
| agactgatgg agaaaatcca gaatatatac tagaagctcc aaatgctctg ggtttcagct | 1140 |
| cctctgtgct gtggacactg actttggctc agaactccga tttagtacaa aaggctcatt | 1200 |
| tttatttcag gggcactctt cctaaagcaa acctaataaa tgaaatatgg aattcacaga | 1260 |
| tacacacaca cattaaaaaa ttaacctagt gtatctgtga ggagtaggca gaaattcact | 1320 |
| gtataaaaga atgcttcatt tcatagagaa tttgtgttaa gattccatta gatagtacat | 1380 |
| ttctcaaaga ttttgaggt tgtatttgct ttaccaaaac ttggtttatg taagtggaaa | 1440 |
| aagcatgttg caaaataact tggtgtctat gattcagttt atgtaaaata ataaatgtat | 1500 |
| gtaggaatac gtgtgttgaa agatgtacat caatttgcta acaatggtta tctctgacgt | 1560 |
| ggtgggattt gagatgtgtt tttctttttg gttgtatttt tctctattgt ttgacttaac | 1620 |
| acagaacatg tttggttaca acaataaagt tattgaagac aa | 1662 |

<210> SEQ ID NO 6
<211> LENGTH: 1736
<212> TYPE: DNA
<213> ORGANISM: Homo sapiens
<220> FEATURE:
<223> OTHER INFORMATION: lnc-AC021860

<400> SEQUENCE: 6

| | |
|---|---|
| gctatgtgtg tccggaattg gtgggttctt ggtctcactg acttcaagaa tgaagctgcg | 60 |
| gaccctcgcg gaccgtgtgt gaatgcctgc tctgtgagcc ctcagaatct actggctgaa | 120 |
| tgagtgcgtg gaggaaatgt gctcagagct gctgtgtgtc atcctgtgtt tgaagtgctc | 180 |
| ctgcagctat cattcatcca gttaagaatt tgaagaagtg tgtgcacaaa gacggagtct | 240 |
| cactctgttg cccaggctgg agtgcagtgg cacaatctcg gctcactgca acctctacct | 300 |
| cctggattca agcggttttc ctgcctcagc ctccagagta acaggggatta caggcatact | 360 |
| ccaccttgcc ctgctgattt tgtattttta gtagagacaa gagtttcacc atgttggcca | 420 |
| ggctggtctt gaactcctga cctcaagtga tccactgcct cagcctccca agtgctggg | 480 |
| attataggcg tgagccactg cgcctggcca aatgctctac ttttaatca atgttttcca | 540 |
| aaatagggat ttttgctatg tgctttagaa attagagaac aaacggtgat aatatatgct | 600 |
| aaacttaaaa ttagtatgcc tccttttata gacaacaaga actttgtcac ttcccagttt | 660 |
| gtcttgtcat tcaggaggct cagagctacg atctgtgccc actcgtgctg cctcttctta | 720 |
| actttgatt cctgaagcag cgatttcatc tccgtttccc ctcatcacct gttcttttaa | 780 |
| ctgtttaaaa acagcattac atgttgttgc aagtggcctc aaattctttt ggtagaagg | 840 |
| gaaattgtaa tccatgagaa gaaaaaaatt ttcctaacta ttctcaggtg tgtttaaggg | 900 |
| ctgcattcca tgatgctatc agtgccttct ttcagctcac aggatatcgg ccatgttaat | 960 |
| gagtctgatg ttgctagtat cacaggcacc ggaaaatatg cacattatgc tggagcatta | 1020 |
| gaatgcaaca gaaagagccc tgggcttgga gtatgcagaa ctggttcttg ttacaactcc | 1080 |
| tcttactagt gggctctgga agaaaacaca ttgaattcat gatcatggtt aacctttgga | 1140 |
| gagagagagg agaccaggat gaaggagcca gtcgaagatc ctgttcaagt gtacactgag | 1200 |

| | |
|---|---|
| ccagcaggtt caccagaaag ctattgagcg tttgctggaa cacattatgc agggtgaatt | 1260 |
| tcttctggaa tgttgccaag gattttttat gcttctgtgg caggcatttc ttgaacattg | 1320 |
| tcatttagcc aagcaaagaa gattttctta aaggatagaa aatgtttaaa aattttttgtt | 1380 |
| tgtttgaaga taggttaaat ggctatatga tctcaggata agacagagaa aatcacttat | 1440 |
| ttctctaagt gatctgatta ggttagtgat gttttgcctt taaacagatt catcattatt | 1500 |
| cctaaagtat tgctgtatta atactgtctt ctagaaagta tccaccagtg cctactttc | 1560 |
| ttcgatatca ttagctgttt ttcgaaactg aatttgctct tcagagattt ctcatatgtt | 1620 |
| tgcgtataag gaactactgg taatagccaa gaaaatttgg aggtgcagag aacatgctga | 1680 |
| aacagaattt ttcactttca attctagaac tatgccataa aaaaaagga aaatgt | 1736 |

<210> SEQ ID NO 7
<211> LENGTH: 381
<212> TYPE: DNA
<213> ORGANISM: Homo sapiens
<220> FEATURE:
<223> OTHER INFORMATION: lnc-JAK1-1

<400> SEQUENCE: 7

| | |
|---|---|
| atgtgaagag gtagcaagag agcagcaatc tacaagccaa ggaaagaggc cacagaggaa | 60 |
| accaaccctg ccagcatctt gatcttggac ttccagcttc cagaactaac cagggacccc | 120 |
| actcccatgc cgacagtatg ggctgctgtc ttcaggacca ttgcaagtgt ccttcacggt | 180 |
| tcggttcaca tttcacaagc cccatgaagt ctatctggat tttcgatgga tgtcttgcct | 240 |
| tttcctctac acactacagg aagagtggcc acccctgcca agggcctagt atagtaccct | 300 |
| atacatgtag ctgatcagtt gattgttact gatcatatgt atcctgcatc atgttataaa | 360 |
| aaattaacac agtgcttggc a | 381 |

<210> SEQ ID NO 8
<211> LENGTH: 1894
<212> TYPE: DNA
<213> ORGANISM: Homo sapiens
<220> FEATURE:
<223> OTHER INFORMATION: lnc-ACER2-1

<400> SEQUENCE: 8

| | |
|---|---|
| gtggaatgga gtatatttga ggaggacaaa acataaacttc acttttgaac agaaatcact | 60 |
| ctagcttgcc agcatgggat gtaaaccaag agagtagaaa tatacccatc ttattttaag | 120 |
| ttgggtttat ggcatcgctc atatatgtaa aagcactaca aactctttaa agaaaattgg | 180 |
| gaaactacag agaagtcaaa gaaaaaaaaa agtaacccat atttctattg cccaggtata | 240 |
| atccttgtta atattttggt ttggtctcct ctttttttccc ccaatatagt tgtaaataaa | 300 |
| tgatgtctttt cagagttgac atttatcctg tagcttgaat ggcatgtaaa tgccagttgt | 360 |
| atatttttc atgaagtgta ggtttggaat acactagagt tagctatatg cttgaatgct | 420 |
| gatcactgga ttctgagact gactactgag tctacccttt taatcaagcc taacatgaat | 480 |
| gggctccaaa aagtaatgaa tgtaattgta cttttttgatg tgcctctgca cttggcttgg | 540 |
| tgagtcatca taaatagctg ttaaatatgt gactttacag attttgatat gttcagattg | 600 |
| taaaaaatga atagtttatt tcattaattg atgggcagtc aagaatctcc ctcccttcag | 660 |
| tagggctgac acttaggagt taggtcatgg ttgtggttac ttggcatggc taatcagatt | 720 |
| ttgttctggt cagaatttgc ccaagatcaa tacccagcag aaactggagt taggctataa | 780 |
| aaaaccattc atgtttccga gtgatcattt cagtcagcga ttcatgttt acagtgttta | 840 |

```
gttgttgatt attagaaaaa gtaatatttt cttcccttta tgattacatc attataaatc      900
aagtccttcc atgaacacat ttaaggtgtg tggagatgag atctctgaat ccatttgggg      960
atgggctgca tttttgggga actctatgcc tgtccagtga agagtgccta aaacattaat     1020
tatagatcaa agatgttctg ttgagggaca aagcttgatg gtcatcaaac acaaggcttt     1080
gtaaaaatac gaccacctat tccacttact ggatctgtca ggtgtgtaaa acttctctcg     1140
ccagttcatc atgcttccat gagccctcag gactgggatt tgagccttcc tggctcttta     1200
tcccttgggg cagacatgga accatctctg agggaccagg tggatgctga agctcaccca     1260
gtcagggccc ctctcctagc tccttttaca ctgaaattaa tctgaaagct ttcatagcca     1320
aggctttgcc taggtgctat tattccagct ggccaaagag aagtcttggg ccagattggg     1380
attctcaatg gatttatag acataattcc cctgcaaact taaaaaaata aataacccct      1440
actttatagg actaattgtt tgaattgtat cttctctgt atgttaaacc agatttaaaa       1500
ctattttata accacaatat gtaatcagag caatatagtg ttttcagata tataccttgt     1560 tttataccctt atgtaggtgt cctacataag ggtggcatgc ccactggctg tggtaaaatt    1620
taatcctcat tgctttggga gtgacttaag gccttttgaa gtggagcttt tgcactttat     1680 acttttctg tgaactatga taactatatt tgatattaaa gctgtaagtg gcatttttcag    1740 caaatgaata tgtacatgtt tgtgtctatt tccaaaatga tttctgaact atctgcagtg    1800
aaaatgtatc tgatggattg tagagcaaag cacattgcct aaattcattt gttaatgaat    1860
tgggtaccat tgttattaaa aatgcgtaaa gtaa                                 1894

<210> SEQ ID NO 9
<211> LENGTH: 714
<212> TYPE: DNA
<213> ORGANISM: Homo sapiens
<220> FEATURE:
<223> OTHER INFORMATION: lnc-BLCAP-1

<400> SEQUENCE: 9
tcaagaactc atcttgcagc atggaggaat cgtgatgatg gctgcagccc ccagaaggtg       60
aacttggcag gagctggctg agatgatttt tctgctgatg gtgaaatgtg ctggcagagt      120
ctatacagcc acttttaggt gatatattac gttctggtga aagcattctt cctaatacaa      180
gctgagagct tacagctagg agacaacctc caggagcaga gatcacacac tctcgggcag      240
aaaaacagct tctgtattct tccctgttta ccattctggc atcaatttca agtgctcagt      300
ccctcaagct ctttcctctt tacaaaagcc cggctactgc aacaaagcat cctgtctgct      360
gtaagtttca agagactctt tgaaactact gaccatcttt ctcactgcat tcatgctgca      420 acacccaaa tcctgcaaag ctctgactga atcaggaaaa agtgaccttg gtagctagtc       480
tccaaagatg gccaccacca atacttgcct tcctgcgata tatatcatac tccttgtatc     540
aggaagagaa gtgtaattcc ctcccccatga atctaggctg gccttagtga ctttcttggc    600
caatagaata tagcagaagg cacattctgg gatttgtaag actaggtcgc aggaagcctt     660
atggcctctg ccaggcctct tgcaatgctt ggccttggaa cactccctcc taca            714

<210> SEQ ID NO 10
<211> LENGTH: 1681
<212> TYPE: DNA
<213> ORGANISM: Homo sapiens
<220> FEATURE:
<223> OTHER INFORMATION: lnc-ARRDC3-1
```

<400> SEQUENCE: 10

```
ctagagagaa ggcaccttca ggtttggctg atgaatcctg tatctctgcc ttgtctccag    60
gcccccaggt tctgcctctg tcctgacatc cagtgttgga ttcctcttca catcaactcc   120
tctctgtagg ttgggccatc agaccctacc tccttattta tgttgagcaa aggagagaga   180
atgcctctac aaacaatgaa aaagtgaaa aaaaaaatct ttctcctcct tataacttta   240
gttagcttaa ctttagtcag ttgcttagct actaaacagt agctattggg aggtgggaag   300
gaatactatt gtgtaatcaa ctaaggctca tacagaggat tagggttatc tgaattgatt   360
tgaattaatt agaatttact ctcagagctg tggcaattcc ttgaaccaca ctgattgcta   420
taaagtggaa gaggaataga ttgaattttg gggagtcaac tacaatgtgt actacaggaa   480
caaaacccat cagaagatgt cagaagataa ggattttgt cctgatgcta cacttaccag    540
ctgtccctca gtgttctact tcttaaaaaa agagagatgg ataaacagag gcaacccgag   600
gataaaggcc ttgctcagtg tcacacattt cagtcactaa ataagacaca atggatgcca   660
gtattctcat cccctcacaa ataaagagcc ttcaagctct tgcagtcaac aagaactttt   720
ggaatgattt cactgcctga aaaggcagat acataggtga cacccacaaa taggaagaaa   780
atcaacctga acctgagtgt gtgggctcac tgactctaag cagtagagac agaagaaaaa   840
gttttagcaa agaagggttc tgaaagaaaa taaatatagc tcgttatcaa gtgctgtttt   900
tacacagtaa aacatgggca aaattactct tctttaagta gtaattctta tctcttgatt   960
aagtcaccta ctcattcatt taataaatac atactgattg ttttctatgt gttgagcact  1020
catctctgta ttgaaaatat aataatgacc aaagttgaca atagtaataa caataatagc  1080
taatatagca ggcactaata attatttgtt gagtaatatg tcaaaattca gtgtgaacag  1140
cattctattt ggggctgcat ccactgacta taacacagct aatctatctg aaatgttcca  1200
gctttgggcc tctctaacag aagaagctgt tgttgggcct gcctctagtt ggcgatgcat  1260
ccaccaatga gaatgaattt atgatcgacc actcttcctg taaaggccgc tggaactgac  1320
agcattgtga ttttctttta ctgttagttt taaattacta gaaccaactc aattactaga  1380
acgaacttta cttctttgtt tcctacttat caaaacagta aaaacaacaa gtaaaagaaa  1440
tgccatctta atattgtttt gatgacaaaa cagtattcct tttagttgtg cttcaaatgg  1500
aataagatgc aaacaggctt ggtatggtgg ctcaccccctg taatcccagc cctttgggag  1560
gccaaggtgg aaggattgct tgaggccatg agtttgagac cagcctgcgc aacatagcaa  1620
gaccgtgtct ctacaaaaaa taaaaaatta gctgagtgta gtggtgtgtg cttgtggtcc  1680
c                                                                  1681
```

<210> SEQ ID NO 11
<211> LENGTH: 2109
<212> TYPE: DNA
<213> ORGANISM: Homo sapiens
<220> FEATURE:
<223> OTHER INFORMATION: lnc-ATXN7-8

<400> SEQUENCE: 11

```
tatacacata tatatacata tatatatata taaaaaatag ccttttttaga tggatgtctt    60
tcccatagca atatgcattg aactttcctc catgactttg tgtggctcaa tagttcattt   120
atttttgttg ctgaatagct tctgcttaat tttcaaagtg tttaatgtaa gaaagcggta   180
tagtccaggc gcagtggctc aacacctgta gtcccagcac tctgggaggc ggaggcggtg   240
gatcacttga gcccaggagt ttgagaccag cctgggtaac atgataaaac cttgtctcca   300
```

```
taaaaaatac aaaaattagc tggaaatggt agtgtgcgct tgtagtccca gctactcagg    360
aggctgtggt gggaggattg cttaagccca ggagctagag cctatagtga gccatgattg    420
tgccaccgca ctccagcatg ggtgacagag tgagatcctg tctcagaaaa aaaaaaaaa     480 caaaaaaaaa aaacccagaa aacaacaaca acaaaacggc agtatatttg tccccaccct    540
catctcttcc tttatgggta tttccctaat tgtgagagat tacctgtgtt ttaaaaggtg    600
gcttactgta tgcattgaga aaattaaatg acatttcaga ccagttccaa gtaccttttg    660
caaagctaga gaaataaaag tgaattctag tatctcaatc acagagtaaa actagagaag    720
gtctgttggg cttcaggcaa cattggtgtt cttggcaatt ttacccagaa gaatttatat    780
tcctataatt agtatttcct ccaaaattaa tgatcgcctg attgatttat ttctttccta    840
gcagcactgg aggtcccact tacctagtta gtaataacat ttgctcttaa tacatgagtc    900
agttttcttt tttccttttt tcttttcttt tttttttta catttccaaa acagaatacc     960
ctgcaggaag aatgggatgg cagtggagga gctctcactc acatatcatg taatgtggga   1020
ggcagggcta tgcgatagtc ataaagggtg caggcttcag aatcaaagga gtgaggttgg   1080
tgtccctgct tacgccctac tagctgagtg tccttcaggt catttctcct ctctcagact   1140
cagtggactg tttcctaaag cacagctcat aacaggctgt acgtggtaag accgtcggga   1200
agatggaagg agatcagtca tccctagaga gcattaagca cagtctcagc cacaaaacac   1260
ttcctcaaac atgatgcaag ccacacaggg catttggcct gcgtataaag gacatactga   1320
ggacagtgta gatgctcaag aaattagtcc tgaatgatca aggggggaaa gagagggtta   1380
atcttatcat atgtgggctc tcagagaaca cagagctata gaaggaagct gacttaataa   1440
gggtcaagca tgataggga gattaggaac cgtgtgcaat ctaatggaac cacagataac    1500
accttctagt acttttccc tttggccctg ccctgctga gacagggcca ctgctaataa     1560
ctcacattct tctcttctct cctctcaaaa agcccatttc ctgagcaagt atatgctttg   1620
gtaaggtcat tagcggtcaa catggttccc aagtttagtg aatactttca gataaaactg   1680
aagggtacaa aatcactctt tcctctctcc ctctccttgt cctacctctc acaataaaac   1740
gacttatcta ctaattacaa agacctcaat agtggaagaa atccatatcc tacataacat   1800
ggagagctag ctatataccc ttggcatcag ttttttatcct acttttactt tttactgact   1860
ttcatttact gaacaaagcc tcctttgcca aaggcagggt aaataaactc agtcacatcc   1920
tgtcttcctt acatctttgt ttatccataa actgtcgaag atacagatga aaatccacta   1980
aagcatgctt gaagcggtta cacgaaggcc aaataagatg ggaatggaaa tgcctgatgt   2040
taagggaaga tactacctaa aatgatactg agctggccag tgtaatgaca tgaaaacaaa   2100
acaaaaaaa                                                          2109
```

<210> SEQ ID NO 12
<211> LENGTH: 1965
<212> TYPE: DNA
<213> ORGANISM: Homo sapiens
<220> FEATURE:
<223> OTHER INFORMATION: lnc-C11orf35-2

<400> SEQUENCE: 12

```
gagagggtgc cagcggccgc agctgaagtt gggccgagag ccggcgacgg ccccgcgccg     60
gggtcgcagg cctgcaggag ttgagggctg cacctgctcg ctggagaggg agaggcagat   120
ttagtggacg cctggcatgg actcggactg gcctttggaa gctccctgcc ctgacggggt   180
```

```
tgcctgtcac cactgcgaag tgaggcttgg caggacctgc acctgagaaa ggctgtgtgt      240
ggtcttgggg tccacacctg cagagctaac ttactgccag acggcgactt actgtgggcc      300
accctcagtg aaccggggtg tcctcagctg ccctacagag cacttctgt gctggggatg       360 agtaggaact ctgggcgagg agggtcccag cgccgcccct cgatacagcc tggctctgcc      420
ctctgcccgt acttacacca ggtgggatcc ctgccctgca ttgcctgggg attggctggg      480
cttgggcccg ccctgctgtg gaactggatg ttttcaggga gcccagcctt tcctcatgtc      540
aacacagttc acaatatagt tttcaaagta cagtttaaaa ctcaaaagta aacttttcag      600
caactcaaag gtttgctgag tgatctgaag cactctggcc acttttgggg gccatgggat      660
ttggttcacc tgaaacagcc agtgagaggc cgggtgtggt ggctcacacc cgtaatccca      720
acacttcagg aggcagacgc gggtgatcgc tcacttgaga tcaggagttc aagaccagcc      780
tgggcaacat ggtgaaacct cgtctctact aaaaatacaa aaattagcta ggcatggtgg      840
tgggcacctg taatcccagc tacttggaag gctgaggcaa gagaatcgct tgaacctggg      900
aggtggaggt tgcagcgaga cgagattacg ccgctgcact ccagcctggg tgacgagaga      960
ctctgcctca aaaaaataaa aaatgaaac agccagtgag gaggaaggct ccccgccttc      1020 ccccgccgg aacatagcca tagctgctgc tgggacaccc tcttggtggg gaagaaggct       1080
ggttagcttc atcagagcca gcagcagcag accagggacg ggcacctagg cagtggcctc      1140
agagtgaaca ggagttcctc agaaacacac acagggacgg cgtggcgcat gctctgccag      1200
ctccatgcct ccttcccatt gtggggctgg ggtacgtagg gcagagctca tgacctccgg      1260
gaggacatgg gggtgggctc tggatggcac ctggcattgc cccctgctgg cctatgtgac      1320
ggtgtggagg gctggtcaca gaggtacgac catccctcca gaatgtgggt cggggctgtg     1380 gatgaggag taggccccctc atatcccagg cctgctgccc aggcacaacc cacttggcct      1440
atgcattcca ggctccatcc catgtgactc tgggcttagc cccttctggg gccacaggtc      1500
aggcaggtcc aggccccaag gacctcccag tgacaggcga ctgtgagctg gcagacagg      1560 agtgaagtca ggtgggggtt ctggcttgct gacaccagcg tttggagcct cctgctgctg      1620
cctggcttcc ctgcattccc tgttccctgc ctcaggcaag aaataaccaa gccgagttgc      1680
ctctgcacag cagtgagctc ctggtggccc tggcttctgg ggagccctgt ggatggcttc      1740
cttgcccaag tccaggcctt cttgttccct ttgtgtgctc cagagaaagg gggcagcacc      1800
agatccagat ccagggccaa ccaacagaaa gctgagtcca tcccaaactc gcccattctc      1860
agagcacaaa gaccccatga tctagggcaa acttgtccaa ctgttggccc atggaacagc      1920
tttgaatgca gcccaacaca aatctataaa ttttcttaaa cattg                     1965
```

<210> SEQ ID NO 13  
<211> LENGTH: 533  
<212> TYPE: DNA  
<213> ORGANISM: Homo sapiens  
<220> FEATURE:  
<223> OTHER INFORMATION: lnc-TMEM30B-5

<400> SEQUENCE: 13

```
tcatgtagcg ccagccacac caggaacaga agggtgccgg gtaccttccg catgcttggt       60
attctccccg cggggctctg accgctgccg ctctcaggca cctgtctttc ctctccgtcc      120
cagaatggag ccaagacaag ggaataaacg aaattcaata gtacacggag atcgggtgtc      180
tgggcagcgt cttggaaaaa ctatccacta cagtacaggt caagtgaagt tcttctgctg      240
atatgttctg ctactgcata agagacggaa tctatgttgc ctcgactggt cctgaactcc      300
```

```
tgggctaaag cgatccttct gccttggcct cccaaagtgc gaggattata ggtgtgagcc      360
acccaacctg gcctttgcca gtatttttaa atccaaacac ctatgcatgg tgcttactaa      420
taacacagtg gtattctaaa cattttttcac ctattattta atctttatta ttatcaccat     480
gttacagata aggaccctgg ctaaatagct tacccaacat tactccgtta ata             533
```

<210> SEQ ID NO 14
<211> LENGTH: 760
<212> TYPE: DNA
<213> ORGANISM: Homo sapiens
<220> FEATURE:
<223> OTHER INFORMATION: lnc-PLAC1-1

<400> SEQUENCE: 14

```
gggaaggtag aaggtggggt ctgccggacg cgtgttcctg ccaccaggtg cccgctcccc      60
gcgaggccgg ctcaggagca gaaggaagcc cggtgccagc cagccttcct gaaagaccaa     120
gcccgcgcca tccggcttcc tccagtggac gcctgcagga cccaggaaca ctacatcaac     180
actgttggcg gggacctgga cacagaagac tcctgtttca agaaaataca atcatctctc     240
aaaggctgta attatatgc atttaaaaac tctaggcatt gaaaaccacc caagtgtccc       300
aaatagaagg gtaatatata atcaatcact cagtgtaata ttatacatcc tttaaaaatg     360
ttattgggaa atgttttatg atctgtaagt ccaaggaatc ctctcccacc atttctttcc     420
ccccgctgtt cccccatacc cacacttctt tgttccaatt ggcatgtaaa tttggttttc     480
ccgccaaatg agtcagtcat gatgggaacc tcaactgatt tgaacagatg tgtgtcaatg     540
ttacttggaa aactagatgt caataaccag ggtcacagaa aaaggcagtg gtcacaactc     600
tgtaaaaatg tatgcatgca cacagacaag aactaaagtg gaaccccaca caggaaaaca     660
gtgggctgta ctccagtgct gggacattga atgactgtat gctgcttttg atttccgtta     720
atatgggcaa ctgtccaatt aaaaaaaaaa ctcctaagga                            760
```

<210> SEQ ID NO 15
<211> LENGTH: 1775
<212> TYPE: DNA
<213> ORGANISM: Homo sapiens
<220> FEATURE:
<223> OTHER INFORMATION: lnc-FN1-3

<400> SEQUENCE: 15

```
gtccctggga cccaagccgc tgcagcacag tatcattttg aggacagagc cactgccaga      60
atgcttcctg tcctggggcc cggtaacccc tgcatgtcct catcactgga gcccaatat      120 cattccacag ttgtatgagg agtaaaaata actataaata aagataactc aagaattcta     180
taagcaagca tacacatgaa attcatttta taagaggaaa gctaactcca tctctcttga     240
aatatggaat aggttcttga agcaattcta aatgctgatc tgctggaatg atggcttcat     300
tgcacaagaa ttctgcttag ttcattgaag tctccttgaa gaagtcagtc tgagaatggg     360
ggaattccgt tgttggtcag aagaattctt tggtcactat tggaagtggg ttcagtttag     420
ggtgactatt gatcaacagg gttcatgggt ttgctaaaac tcatttcagg caagctttgg     480
aagtgcagtt cgcttggtgc ttatgggggtt aaaaacagga ggaagagaat ttcacattat    540
tggagggcct gaaaggaaac tgattcccgc aagatgctca gacaagatca acccagccc      600 cttttctggt ttggaatttc tctgggctat aaaggtagaa gaaaaggccc tgcatgggcc     660
cactctaagt gcttggaggt tttagataat tttattaaat tgtagaatct taaacagaac     720
```

| | | |
|---|---|---|
| tacaaggttg cttttaaaac cagatctcag atttctttga gctaacaaat ggtaaaatgt | 780 | |
| atctttagta ttagagtgag ataaaggtag ttataactttt ttttttttact tattttatgt | 840 | |
| taacgtatgc aacaaagggt acaaattgta ggtacgcagc tcattgaact tttatgtctg | 900 | |
| cacatgccta tgaaaccaac acccagagta agatgcggat aattttctgc tccctgaaa | 960 | |
| attcccttgt gccttttcct catcagtacc tccaaaggta accactattt tgatttccat | 1020 | |
| taccatagat gagttatact tgttttgaa aagattattt gaatgtgta atataaataa | 1080 | |
| tagcggttgc ttatcttaca gaaatatcac tgagaattca tttcttctct ccttcattta | 1140 | |
| ttcatttgtt caaacactg tctagtacca acattgtcca ccgggcgttg agaatacaat | 1200 | |
| attgaagaag agtcactgcc tgccctctgg aaaaatcaga gtatttgaaa gaatacacac | 1260 | |
| aagtaaacag gcagctatgg caaagtgggt aaaagctgca aaacagggaa gtttcgccaa | 1320 | |
| gtgtcagatg ccaagaagtg tcagatgcca agaagaaagg gtgcatgaca tagacttggg | 1380 | |
| ggggtcagta gtggtttctg gaacgagtga catttagact gaaactggaa ggatatgagt | 1440 | |
| aagggctaat cggaccaaga tgaagagata cagaagcaga aggaacagta ggaacaaatg | 1500 | |
| ctcagaggca aaagaaagct ttgaatattt gaggaactga aaagcaaaac aacaaaaaat | 1560 | |
| agccatccct tgactagaca agtgacctgg ggtcagatcc tgaagggctt tgcagatcac | 1620 | |
| ttttccgctt gtagactttg tacttgactt taagggccat ggagagccac tgaagcatttt | 1680 | |
| tcagcaaggg actgtcatca gcagattggt atttgtttg aagtagcaca tgtaagagaa | 1740 | |
| aataacaata tggacaaata aagagtttga aaaac | 1775 | |

<210> SEQ ID NO 16
<211> LENGTH: 1791
<212> TYPE: DNA
<213> ORGANISM: Homo sapiens
<220> FEATURE:
<223> OTHER INFORMATION: lnc-LCN6-1

<400> SEQUENCE: 16

| | | |
|---|---|---|
| agctggggtc tcatgtctgt ggtgctggaa tccagagccc tgacgggaca gcagcagcag | 60 | |
| gaactcgtta cgctgcagca gggcccacac ggacttggct tccgccaggg acacccggtt | 120 | |
| gtccttgttg aagtcagcca tgagcaggac ctggccaacc agcgccggca gggaaggcag | 180 | |
| gtctcccagg ttcgcctggc gtttgggacc aaaagaaagg aaaagccagc tgatttgatg | 240 | |
| tctgggagca cgacctggcc tttacctggt cctcctggcg gggtggtctg ccggccagac | 300 | |
| cagcacatct gccaggttag gggtcccagc ccacagctac acgggtggag gacgcagcca | 360 | |
| gcaatgtgtc agctcactct gctggcctgt gtggctgctg ccagacagac ctcccgcctc | 420 | |
| ctggcagcct ggggtgcacc tggggagctc ggggtgggc acctgggcag agaagcctca | 480 | |
| gagcttccct gaggatgaga atcggcacag gcagagggc acgcactggc tgaagccctg | 540 | |
| ggaagcggcc ccttttccaca agccctggtc tccattcggg gcacctgccc tgctggacac | 600 | |
| acggcccttg actgcaggag cctcccctcg acctcagctg ccagcccacc ggcgccccca | 660 | |
| acccttgccc ccagccctgg agaggctcct tccctggcag ggctcatgcc caggggctgg | 720 | |
| gggatgggag gtctgcccag ggtccacttg ggccatctg tgcctttgcg ctgggcatgt | 780 | |
| tggtgccagg gccgcctgct gggcatatga ccgtggtgtg gactcctgcc ctgcccccta | 840 | |
| ggagagctgc ctgaccttga ggaagctgag ggtcatctcc cggaattcct tgatggaggt | 900 | |
| gccccgggtg ggcttgtcaa acagtaccag ctcccgccgg ggggccgcat ccgacccggc | 960 | |
| cttggagtcg agggtctcct caatgccaca cttgatggtt acatccttgt cccgccagag | 1020 | |

```
cccgctgtac acctggacag ggccacagag gtcctccgtg cagacatccc cctcccactg    1080
cacgggcagt atcagcccca ggcccacccg ccctgccagt ggctatacct gctgcccgg     1140 ggccaccgag aggcaggtcc tccactccac catatgcagc tcacacaggt cctggcagac    1200
ggagcccgag atgatcccct tgcggtactg gtcacactga ggagacaggt gcaggcgtgc    1260
cgggcggggc agccacaccc ctgccccact gagcccctgc ccacaggccc gaagctggca    1320
ggggcctcca cttgctgcag ttggaaagct gccagcccct cacacaggca gtgccggggc    1380
cctgggtcat gccattggtg gctgcaggat ggggctgtcg gctgcagggg cagccccgcc    1440
aaccctccgg tccggtcccg tccccaccat cctggctcct gtaacaggac ggcacagcaa    1500
aggccactgc ctggacatga gacacacacc acacccagtg tcgacccccac gccagggca    1560 gaggcaggaa cctggaggca gctctccgcc cagccgaccc agctctggac catccaggca    1620
ttggccggtg aactagaatt cacactagtc cctaatatct acaccaccag ctgccacacg    1680
cgcgctctct gcctgactct tcattcctgc ctcgggtgac gccaggaggg aggatgcacc    1740
ccctgactca tggcgccctc cctgcccgga atagtaagtg agacatttct g             1791

<210> SEQ ID NO 17
<211> LENGTH: 721
<212> TYPE: DNA
<213> ORGANISM: Homo sapiens
<220> FEATURE:
<223> OTHER INFORMATION: lnc-C14orf166B-1

<400> SEQUENCE: 17
gggtgacaag aagacttccg agcccaaagc catgccagac cttaacggga tccttttccca    60 gagccctcca tggagaaaac agcaaaatga agcccttacc tgcttgctgt ctgcaaggga   120
gggagccgag ccccagctga taatcccccca gcactcaccc ttcctgagct gagacttcgg   180
ggctgtggag accagcacag gacatagtgg tgcttttaa atttattttt aactgtttct    240
catatgtagc aaccccctcct cccctcctgg gcatgtttac acaggtctg ctctgggggc    300 tggcctggct gtgaggtttc tggggaggca gagaggcagg gactttgggg ccttagtcac    360
catccatggt atcacctcat ctcacttcct gtgagggaca gggcctggct gatgtgatcc    420
cagctccccc cagttcagga ctgtctttca gctccttttgc ccctggaggt ggggggctgct   480 ggctgaggag gggtcaaggt gagttcaaga aagctacctg tggaaaatgg accaggttgg   540
gggggtgatt gcaaagtctc cccaaagcct ggctcctcat gctcagtgcc aggggcagaa    600
cactggggag ccaggtatag agagccttcc tgtcataact gccagtcctc ttcctccaag   660
gcctctgcat attctcatgt tcccctcacc catcatgcca gccaccccta tccctcttct    720
a                                                                  721

<210> SEQ ID NO 18
<211> LENGTH: 1071
<212> TYPE: DNA
<213> ORGANISM: Homo sapiens
<220> FEATURE:
<223> OTHER INFORMATION: lnc-AK1-1

<400> SEQUENCE: 18
cagcggcccc gcctccagcg catgccctac cactactacg agcccaaggg gccggacgaa     60
tgtgtcacct acatccagaa tgagcacagt cgcaagggca accaccaccg cttcatcacc   120
gagaaaaggg tcttctcatc gtgggcccag ctgaataaac acacctacgc tccggcttcg   180
```

| | |
|---|---|
| tgtcctgtgt cacctgggtc gagcacagcc ttctggtcca gcgctgcatg cggcctcagg | 240 |
| accacgtctt ccggttgggg gctcccagta aagcgatcct cagcttcttc agcagccagt | 300 |
| ggccagtgag agcactgaca cggctcccgg gacctcggca ggatggaaga gaagctgaag | 360 |
| aaaaccaaga tcatctttgt ggtgggtggg cctggctcag ggaagggcac ccagtgtgag | 420 |
| aagatcgtgc agaagtatgg ctacacccac ctctccaccg gggacctcct gcggtccgag | 480 |
| gtcagctcag gctcggccag gggcaagaag ctgtcggaaa tcatggagaa ggggcagctg | 540 |
| gttccactgg agacagtgtt ggacatgctc cgggatgcca tggtggccaa agtcaatact | 600 |
| tccaaaggct tcctgattga tggctacccg cgggaggtgc agcaaggaga agagtttgag | 660 |
| cgacggattg gacagcccac actgctgctg tatgtggacg caggccctga gaccatgacc | 720 |
| cagcggctct tgaaacgtgg agagaccagc gggcgtgtgg acgacaatga ggagaccatc | 780 |
| aaaaagcggc tggagaccta ttacaaggcc acagaacctg tcatcgcctt ctatgagaaa | 840 |
| cgtggcattg tgcgcaaggt caacgctgag ggctccgtgg acagtgtctt ctcccaggtc | 900 |
| tgcacccacc tggacgccct aaagtagcaa cgctggagcc gcttccccag ctcagagccc | 960 |
| cgccccaccc cgtcctgatt cgaggtcctc ctggcctgag cgcagcgcct ccaccctgcc | 1020 |
| ctgctgagca cagacggagg aagccgctta tcctgttttc atggacagct g | 1071 |

<210> SEQ ID NO 19
<211> LENGTH: 1868
<212> TYPE: DNA
<213> ORGANISM: Homo sapiens
<220> FEATURE:
<223> OTHER INFORMATION: lnc-ZCCHC7-2

<400> SEQUENCE: 19

| | |
|---|---|
| tgagatagtt cataagtctg caaaaggctg tataaataca tatttacat ttactattat | 60 |
| taattttgta gtaaatttga gtacagcact ctctttatct gtggaaactt cagactctcc | 120 |
| cctattactt taatttcagt gagacattat taaatataag tgggcttaca catttgtttt | 180 |
| gctttactga caaataatac acaacttgga ggcttttttt tcctttctat tcttcctcta | 240 |
| aatgttcaac acttttctga ttttgtgatt tgaggttgtt taatagcttc ctgaggctcc | 300 |
| attgagaccg tatatacgtg acacttaaca gtctagcctt cctcggtaca tatagatata | 360 |
| tgatggtggc tttgcctgta gtaaattcat gccaaaacat aggctttcag tgcctattac | 420 |
| atatggcttt cagctctctc tactgaggga tgtaggagtt tatttctgag gtctgagcct | 480 |
| cttttccttt acttccttta ctctttccta agccttcttt ataaaaacta tgcatgttct | 540 |
| attgttttcc ttttgattc cctttctttt attatcccca gtaggagtga cttgtaattc | 600 |
| tcatatgtta gaaaggcaga tctcctggtt gaagaaaaga tccacccaag caagtcagca | 660 |
| tgtttaataa ttttgaggg ggatctcaaa tgtgggaagg attgttatat aagacaacca | 720 |
| aatgatgaca tgagacaata aatgctatag gaattatgga ggaataatta gctatttatt | 780 |
| ttcttggtta gggaagagat attattagtt gtagaagtaa ttactaactt ctacattttt | 840 |
| tattgtggaa atcaaaaata tatatgaa ataaaatgt taaattgac ttcagtgtcc | 900 |
| cataaaccag cttcaacaat taccaaattg tgaccaatct ttacacacat gcacaggtgt | 960 |
| ccctcagtat ctgtggggca ttggttctag gaccacttat ggataccaac atctatggat | 1020 |
| gctcaagtcc ctgatataaa atggtggact atttgcatat aacctgtgta catcccgtat | 1080 |
| tatttaaatc atccctagat cacttataat acgtaataca atgtaaatgc catgtaaata | 1140 |
| actgttatac tgtattaagg aataacaaca agaaaaatgt acatgttcag tacagacgca | 1200 |

```
atttttttttg tgtgtggaat attttcattc caaggtcagt tgaacccatg gacataggag    1260
gctgactgtg tgtgtgtgtg tgtgtgtgtg tgtgtgtgtg tgcatacaga cacacatatt    1320
tctgaaatgt aaatattctc ttcttaaaaa aattattatc acagctaaac aaattaccag    1380
taattctttt atcctcatat acccggtgtt cagattttct agattggctc ctaattttttt   1440 tacagattat ttgaatctga ttcaattcat gtactgtaat gtttgataac ttaagtaccc    1500
tttataggtt ctcttttacc tcttctttat taaattcctt gtaatttgtt gtactaaata    1560
gattgtcttc tagaatttcc tgtagtctga attatgtagt attgtttcac atgttccagt    1620
gtcctcttat ttcctgtgag ttggtagtta gatctagaag cttgattaaa ttcagatttt    1680
ctctctttag atcatcaact ttagatcatc aacttggatc atttgtttca ttttgctttt    1740
gatatgttgt tttttagaat tacctcttaa aattttgatt taattttata atcatgtaaa    1800
atgtttataa atttccaaat tcagatcagc aaaacacaat aaaatctatt cagagaaggc    1860
aaaccttc                                                             1868

<210> SEQ ID NO 20
<211> LENGTH: 618
<212> TYPE: DNA
<213> ORGANISM: Homo sapiens
<220> FEATURE:
<223> OTHER INFORMATION: lnc-IDS-1

<400> SEQUENCE: 20
gcaaagtatg tcagaaagca gatggaagcc aggcccctc  ctgaaagagg ctccttgaag      60
ataattctaa catctttgtc atcagtgttg acatctcttg attgtatcct gtcattccat     120
ttgagatctt cctggttctg gctggcatcc tctgacatca ctccagcaga agaaagggaa     180
ggaacacgct gcattactgc gtggctggga accctgaatg ctgtagtgtc accactgccc     240
tgtcctgtac ctacctatct tttcactcat ttcctccaag ctcaggtttt cagtttgggg     300
tatgtgccac ctaacagtga gctgtggaac tgcagcacaa tcatcaaatt caaaaaaggc     360
aaggacatct tgctcagttt ttaagatacg ccatagatgg agtaaaccaa aacctttgat     420
tccagatcct taaccctgat taaaaacaac acaaccttc atgttgattt aaaacatccc      480
ttgcaaaaga tggtttgaat attccaagtt ggaaataccc agtctttaa  agttacagca     540 cccttttga tacaaaaaat gtgcatgaca gaaattgtac agtgagtagt gttataaaaa      600
taaccaaaca caccaaaa                                                   618

<210> SEQ ID NO 21
<211> LENGTH: 632
<212> TYPE: DNA
<213> ORGANISM: Homo sapiens
<220> FEATURE:
<223> OTHER INFORMATION: lnc-DLK1-4

<400> SEQUENCE: 21
acttgcaaag tctcggctta gttcctggca ctctgaggtc cacctccttc ctgaggctgg      60
tggttaccgt gctaatgagc taggccgcag cggctattag acatggctgc gtggggtgtc     120
ctgccagccc agcccgtca  ccacgggctg cctcgagcag ctcccccagc accaggcact     180
ccagatgctg agcagcagag tctgcccatg aaggatggat gcactacccc tgcctccata     240
ttcaggggtc tcaggcaagg agcccgtcct cactacacca cacatggagg gcatgaggct     300
ggaccacacc agaacgtccc tcccccccgga gcctggagct gcaggtcttg atgcggagag     360
```

-continued

| | |
|---|---|
| gtttccatct gggtctctcc tcagggatga catcatccgt ccacctcctt gtcttcaagg | 420 |
| accacctcct ctccatgctg agctgctgcc aaggggcctg ctgcccatct acacctcacg | 480 |
| agggcactag gagcacggtt tcctggatcc caccaacata caaagcagcc actcactgac | 540 |
| ccccaggacc aggatggcaa aggatgaaga ggaccggaac tgaccagcca gctgtccctc | 600 |
| ttacctaaag acttaaacca atgccctagt ga | 632 |

<210> SEQ ID NO 22
<211> LENGTH: 2001
<212> TYPE: DNA
<213> ORGANISM: Homo sapiens
<220> FEATURE:
<223> OTHER INFORMATION: lnc-C6orf146-3

<400> SEQUENCE: 22

| | |
|---|---|
| aaaaaagcct gccatgcaga aagtcactga gaaacctgct ggcctccatg gtggcacgtg | 60 |
| ggggagggag gagaagaaaa ctcctgaaag aatgtggacc acacagcatg ctctggtggg | 120 |
| tatgtgggct gacaaagaac agggagcgct aacagtgaaa atgaagagcc tgccccgcct | 180 |
| cccagcgtgg accttgacct ggggccagac caaggccact ttatagaaac gtccctggag | 240 |
| cgtgtctcag gtggccctgc ctgcatcctg gcctacctct ggggcccttc ttacccacag | 300 |
| tcctactttc cacccacctt gaccccaaga ggtgttcatt tataacgccc ctgcatcttc | 360 |
| tcaacttcaa agtcagctcg gacctcgttc acccagacaa gaccttggct gagtcttgac | 420 |
| aaactggcac agggtccccc gacagaagac agctttcctt tctctttgct ttcctttatc | 480 |
| ttagccgagt ccggcctccc cagcactctt ttccatctgg ggacagttcg tgctggtggg | 540 |
| aattggcagg ggcacacggt ccagacagag acaactgaaa cacaggtgtc ccgctggtgt | 600 |
| gccagcaggg cggccgtcct accaggagca ggacactttg ttggccactg cccatgcaat | 660 |
| aatcagcgtg ggacaaacag tcccatgggg agtgaggtga tgtgaagaaa aggaagccga | 720 |
| agaagagaag aagctgaagg gccagtaaac acacacatag acgctcaccc tcccctccgt | 780 |
| tggaaaaatg aacggctgct gttgccgagg gctggtgagg atgaggcccc aggcctgcag | 840 |
| gagggcacat ccggttggcc gcctcgacgg ggccatctgg gtagctgctg ccctttgcat | 900 |
| gtaaataaag ctcctcaaag ccccatttca caactgctgg gagaaacagc atccttccct | 960 |
| ccttccctat atttccaggg aggaggtggc tggttttttt tgttgttgtg ttttttttgt | 1020 |
| ttgtttgttt tgttttgttt tgtttttttcc agatttctcc cagccacatc cagcttcttg | 1080 |
| ttctgtaatt ttttttttcca aattactgac tgccttcttt caaggggaaa tggaactcag | 1140 |
| aaagatggga agatacatga taagagcact taagagagaa gcctgtccat ttccactaag | 1200 |
| gttgaagtgt gcatactcca ggatccagtc cttcatgtct acacaaggag tcccaggaaa | 1260 |
| aggtctgtgc aaaacgtttg taattgcaac ggagcagcca cgacctagcc ctccttcagc | 1320 |
| agaggaatga ataaactggt ttattcagtc aacgcagcag ttaaaatgag agaattagtg | 1380 |
| atgttgaaag gaaaatgaa gagcaaacag atacagtagg aagttatcac gtacatttca | 1440 |
| aaaacattca aaacaaccgt acatatttat ggattcatgt aataatgcag taaaaataca | 1500 |
| aaatcagagc caggactgtg gcacactgaa ttcagcacaa tggtcgtctc taaatgtggg | 1560 |
| ttcatgtggg aggaggtgac cccggggtgg gggcttctgc tgtatttgtc atgtttgggt | 1620 |
| tatttgaaag ggagagagag cactgtagtt atacagtaaa atgcaaacat attttttatt | 1680 |
| ttagtggtga gtatacaggt gtctgttgtg ctgttttctg tgtgtttgaa tggtttcata | 1740 |
| attttttagaa aattaaacca tgaggtcgga tatggtggct caccctgta attccagcac | 1800 |

```
tttgggggt cagagcagaa ggattgcttg aagaccagcc tgggcaacat agcaagattc    1860
tatctttaca atttctaaaa cattttcaa tttaaaaatg ataaacaatg aaaaactgca    1920
aagaaataga ttgaaaagtt cacagttgct tttgccacat tttgtgaata tgttattttt    1980
ataatgaaaa attacagata a                                              2001

<210> SEQ ID NO 23
<211> LENGTH: 557
<212> TYPE: DNA
<213> ORGANISM: Homo sapiens
<220> FEATURE:
<223> OTHER INFORMATION: lnc-HMOX1-1

<400> SEQUENCE: 23
gcgaaactcg gcggctgagc gtggaggtgg gagaatcact tgaccccaga aggttgaggt      60
tgcagtgagc tgtgattaca ccactccact ctagcctggg tgacagagcg agaccctgtc     120
tcaaaaagga aaacaaaaaa gattctactg aggggagag ggtactgagc ttgggcccct     180
catagtaacc tgggtggaag gttttgagat cttttgattag ggttctaacc tgggcttgca    240
tatcctgaaa ttgcatgcag atgttctgag gagagcggat ctgtagcttc tgttaacttc    300
attagtggca acagagtatg tagggtcag gctcttgctc cctgggcaag ttatgtgact     360
ttgtcaagct tcagtttcct catcagtaaa atggggataa ggacagtcct taatctctca    420
gagggctgct tgaaaatgca tgtggtgttt agcacaattc cttcatgcag attacgtaat    480
caggatgtat gatttccaa gcagttcatg aatcctgaaa acttacgaag tgggtatggg     540 aagagggag ttggagg                                                    557

<210> SEQ ID NO 24
<211> LENGTH: 645
<212> TYPE: DNA
<213> ORGANISM: Homo sapiens
<220> FEATURE:
<223> OTHER INFORMATION: lnc-TBC1D12-1

<400> SEQUENCE: 24
gaaataggaa agtatttaat ggtttcaaca taaaatcaaa acacataagt cataaataga      60
ataattatga cttgcataat tatgaccagt attgtcaggt tttatgtgtc tgctggtaaa    120
actttggaat atgatttgca gaaatctcag ttcaggagtt tagcaaagtt tatgaatgtg    180
tacagcatta aaaagtattt aaaccaggct agcctcgaac tcctgaactc aggtgatctg    240
cctgcctcgg cctcacaaag tgctgtgatt acagggtgtg agccactgca cctggccgat    300
aacagatgtt ttaatagtaa gataaaaagt aaaatttcca gtgtgtcgaa ggaagaaaat    360
tacagcctag aattttatct tcatgtacat tatttaagtg tgagggaata gtttcagtga    420
cattatgtca ttgaagacct tagaagattt ccctcgctaa aggagataaa gcgactggca    480
caacatgtat ttctctgagt aattagaagt gttctttct ggctgtactg aagggactt     540 catgatttct tcgttttgt actcttagtt ttataatatt gcatagtagc taaggcctgg    600
ctgtagcagt tataaactgt tctgcaagtg cgggaagtaa tagtt                   645

<210> SEQ ID NO 25
<211> LENGTH: 997
<212> TYPE: DNA
<213> ORGANISM: Homo sapiens
<220> FEATURE:
<223> OTHER INFORMATION: lnc-CTD-2517M22.14.1-2
```

```
<400> SEQUENCE: 25
cctggagctg cacccacacc actggctgga gctgctggcg accacctata cccattgccg      60
tctgaactgc cctgggggcc ctgcccagct ccaggccctg gcccacaggt gtccccttt     120 ggctgtgtgc ttggcccagc agctgcctga ggacccaggg caaggcagca gctccgtgga    180
gtttgacatg gtcaagctgg tggactccat gggctgggag ctggcctctg tgcggcgggc    240
tctctgccag ctgcagtggg accacgagcc caggacaggt gtgcggcgtg ggacaggggt    300
gcttgtggag ttcagtgagc tggccttcca ccttcgcagc ccggggggact tgaccgctga   360 ggagaaggac cagatatgtg acttcctcta tggccgtgtg caggcccggg agcgccaggc    420
cctggcccgt ctgcgcagaa ccttccaggc cttttcacagc gtagccttcc ccagctgcgg   480
gccctgcctg gagcagcagg atgaggagcg cagcaccagg ctcaaggacc tgctcggccg    540
ctactttgag gaagaggaag ggcaggagcc gggaggcatg gaggacgcac agggccccga    600
gccagggcag gccagactcc aggattggga ggaccaggtc cgctgcgaca tccgccagtt    660
cctgtccctg aggccagagg agaagttctc cagcagggct gtggcccgca tcttccacgg    720
catcggaagc ccctgctacc cggcccaggt gtacgggcag gaccgacgct tctggagaaa    780 ataccctgcac ctgagcttcc atgccctggt gggcctggcc acggaagagc tcctgcaggt   840
ggcccgctga ctgcactgca ttggggggatg tcgggtagag ctgggggttgt cagaggctag   900 ggcagtgact gaggacctgg gcaaaacctg ccacagggtg tgggaacgag gaggctccaa    960
aatgcagaat aaaaaatgct cactttgttt ttatggg                              997

<210> SEQ ID NO 26
<211> LENGTH: 1118
<212> TYPE: DNA
<213> ORGANISM: Homo sapiens
<220> FEATURE:
<223> OTHER INFORMATION: lnc-ZNF276-1

<400> SEQUENCE: 26
ttcaggcgtg ttttccctgc aagccatggg taaccagggg tcaagcggtg ggccacatcc      60
cacagaggag atgcgggctt gggggatgcc caggagagc cgcctactgc aggagaccca     120
ccaagcttgg cggccgtcga ctgggccctc tccagacact gctgtgctag cttcagcatc    180
ttggaggtgt cgggggggcac agtttcccca gcttctgggg gagggacaag aaggctggtc   240
acagtcggct ctaccactgt tacttactgc tgagataaaa tgaggcaacg gaaaaggcct    300
ctgggaagtg gccgttttac agagacaagg acgtgctgag gggatcgcct cacccatctc    360
ccaccggctg tgtccccaaa gtcctgcctt cccgtagctt ggcatggagc acctctgcgc   420
gaccatggac ctgctcacac agcccttctg cgcgccgtgg gagctgcctc tctgtgactc    480
gcccctggac ccaccgcccc agcgcctgac ccacctccct gctgcccttc acagaaaact    540
tctcatagac tcccattttc tcatcccgcc ccgatttagc ccccgactcc ccccggaaac    600
tgcccttacc cgtccccacc ttgccagaca cggtgggcca ctggagttcc tctgtcttct   660
gggactttgc tctccccagg ggatcctctg ccactcctcc acccaactcc tcaatcttgg    720
agcgccagag ctcagccgag ctcaccggct cctagggag ctggggcaac tgttagctcc    780
ccctgacctg tgtgatccta cgtccagtgg ctgccccgac ctctgtgatc ccacgtccag    840 gggctcccc gacctctgtg atcccacgtc cagtggctcc ccgacctct gtgctcccac    900 gtccagtggc tccccgacc tctgtgctcc cacgtccagt ggctccccg acctctgtgc    960 tcccacgtcc agtgggtccc cctgacctct gtgatcccac gtccagtggc tccccctgac  1020
```

| | |
|---|---|
| ctctgtgctc tatgtccagt ggctcccct gacctctgtg atcctttgtg cagcggctgc | 1080 |
| tggcctctca aacttaatgt gttcattgcg aacttgc | 1118 |

<210> SEQ ID NO 27
<211> LENGTH: 1177
<212> TYPE: DNA
<213> ORGANISM: Homo sapiens
<220> FEATURE:
<223> OTHER INFORMATION: lnc-PGRMC2-1

<400> SEQUENCE: 27

| | |
|---|---|
| accctaccaa cctcagggac tgttctaaga gcaaaatgaa atgagactga gctctgaaaa | 60 |
| tgcttaaatg cttttcaaag tagagtgatc gtgctttctg tagcatcaaa acagtcctct | 120 |
| ataaatgggc aaagtcaagg catggactgg atctgacaac agagaatggc ttgagggctg | 180 |
| gaaaagaaa aaaatgcaaa tgccccaaat ctctgcttcc cttacagtgt ggaaatcgcc | 240 |
| ccataacaca ctgcaccagg tagggttaaa ttgatcccaa atgtttcagg aattttaat | 300 |
| gcccttcgaa gagacatttc caattcttca tctgcccaaa gtaatgctgc taacctacta | 360 |
| tctgtcagtt tcctcagtgc tttgaagatt tttctaaagt catctgactt ggtttccctt | 420 |
| tgatttcaaa ttcctgctta ttatatgtat gaccttgagc ctttttaact catctgagcc | 480 |
| tctctgtttc ctcatctata aattgtgaat aagaagacgt tactgtagga ttattagaaa | 540 |
| ctttagaaat aatactttta ataccagcat agtgcctgat ccataggcat ccaggacatg | 600 |
| ccagctaaga tcattgatta ttgttgtcgt tttagtatc atacagtaga aagaacaaca | 660 |
| tctttgaaac cagacaatcc cgcatttaaa tcagctctgt cacttacgaa acgtgtaatc | 720 |
| ctgaataact gaagaaaact ttttgaagtt caattttgag ataatgatgg atgatttcag | 780 |
| actttgtgag aatttcagag gtatcggcag taggttgaat ggtgaaccct ccaaaagata | 840 |
| tatctatgtt ccaaactcag aatctgtgaa tgtgacatta tttgggaaaa gggggttttg | 900 |
| cagatataat taagttaagc atcctgagat gagatcatcc tggattttct agatagggcc | 960 |
| taaagccaat aatgagtgtc taagacagaa gaagacacaa agaagaagag acgggaatgt | 1020 |
| ggtcacagag gcagagactg gagcaatgca gccacaagcc aaggaacacc tggacccacc | 1080 |
| agaagctgga agaggaaaga agggatttct ttttcttcta gagccttggg agggagcatg | 1140 |
| gccctgctga caacttattt tcagacttct agattct | 1177 |

<210> SEQ ID NO 28
<211> LENGTH: 1226
<212> TYPE: DNA
<213> ORGANISM: Homo sapiens
<220> FEATURE:
<223> OTHER INFORMATION: lnc-ACOT1-2

<400> SEQUENCE: 28

| | |
|---|---|
| gagccggtgc tgcagaccgt gctggaacct ggagatttgc tgtatttcc tcggggcttc | 60 |
| attcaccaag ctgaatgcca ggatggagtc cactctctgc acctcacctt gtccacgtac | 120 |
| cagcgcaata cctggggtga cttcttagag gccatactgc ctctggcagt gcaggctgca | 180 |
| atggaagaaa atgtggagtt tcggaggggt ctgccccgag acttcatgga ttacatgggg | 240 |
| gcccagcatt cagattctaa ggatccgcga agaaccgctt tcatggagaa ggtgcgggtc | 300 |
| ttggttgccc gcctgggaca ctttgctcct gttgatgctg tggccgacca gcgagccaaa | 360 |
| gacttcattc acgattctct gccccctgtt ttgactgata gggagagggc actaagtgtt | 420 |

```
tacgggcttc caattcgctg ggaggctgga gaacctgtaa acgtgggggc ccagttgaca    480
acagaaacag aagtccatat gcttcaggat gggatagctc ggctggtggg tgagggggggc    540 catttgtttc tctattacac agtggaaaac tcccgtgtgt atcatctgga agaacccaag    600
tgcttggaaa ataccccca gcaagctgat gccatggaac tgttgcttgg ttcttatcca    660
gagtttgtga gagtggggga cctgccctgt gacagtgtgg aggaccagct gtccttggca    720
accacgttgt atgataaggg gctgctgctc actaagatgc ctctagccct aaattagttt    780
cttgttgatt gctggaaaca aggcagtagt gattctccgc tgccactgct accttttttt    840
tttttttttc cttaaaactca cgttcttacc ttgataagca tcagtgtgct cacatttacc    900
tttatcactg cttcagtgtc acaaacctcg gaaggtcttc taggaagaac catctcatct    960
aggtacaaaa ggaaaaggag aagttggagg tggaaaaaaa acccttgatc cgtgatcatt   1020
tcagagcacc aacttcatca ccttcaggct tcagtgtact gggtaacact gaccatgtcg   1080
ttctgcttga gacagatatt agattttttt tggaatttgg atctttcatc tgagttcttt   1140
ttcatgggcg ggtcggggtc agtatcctgt ttgttattgt taaatttgta tgaaccttag   1200
aaaagttatt aaagtgccaa agaatg                                         1226

<210> SEQ ID NO 29
<211> LENGTH: 480
<212> TYPE: DNA
<213> ORGANISM: Homo sapiens
<220> FEATURE:
<223> OTHER INFORMATION: lnc-DRD5-10

<400> SEQUENCE: 29
gaactttgag ttctattaca gaccctgtgt agtgagaaaa gctgggatac atgaagactg     60
ccatcccttg agtcacttgc cctgtagctg ccactgttgg aaaagggctt gcttctgtgt    120
ccttgtgccc actttgaaaa tccctgggaa gtccttggag tcagatgagc aggcctccgc    180
cactctgcca aaaagtctgt tcagaagttt cacatcacta gagaagagag aagaaggaca    240
tttgtactgg gaggagtcga ccggtcccag taaggagaaa gtagctacag cgtcatgggt    300
gagctgggtc ccccaaaaag gaactttaag ggaatggact gaatcaagtc tgagatgtcc    360
ccaaagcaag accaaagaac tgaggaagag aagcattcat cagaaaccaa aattcagcta    420
caagtgagca tccagatgga ggtattatga agaggaactg agactgaggg caaaaggtgc    480

<210> SEQ ID NO 30
<211> LENGTH: 1401
<212> TYPE: DNA
<213> ORGANISM: Homo sapiens
<220> FEATURE:
<223> OTHER INFORMATION: lnc-EPCAM-1

<400> SEQUENCE: 30
gggattacag aaatgagcca ttgcacctgg cccagtgtct actttctttt atcaggctaa     60
acagctcagg acacagatag aatttggact taggtccgtg tgaatccaaa gggccatgct    120
caactgagca gccggcactg cctcgctgaa cagccaggat tctgggagtg ctactttgta    180
caacatttta tgaaatgttt ctggcctcct tctagaccag agcagaaagg ggtggttagg    240
atgttctaaa taccaacccc ctctactcca tccccaggtt catgacaact ttttaagctg    300
agcatactgc aatcacttaa ttcttctaga cctaagataa gccagtagcc acgtccactc    360
tgagcctgtg agcaggcagg atcaagtcta agagcatctc ttctttggaa tcttaaggcc    420
taggatccca gcagttttgg ggtctaaaga cttttcaggc tcccgaaact ccctctattt    480
```

```
ttaataattt taaatgtttc cccaatactt agctaagcaa agaaggaaaa agtgtacttt      540
tattacacag tcagttctgg ataattctag gggaaattct tccattttag aaatctctgc      600
tttcttcttt tctcccagat tcttctcatt aattccctca gtaaatattt gtctgtggca      660
gggtgcagtg ctcgtgcctg taatcccagc acttttggag gctgaggtgg acgaatcacc      720
tgaggtcagg agtttgaaac cagcctggcc atcatggtga aacctcgtct ctactaacag      780
cacaaaaatt agctgggcat ggtggtgcgt gcctgtaatc ccagctactt gggaggctga      840
ggcaggagaa ttgcttgaac caggaggcgg aggttgcagt gagccaagat cacgccactg      900
catgccagcc tgggtgacag agcaagactc tgtctcggaa aaaaaaaaa aaaaaacta       960 tatatacata catacatata tatatatata tatataaaat gtacatatat atttatctgg     1020
cacctactag atgccccagg taccatggta ggcacaggtg tacagtgatg aagagcattt     1080
tcctataaaa tattacccag gctgactcca agttttaata cctcaggtag gaaaaggagg     1140
agagtgttag taaaatgttt gccgttgaat ttcaccagcg taaaacaac attctgggaa      1200 ataattatct gcacttcagt tctttggggt ggtaccggag ggaatcttta caaaggtggt     1260
attaatggag aagaggaagg gaaggatcct tagtgatggg ttgttttttcc aagcacctcg    1320 atctagtgga tttccttttt ttttttttga gatggagttt cgttttttgtc gcccaggctg    1380 gagtgcaatg gcgcgatctc g                                               1401

<210> SEQ ID NO 31
<211> LENGTH: 777
<212> TYPE: DNA
<213> ORGANISM: Homo sapiens
<220> FEATURE:
<223> OTHER INFORMATION: lnc-KIAA0513-2

<400> SEQUENCE: 31
ggcccagggc ggccccgtgt ccatctgcta catctgtggg gctgagctgg gccccgggaa       60
ggagttccag ctcaacgtga accccgccag ccgcttgggc gagaaggagc ccttcttccc      120
cttcctcacc gtgtacccgc ctgcccctcg tgccaggcct gtggactcca ccggcctggt      180
ggctacctgt gtgctctgct accatgacct gctggcccag tggctgcagc atgaggcccg      240
cagctcccac cacgctgtca gcgcctggtc ccggcagtac caggtggaga cgttcgtgtg      300
cttcttttgt cagcaggaga agaaacggtg tctggggctg aagtccgtgc gggtggcccg      360
gctgcccctg ttcctataca ccctgcgagc aagccacagc ctgttggtgg atgacggaca      420
gcagctgatc atcggtgctt gcgtggagtg tgggaccctg gtgtgtgcgg gccaagggct      480
cacccgccaa ggaccatga gctggagctc cccggtggca gcagcgacga agatgaatcg      540
gcgctgtttc cactatgatg cagctcctcc atctctggca gcatctttgt cttggcacct      600
cttttatctg aattattcac atctggacac tgaggtctct gaggttcgga gagggaaagt      660
gacttgccca aggccacaca ggtgtcagct ccaggggcag agtgctccct tctcagccca      720
gctgcacaca ggttttctct actccaacag tcgctttggg gccatgggtc tgagaga       777

<210> SEQ ID NO 32
<211> LENGTH: 1499
<212> TYPE: DNA
<213> ORGANISM: Homo sapiens
<220> FEATURE:
<223> OTHER INFORMATION: lnc-POLR1E-1

<400> SEQUENCE: 32
```

```
gacagacagg ctggtcttgg actcctgacc tcatgatcca cccgccttgg cctcccaagg    60
tgctgggatt acaggtgtga gccaccgtgc ccagcctacc cgtgctttca aaggtcctgt   120
atttccacca ctttgtcacc acagacagcc agaaggtcaa gcagctggcc tccaccttgc   180
ttccttctgg tgcgcatata taggagcctg attagcatgt agaatcctag cagaatggga   240
gtctttgaaa taggtttcag ctcaccagcc tctagttaca ggaggcattc tagaaggaca   300
tgagtggatt ataactgcca accaattgta tgtgccactg aggagatgga gaagctgtgt   360
ccagagcggt gctataagga caggagtgtg acacaggaag gcttaggtac gtggcctggg   420
cccagtctca catctcaggg tcctgcttca agtgggagca gttgagatct gtgacactca   480
gcacctggga ggccgggtca gtgaagggag ggtgcttctc ctgcctcagc ctcccgatta   540
caggcatgca ccaccatgcc cggctaattt tgtatttta gtagagacag cgtttctcca   600
tgttaggctg gtctcaatct cctgacctca ggtgatctgc ccgcctcggt ctcccaaagt   660
gctggaatta taggcgtgag ccaccacgcc cagccttttg tgattacttt taaaattcag   720
ctgggtttga cacttggagg cttaatttct gggaatgact ggacacagca tgtggctggg   780
accctctgaa caacctctga cctagtggaa agcaggtgg taatgactgt aggtatggat   840
agggaaagac taggcgggca atacttgtc gtgtgtcaac aggtgtattt tgctaaatgt   900
cggggacaca ttccaagagg ctaaaaagca aatttctgta cattaggaga tttgtgagtc   960
cttaggaaag gctcagaaga gggctccacc tagcacaata cctgacatag aaagtggtca  1020
gtgtctgcag aatgagtcgg catgaaccgt actttccttg gcagggttat taggtggtaa  1080
atacctgcag aataatggga ttgtactagg gtttcttctg gctttagaaa cccatttgtt  1140
tactaataga ttcccagagg ataccttgat ctcaccaagc tatttgccag aatgtctcct  1200
gatggcctca ttgaagaaag ggggactatg agccagatgc tggtgccctg aagatttgta  1260
gtttgtggga tagtcttaac ttggcagggt ttgattaaca gaatgaagtc tgttccttag  1320
agggaagtct ttgcttgctg ccctgacctg ctggacactg ttaattggga tgaggtcaaa  1380
gaaggcatag ttaccacatt tgcaggagac cctaacctgg aaatagtaaa ttacataaca  1440
ttctttcaag tgtctcctct tttaaaaaag tattttgata tagtttcaca cagagaaaa   1499
```

<210> SEQ ID NO 33
<211> LENGTH: 2108
<212> TYPE: DNA
<213> ORGANISM: Homo sapiens
<220> FEATURE:
<223> OTHER INFORMATION: lnc-B3GAT2-3

<400> SEQUENCE: 33

```
agagttgctg tagaagaagg aaaagagagg aagacaacac aacacaggag gggataagta    60
cctctggaca caatggaagt agtagttgtt gagcagaggg aaagggatag gagaaggatg   120
tggactgcag tgctgcagtg ccaggtaata actttgatca tgtacctcct tggctcaggt   180
gctgtctctt ctactctcct ccttacttgt actaccttat ttagcactta attatatact   240
ttcttgactc actttgagac acactgatta tgtggtctgc ctcaaagaca gaatcctagt   300
tttggatttt agcattactg atctatagcc ttgcaggggc ttaaggatgg cagctgtctc   360
tctcccttgg gatctagctt ttgcaaatat tgaagggaag agatttcttt gatcttatag   420
gaatagatcc acagttcctc tccagatttg cttttataga gaagtgtgtg tcaccaaaac   480
aatggagata cggtcagaga ggcccctacc cccagaattt taatataatt ttactttctg   540
gggcatttat tcttgacaaa tactttctct cctatcagct cacttgttcc tcacaaaaac   600
```

```
cctataagat attaatatta ttaaacagac ccctatgaag cacctcaagt ctttctctct    660
tcccacttcc attcttgcac acctttgct agactagtct ctgcgttcat cacatcaggt    720
ttctaaaata aaagtcccct aataactttc tatttgttct ctcatcatat tgaacctttt    780
ttgcctggct tataaggtgg ccttaaaacc ccattttcct ctaaacattg tctctgtagt    840
tcaggaatat ggcaggctca acactatgct tgagcccata ttgcttccct cattagtgat    900
gcctcctctc agaccaccca gattctactc attcttcaat ttccagcttc ccttggagc    960 cttcccagat cattagcttc ttaaaaatcc cagctttctc tgaattctga tggtagcccc   1020
cgttatttgg acaattatgt cctggtctta aagtcctaat gggaaaaaaa agtacatgat   1080
ggacttcatg tagagaagaa agcactggac tgagttttaa dacagctgct aaggagctgt   1140
gtgagccaaa ccaggttact ttacctctct ggatctatat ttgctgatct gttaagtgga   1200
gacaattggg tcagataatc ttggtggtct ttgcttattc tgaggttctt ggacaacttg   1260
gcctagttca cgtgggatgg gattgaagat cttactgagt tcttggatgg aaatgtcagt   1320
aatgggcact tagtgccttc aggacttgtt ctatactatc ccagaaattt ctgatgctaa   1380
acttggcaat ttttaaatgt catattcctt ttctccaaac tctttaacca caagaattca   1440
gggaaggtta tgggggtga cttagttatc tggataatac atattgtgga caatatagca   1500
ttatccttgg gaatgatttc atattgttga ataaatagga tcaacttctt gataaacctt   1560
agtcccaagc atttcatctt cattggatag tgttacatag taatatattt atgttttctt   1620
ttaatcattt cataacttgg aaaatactaa catagtcaaa actctagggt aggtgataca   1680
tgagtttctg tagtaatctg gttggagaca tgttgtaatt ctgtatatat atgtacattt   1740
atcccatgca tgttatgcct aaactaagac ggatacccct gaattaagag gtgctgttat   1800
acattgacca ggcttaagaa tatctcttta aagtgtgtcg acatttaatt gacctttgga   1860
agttcattct gttaatcata ctcaaagtgc taaagctatg gttgactgct ctggtgtttt   1920
tatattcatt cgtgctttag catataaatt cttcagcata attgctactt atttagcaag   1980
agtttccttt atttgaaaat gtgagttgtg cttgtatttt tgtgtctttc tttctttctt   2040 tctttttta aactttgctt caggctgggt agtggtagag gtttgaatta aaatgttttc   2100
ctgtcagt                                                            2108
```

<210> SEQ ID NO 34
<211> LENGTH: 1184
<212> TYPE: DNA
<213> ORGANISM: Homo sapiens
<220> FEATURE:
<223> OTHER INFORMATION: lnc-MRPS25-1

<400> SEQUENCE: 34

```
gtcgctcacg aggtcgcgcc tcgcacccgc cttcctcctt ttcttttacc ctcccctcca     60 gaaaaacgg cggttgggct cgacggccg ccaaaggcgg actagaagcg gaggggtgaa    120
aatcccggca gagaaggaag aagggactgc aggcgggagg aggaggagga taaggaggaa    180
gggagcccgc ccagccggag ccatctccgt cgagaacaaa atggcggcgc tggcggaggg    240
ccaactataa ggcggggccg cggccattcc ccctccaccc ccaccccttgc gccggccggg    300 ccggtcaggg ggaacccgct cgcttcgccc ggccgcgggc ggggagggga ggggagcggc    360
ccggcccact atgcaaagcg ccgggcgccg ccgccgccac cccgtggcaa aggtcgaggg    420
gttaatgctc tggaagacgg atgaaaaggc actgcccgag aagcggggtg aagacagcgg    480
```

```
gaagctcatg ctcacaggcc gctctgtaac tgaaagaagc cacatggaag ggagaatcca    540
catattggaa aatggtgccc gaacctctgt ttcctccctc catggagtga ataactccct    600
ccagggaaag cggtttcagg catgaaccat ggaccacaga gaagccactg gagcctgggg    660
agaagccacc aggccacttg gaagaaggca agtggtcccc aggttacctc tcatcaggcc    720
cgggacagcc ctgccccgct tcttcagctc cccgaagcag ccgtcgcaga ccttggccat    780
cctgtccttc agcaacagaa ttggctgagt aatgtggaat gtggccagga gaccagccag    840
atgcagagcc cagtgagccc tgccctgcgt ctctgtgcag ggtgtgtgat gtgtggcttc    900
ccagacagtc atccaacagg cactttccaa gtccctgctc tgcaccaggg agggcttcct    960
gagtggcaag agctacgcct gggctgggtg ccagctagct gggtgaagtt ctcacagtgt   1020
ccactagatg ccgcgcctac accacagggt ctcactatgt tgcccaggct ggtcccaaac   1080
tcctggcctc aagtaatcct tcagcctcag cctcccagat tgatggaatt acaggtataa   1140
gccaccatgc cccacctaat aaatgatttt aatgagaaaa tgca                    1184
```

<210> SEQ ID NO 35
<211> LENGTH: 914
<212> TYPE: DNA
<213> ORGANISM: Homo sapiens
<220> FEATURE:
<223> OTHER INFORMATION: lnc-ANKRD12-1

<400> SEQUENCE: 35

```
ggcccgccat gttcttctcc gcggcgctcc gggcccgggc ggctggcctc accgccact     60 ggggaagaca tgtaaggaat ttgcataaga cagttatgca aaatggagct ggaggagctt    120
tatttgtgca cagagatact cctgagaata accctgatac tccatttgat ttcacaccag    180
aaaactataa gaggatagag gcaattgtaa aaaactatcc agaaggccat aaagcagcag    240
ctgttcttcc agtcctggat ttagcccaaa ggcagaatgg gtggttgccc atctctgcta    300
tgaacaaggt tgcagaagtt ttacaagtac ctccaatgag agtatatgaa gtagcaactt    360
tttatacaat gtataatcga aagccagttg aaagtatca cattcaggtc tgcactacta    420
caccctgcat gcttcgaaac tctgacagca tactggaggc cattcagaaa aagcttggaa    480
taaaggttgg ggagactaca cctgacaaac ttttcactct tatagaagtg aatgtttag    540 gggcctgtgt gaacgcacca atggttcaaa taaatgacaa ttactatgag gatttgacag    600
ctaaggatat tgaagaaatt attgatgagc tcaaggctgg caaaatccca aaaccagggc    660
caaggagtgg acgcttctct tgtgagccag ctggaggtct tacctctttg actgaaccac    720
ccaagggacc tggatttggt gtacaagcag gcctttaatt tatattgaac tatccaggat    780
gagaagactg ataaaagaag aagctagctg aacagctgta aaatgcccaa atctgggttc    840
acaaaaccaa ttcagagtga aaattctgac agtgacagca atatggtaga gaaaccatat    900
ggaagaaagg tata                                                     914
```

<210> SEQ ID NO 36
<211> LENGTH: 1153
<212> TYPE: DNA
<213> ORGANISM: Homo sapiens
<220> FEATURE:
<223> OTHER INFORMATION: lnc-GJA10-3

<400> SEQUENCE: 36

```
gggcagaaag gaaccgggtt gtcttgggcc gggcagggcg ggtggtgact ctcaaaagga     60
aataggatca tggcagcaga tgatgacaat ggtgatggaa caagtttatt tgatgtcttt    120
```

```
tctgcttctc ctcttaagaa caatgatgaa ggctcactgg acatatacgc tgggttggac      180
agtgctgttt ctgacagcgc ttccaaatcc tgtgtaccat caagaaattg tttggactta      240
tatgaagaga tcctgactga agaaggaact gcaaaggagg caacatataa tgatttgcaa      300
gtagaatatg gaaaatgtca actacaaatg aaagagctga tgaaaaaatt taagaaata       360 cagacacaga atttcagctt aataaacgaa aaccagtctc ttaagaagaa tatttcagca      420
cttatcaaaa ctgccagagt ggaaataaac cgcaaggatg aagaaataag taatcttcac      480
caaagattgt ctgagtttcc acattttcga aataatcata aaactgcaag acatttgat       540 acagttaaaa caaagatct taaatctaga tctccacatt tggatgattg ttcaaagact       600
gatcacagag ctaaaagtga tgttctaaa gatgtacatc atagcacttc actgccaaat       660
ctggaaaagg aaggaaaacc acattctgat aaaaggagta cttcacattt acctacatct      720
gttgagaaac actgcactaa tggtgtttgg tcacgttctc attatcaggt tggcgagggt      780
agctcaaatg aggatagtag aagaggaaga aaagatatta gacatagcca gtttaacaga      840
ggaactgaaa gagtacgaaa agacttaagt actggctgtg gtgatggtga accaaggata      900
ttggaggcta gtcaaaggct acaaggacat cctgagaaat atggtaaagg tgaaccaaag      960
actgaaagca aaagttcgaa gtttaaaagt aactcagatt ctgactataa aggtgaacgc     1020
attaactctt cttgggagaa agagacccct ggagaaaggt cacacagtcg agtagactct     1080
caaagtgaca aaaaactaga aagacaaagt gaaagatcac aaaatataaa taggaaagaa     1140
gttaaatcac aag                                                          1153

<210> SEQ ID NO 37
<211> LENGTH: 542
<212> TYPE: DNA
<213> ORGANISM: Homo sapiens
<220> FEATURE:
<223> OTHER INFORMATION: lnc-SERPINC1-1

<400> SEQUENCE: 37
cttttcgagg taggagtcga ctcctgtgag gtatggtgct gggtgcagat gcagtgtggc        60
tctggatagc accttatgga cagttgtgtc cccaaggaag gatgagaata gctactgaag      120
tcctaaagag caagcctaac tcaagccatt ggcacacagg cattagacag aaagctggaa      180
gttgaaatgg tggagtccaa cttgcctgga ccagcttaat ggttctgctc ctggtaacgt      240
ttttatccat ggatgacttg cttgggactc agaattcatg attgaagaaa tgcaggcaga      300
cctgttatcc taaactaggg tttttaatga ccacaacaag caagcatgca gcttactgct      360
tgaaagggtc ttgcctcacc caagctagag tgcagtggcc tttgaagctt actacagcct      420
caaacttctg ggctcaagtg atcctcagcc tcccagtggt ctttgtagac tgcctgatgg      480
agtctcatgg cacaagaaga ttaaaacagt gtctccaatt ttaataaatt tttgcaatcc      540
at                                                                      542

<210> SEQ ID NO 38
<211> LENGTH: 2475
<212> TYPE: DNA
<213> ORGANISM: Homo sapiens
<220> FEATURE:
<223> OTHER INFORMATION: lnc-C9orf69-1

<400> SEQUENCE: 38
gacgccggcg ccgccgcgga gagggcaccg ggccgacgcc tcccccagg gtcagctgcg        60
```

-continued

| | | | |
|---|---|---|---|
| ggctcccagg cctaggcgcc catgaccoct acgccaacag ccgcctggac accgccgccg | 120 |
| ccactgcgac ctagcgccgc cgccgccggg gcccaatgcc ggtcatgccc attccgcggc | 180 |
| gggtgcgctc cttccacggc ccgcacacca cctgcctgca tgcggcctgc gggcccgtgc | 240 |
| gcgcctccca cctggcccgc accaagtaca acaacttcga cgtgtacatc aagacgcgct | 300 |
| ggctgtacgg cttcatccgc ttcctactct actttagctg cagcctgttc actgcggcgc | 360 |
| tctggggtgc gctggccgcc ctcttctgcc tacagtacct gggcgttcgc gtcctgctgc | 420 |
| gcttccagcg caagctgtcg gtgctgctgc tgctgctggg ccgccggcgc gtggacttcc | 480 |
| gcctggtgaa cgagctgctc gtctatggca tccacgtcac catgctgctg gtcgggggcc | 540 |
| tgggctggtg cttcatggtc ttcgtggaca tgtgagggcc gtgggtgcga gcttgatgta | 600 |
| tcgtcccggc ctgtggctgt gttctctcca tgggtgggt cggccagcgc cttcccttcg | 660 |
| cccatcccc aggcagtcgc tgctgcccgg cgcccacgga gagaaagaa agggctgaga | 720 |
| cttctgtgat gggggcgcgg acaccacccc taggctggct tcctggaccc accctccccg | 780 |
| tatgcactct caggggcagc gcccacctgc cggtggctcc tgctcacatg tcttcgggtc | 840 |
| gtactgcggg gtgggccctc cgttccgcct ctctgtgggc ctctctccag gaccacagct | 900 |
| gccagggact ttagacatca ccctgggagg cccctggaca cagagggctg tgtgcccagg | 960 |
| agcaattccg gaggggggcc ctcctggctg cacagcccct tctgcgtgcc ctggccccag | 1020 |
| ccccagccaa cgggacacgg aaggctcccc tcgctgacac accacactgc cacaaagctg | 1080 |
| cttactctgc cctgggccgc ctgaggcctg gcactgcccg cggaccaccc tgtgtgtgtc | 1140 |
| atcctgaggg gctgtgtggg tcctgagtcc ccagccagcc ttcagggtcc ccttggattg | 1200 |
| tgtagatgca gtctagcggg gggccggaga agggctcagg tgggaggggc ctcagcaggc | 1260 |
| tcccagctca ggggctggcc tggggggaac cctgggagcc aggggctgac tccagcaaca | 1320 |
| ctggcctgtc tgcctgttct gggagggctg tgaggatgtc ttgcagatgc tctggatttc | 1380 |
| tgcggaggca cctccattcc tttctggctt ttttgcggg ggagggcttt gggcctcttt | 1440 |
| ctttgaggga acaccgtcaa agaaagcctg ggagatcgag gcttcagtga ccaggatgg | 1500 |
| aaacgcgtgt cccaagtgtc cggagcaggc ggcagaggcc tcagtgcggc aaacacagcc | 1560 |
| ccagagcctg tgtggcacca gcagcatctt agagcccag gtatatgctg agatcttatc | 1620 |
| tcacgctgtc ctccagtgtc tgggggcccc aaatgatggc acaggggcag gtgggctgga | 1680 |
| ggggcgcaga tgcctgtgtt cagggagggt ggccaccatg ggccgaggtc tcacccagga | 1740 |
| cccccttgctc tgctcctcag ccttgcagtc acggcagcac tatggtggac tgcccatggc | 1800 |
| cgtgtgactt tgggggcaag tgggagggcg ccctgaataa tgattgcaag gacaacaggc | 1860 |
| agaggctacc ctagagcagg acacaggtg tggtactgac aaccctagtg tcacctcaaa | 1920 |
| tccatgtccc cacactctgg gcatgggtgg gacttgtgac cctaccctgt caggcggacc | 1980 |
| agtggcccag gagccatgag gacagttgtg tgccactgga agagaaactt tttgaaaaac | 2040 |
| cctaaatcag gtagagaaag caaaaaatct ctggccgtaa accgtgctct ctaatttatc | 2100 |
| ggcagcttct gtggatgacc tctgatgagc ccgggctgcg tccacgccct gggcaggtag | 2160 |
| gcgggagctt ccctgcgtgg gcctcatttc ttgctgcaga gaatcttttg cactaagtca | 2220 |
| tgctgtttcc tcaaagaagc tttgtttttt gttaacgtat tactcagagt cacccaagcc | 2280 |
| tcttggctga gggtgaaggt gggacggag gcgggagggg gctggtggtg ccgctcgtgc | 2340 |
| ggtgtcaacg ctgcagggag ttgtggcacc ttggtgccct ctgagcacct ggccgcctgc | 2400 |
| tgtccccggt gcctgtgaaa ttcgtcatgc catgacccac ctgcattaaa cctatttttt | 2460 |

-continued taatgtgttg atgga                                                    2475

<210> SEQ ID NO 39
<211> LENGTH: 2517
<212> TYPE: DNA
<213> ORGANISM: Homo sapiens
<220> FEATURE:
<223> OTHER INFORMATION: lnc-SEBOX-2

<400> SEQUENCE: 39

```
ccggtggaag ccgctctgtg cggcggccgg agctggagcc ttctcgccag cgtcgaccac    60
gacgacgcgg aggcacctct cgtcccgaaa ccgaccagag ggcaaagtgt tggagacagt   120
tggtgtgttt gaggtgccaa acagaatgg aaaatatgag accgggcagc ttttccttca    180
tagcatttt ggctaccgag gtgtcgtcct gtttccctgg caggccagac tgtatgaccg    240
ggatgtggct tctgcagctc cagaaaaagc agagaaccct gctggccatg gctccaagga   300
ggtgaaaggc aaaactcaca cttactatca ggtgctgatt gatgctcgtg actgcccaca   360
tatatctcag agatctcaga cagaagctgt gaccttcttg gctaaccatg atgacagtcg   420
ggccctctat gccatcccag gcttggacta tgtcagccat gaagacatcc tcccctacac   480
ctccactgat caggttccca tccaacatga actctttgaa agatttcttc tgtatgacca   540
gacaaaagca cctccttttg tggctcggga gacgctaagg gcctggcaag agaagaatca   600
cccctggctg gagctctccg atgttcatcg ggaaacaact gagaacatac gtgtcactgt   660
catcccttc tacatgggca tgagggaagc ccagaattcc cacgtgtact ggtggcgcta   720
ctgtatccgt ttggagaacc ttgacagtga tgtggtacag ctccgggagc ggcactggag   780
gatattcagt ctctctggca ccttggagac agtgcgaggc cgaggggtag tgggcaggga   840
accagtgtta tccaaggagc agcctgcgtt ccagtatagc agccacgtct cgctgcaggc   900
ttccagtggg cacatgtggg gcacgttccg ctttgaaaga cctgatggct cccactttga   960
tgttcggatt cctcccttct ccctggaaag caataaagat gagaagacac caccctcagg  1020
ccttcactgg taggccagct gaggccccaa gtgcccaggc ttggtcaccg ggaagaacaa  1080
ctctcatccc acaattgctg cagaactctt ctctccccat catgggccac agtgggtctc  1140
ttaatttgat tgtggggttc ttttttgtggg gaggggtggt ataacttttc ttcagaagac  1200
ccatgtggga cacctccaag gctggcctcc tcataagccc tgcctacacc atgttccagt  1260
aaacctctcc accaaggaac tgtgttcagc tgccacaggc ctggaggagt ttcctggcct  1320
gtcacgtgag gtttgatcag taaaccagtg cacgcttggc cacccttgcc atttctgctc  1380
ccagagtctc aggctcccct tctgacccag tgtgcgccct tgactgcttt ctttgctgcc  1440
cttccaggga gctgccccc tggtaggca tgtgcctgtt tccctctcag cctggaggct  1500
ggctggacat tcctaggggt cactgtgcct ctcagctagt tggcgggggt gctggactgg  1560
actcttgttc actttacctt ctgccaaatg cagagaggga ggccagtgtc agggtcggag  1620
tggcctggct cttagcactg accgaccatt gccatttctg gcctcgctag gcccaggaga  1680
ggagggaggc aagccagtcg ggtttcctgg agcaatgggt gtgccagccc tcagcatgac  1740
tctgccaagc atccagacca caaatgcagg aatttggctg aggagcagct ttaggtatgg  1800
attgatgact aagtcaagct acttcctgag cttctctcag atttccaaga gccagagatg  1860
aattgtgctg catcttgccc caattcttag gattctttt cctccgccac tgcagtgatt  1920
gttagaggta gttttcttga attaatatta aatcacagtt ccagcccttg ttattcttgt  1980
```

| cctttagtcct | ccaggggag | ctggggttgc | agggcaacag | tacagtcgcg | cttacgacct | 2040 |
| ggctagaaca | caaggtcaga | tgataaacag | aagcacagga | actcagccca | tggccgcaag | 2100 |
| ctggtcaagg | cctgctcact | gtaaacatgg | ctctgtacca | ttgagtttaa | cacaatttta | 2160 |
| ttagaaatta | gtgtttgctt | ccatcactta | tgctgagcaa | ccaaatatta | cagttatgtg | 2220 |
| ataaaggaaa | aattctttcc | tgcccaggac | ctgcgccatc | ctttaggccg | accttggtca | 2280 |
| cataccaaat | tcaataaaac | ccaatactgg | cctgtgttgt | aacagcagg | ctgccaggtt | 2340 |
| tctcagaaac | tgacaagaaa | atctgacctt | catccatact | ttgtttactt | accctgggc | 2400 |
| tgcttggagt | tgaaaaatgc | acacagccaa | gagttgcttt | ctgaataggg | ctggaaactt | 2460 |
| tcaaagaaaa | cccccaaact | tttaagtcac | aaagtctgat | taaagaagct | aagatca | 2517 |

<210> SEQ ID NO 40
<211> LENGTH: 703
<212> TYPE: DNA
<213> ORGANISM: Homo sapiens
<220> FEATURE:
<223> OTHER INFORMATION: lnc-AKR1C2-4

<400> SEQUENCE: 40

| taaacattaa | gtatctacat | tcactaaaag | tagttctgaa | tgaatgttat | ttaatggtgc | 60 |
| caatgatgtt | ggaggatacc | tgtgcatctc | atgctgtggt | tacagcatca | attgtgatga | 120 |
| atataggata | ctgagtccct | cctagaaatg | acttcaggaa | cttcaccccc | caactccaca | 180 |
| atctgggaat | ggcagacaga | ttcagcacca | ggagaacatc | acataaagga | caagtgtgta | 240 |
| tgtttaaaaa | tggcaagttt | cggcctggca | tggtggctca | cgtctataat | cccagcactt | 300 |
| tgggaggctg | agtctaagtg | tacagtgctt | gtaaagtctg | cagtagcata | cagtaatgtc | 360 |
| caaggctttc | acatccactc | accactcgct | cactgaccca | gccagagcaa | cttccagtcc | 420 |
| tgaaagctgc | attcatgtat | agtttgaggg | tatccagcct | cagattatct | gaggatgtag | 480 |
| ctcaagattt | cctaattttg | caaacagcaa | gcttcccagg | agattcttag | attcctgcta | 540 |
| acaaaaggcg | gagactcact | ggacagttac | tgaagataga | cagtaggggg | cggaagggcc | 600 |
| cacgcttctt | tgatattggt | ggcttttggtt | tttcagtgac | ggggacact | ttgacttcag | 660 |
| actcaatcac | cacaattgca | atcaaaagac | ggctttagtt | gga | | 703 |

<210> SEQ ID NO 41
<211> LENGTH: 2652
<212> TYPE: DNA
<213> ORGANISM: Homo sapiens
<220> FEATURE:
<223> OTHER INFORMATION: lnc-SAMD14-2

<400> SEQUENCE: 41

| ggattacgat | cgtcgcaacg | aggatgtgga | tcccatggca | gcctctgctg | agtacgagct | 60 |
| ggagaagcgt | gtggagaggt | tggagctgtt | ccctgtggag | ctggagaagg | actccgaggg | 120 |
| cctgggcatc | agcatcatcg | gcatgggcgc | cggggcagac | atgggcctgg | agaagctggg | 180 |
| tatcttcgtc | aagaccgtga | cggagggtgg | tgcggcccat | cgggatggca | ggatccaggt | 240 |
| gaatgatctc | ctggtggagg | tggatggaac | aagtctggtg | ggagtgaccc | agagcttcgc | 300 |
| ggcgtctgtg | ctccggaaca | ccaagggccg | agtgcggttt | atgattggcc | gggagcggcc | 360 |
| gggagagcag | agcgaagtgg | cccagctaat | tcagcagact | ttggaacagg | agcgatggca | 420 |
| gcgggagatg | atggagcaga | gatacgccca | gtatggggag | gatgacgagg | agacgggaga | 480 |
| gtatgccact | gacgaggatg | aggagctgag | ccccacgttc | ccgggtggtg | agatggccat | 540 |

```
cgaggtgttt gagctagcgg agaacgagga tgcactgtcc cctgtggaca tggagcccga    600
gaagctggtg cacaagttca aggagctcca gatcaagcat gcggtcactg aggcagagat    660
ccagcagctg aaaagaaagc tgcagagcct ggagcaggag aaggggcgct ggcgggtgga    720
gaaggcgcag ttggagcaga gtgtggagga gaacaaggag cgcatggaga actggaagg     780
ctactggggt gaggcccaga gcctgtgcca ggctgtggac gagcacctgc gggagactca    840
ggcgcagtac caggccctgg agcgcaagta cagcaaggcc aagcgcctca tcaaggacta    900
ccagcagaag gagatcgagt tcctgaaaaa ggagactgca cagcgtcggg ttctggagga    960
gtcggagctg ccagaaaagg aggagatgga caagctcctg acaagatct cagaactgga    1020
aggaaacttg caaacactga ggaattccaa ttctacttaa caggaatcat ccatgactg     1080
gacataatt aaccccccctc ccattgttcc tccctcccct gtcctcaaca ccccacccct    1140
cccccttcca gcctggggac aggtgccccg actccccca ccctccacc ccacctcccc      1200
cagcttcagg gaccagaggg ctcatatcac aggccccctt aagatggcct gggcagacag    1260
aggtggctag aagggcagcc tctttcttgc cccatggggc tgaggcacag aggccgaggg    1320
ctgccgaggg ctggcctggt ggtcgacgga cacaagcacc tgcagatcaa actgccagac    1380
tttacacact ccagctttg tctctggact ggaacggggc tggggctctc ccagcatctg     1440
ccaactgggg gctgctccct gcccatgggg cacctgggtg gcccctgggc ctcttgactt    1500
gagattctac cttctcggcc cttccctctc ccccatcat tgtgccgtct ctgttgcatt     1560
ctgacccttcc cgcctggggg gtgggggcgt tgcctcaaca cctcccccat ccctgttccc   1620
tgtcctggga gggatagagt ccacccccaga gcccggaggc tgggcctggc cctggccctg   1680
cactgatttc tcatgtgtcc ttcgggaaaa gggggagtga gagtgggaaa aagggagagt    1740
tcaggacacc tggtccccag ctccccattg cctggggcag cagccctcaa tttctccttg    1800
tgcctcccct cttccaggtg ccaaatagcc ataacctcgt cttggaactg ttatgtggcc    1860
tctctggggt ccaggtttcc tggtcaagcc tgggaatgcc agggaggaaa gggggtctgg    1920
ctacagcgac cctggtctta ggcaagggga acatttctcc ctggagagtc aggtcctatc    1980
ctgtgctgcc ctgtctgccc agcccagggc gatgcctgga agcctactga cattgcaggg    2040
agtcagcctc gcccccaccc cctactggtt ttccaatgtt ttgactggag ggcaaaattt    2100
tactactact catcttttg gagaccaggg ctgcctgct ggcagcctgc cttctaagtg     2160
aaatcgactc tgtttcccca ctttaacccc aaattggggc ttggaccaag ggaggtgaga    2220
ccacctcccc caggtcccct ccccttcaa aatccatctc attttgccac ttcatgcccc    2280
tgccctaact gggttttgt tcatttttta aaaacagacc acccatccca tccgttttgg     2340
cttcttgtcc cctgtaaata gaccatgact tcgatcagta tttcttgtcc ccaccccttc    2400
ctatccccag atgtgccccc atccctgaa ggagctggct gtctcagtcc tgggctcgcg    2460
cacttcaccc cggcagatgg aggggcgga accgggtggg cggggccgct cgggctgct     2520
tgggccagcg gccacccctg cccagccgtc gggagggccg catctctgta tataatatat    2580
atatgtatgt attgttcccg gttttgtacg gaccatgccc tctgtcaggt cgtccccata    2640
aaagcagccc cc                                                         2652
```

<210> SEQ ID NO 42
<211> LENGTH: 629
<212> TYPE: DNA
<213> ORGANISM: Homo sapiens
<220> FEATURE:

<223> OTHER INFORMATION: lnc-WDR74-1

<400> SEQUENCE: 42

```
tttttctact gctcgtggat ttacgcgcac gttggaaccg aagagagctc tgttgttgca      60
atgttcagcc cacaagagct tactggtgaa ggaatgggac aagacccatc tttatgcaaa     120
gccagcgtta cagtaatgtt ccaggtattc ctgatgacag tctgcctcta tcttacagag     180
cagcttgttg ctatatacca ttgaaaagcc ttcagagctg agaggtacta ctaaccaata     240
acctgcttgg ctcaaagggc cagcaccttc tctctaaagc ccaagaggag tttgaggaaa     300
actaggtgtc tgtgttcact ccaggctgaa gttacaggtg agcactgtat agatgaccac     360
tttcgtaaac tactgaccta gcttgttgcc aattgttgat tgaacttccc ataactccac     420
ttcgtgtctg ttcctctgta tacagccacc ttctgttccc gtcatgagcc tttaggtctc     480
catttgcata ttgcaaatac tatgttccat gtaggtagct cattcagggc cttgctcttc     540
acttcaaaaa aggttccctt gaggactggc tgtcaatttg tgttgctgtg ttggttgttg     600
atgaaaataa taaaatgatt gattacata                                       629
```

<210> SEQ ID NO 43
<211> LENGTH: 236
<212> TYPE: DNA
<213> ORGANISM: Homo sapiens
<220> FEATURE:
<223> OTHER INFORMATION: shared exon sequence of all DSCAM-1 isoforms

<400> SEQUENCE: 43

```
gtgaggtcac ctgtagaggt catgctgcgg agtcccgagt ccctgattat attcaagacg      60
tggagctctc tttttcccgt cctgctttct ttccagaagt gcctcagatg catcctcccc     120
ttctcttttc tccacatgaa gacgtcactg accatcttct ctggtttgct ttccaacacc     180
gagcaccaag tgcttcaaag gtcatggtgc cctggggccg agagctactt atgtgg         236
```

<210> SEQ ID NO 44
<211> LENGTH: 75
<212> TYPE: DNA
<213> ORGANISM: Homo sapiens
<220> FEATURE:
<223> OTHER INFORMATION: shared exon sequence of DSCAM-1 isoforms 2 and
      3

<400> SEQUENCE: 44

```
gctgaaaccc ctgaaaacaa tcgtaggacg atgacaaggt tttggcagct gcaatcttaa      60
agaccaggaa gtgag                                                       75
```

<210> SEQ ID NO 45
<211> LENGTH: 20
<212> TYPE: DNA
<213> ORGANISM: Artificial Sequence
<220> FEATURE:
<223> OTHER INFORMATION: LINC00323-001 forward

<400> SEQUENCE: 45

```
tccgtgaaat gaatccatca                                                  20
```

<210> SEQ ID NO 46
<211> LENGTH: 20
<212> TYPE: DNA
<213> ORGANISM: Artificial Sequence
<220> FEATURE:
<223> OTHER INFORMATION: LINC00323-001 reverse

```
<400> SEQUENCE: 46
tccattccag tggagacaca                                              20

<210> SEQ ID NO 47
<211> LENGTH: 22
<212> TYPE: DNA
<213> ORGANISM: Artificial Sequence
<220> FEATURE:
<223> OTHER INFORMATION: LINC00323-002 forward

<400> SEQUENCE: 47
aagaccagga agtgaggtga gg                                           22

<210> SEQ ID NO 48
<211> LENGTH: 22
<212> TYPE: DNA
<213> ORGANISM: Artificial Sequence
<220> FEATURE:
<223> OTHER INFORMATION: LINC00323-002 reverse

<400> SEQUENCE: 48
gctcggtgtt ggaaagcaaa cc                                           22

<210> SEQ ID NO 49
<211> LENGTH: 20
<212> TYPE: DNA
<213> ORGANISM: Artificial Sequence
<220> FEATURE:
<223> OTHER INFORMATION: LINC00323-003 forward

<400> SEQUENCE: 49
taggcttagg gcatgaggag                                              20

<210> SEQ ID NO 50
<211> LENGTH: 20
<212> TYPE: DNA
<213> ORGANISM: Artificial Sequence
<220> FEATURE:
<223> OTHER INFORMATION: LINC00323-003 reverse

<400> SEQUENCE: 50
aaaagagaag gggaggatgc                                              20

<210> SEQ ID NO 51
<211> LENGTH: 20
<212> TYPE: DNA
<213> ORGANISM: Artificial Sequence
<220> FEATURE:
<223> OTHER INFORMATION: PLAC1-1 forward

<400> SEQUENCE: 51
aggtagaagg tggggtctgc                                              20

<210> SEQ ID NO 52
<211> LENGTH: 18
<212> TYPE: DNA
<213> ORGANISM: Artificial Sequence
<220> FEATURE:
<223> OTHER INFORMATION: PLAC1-1 reverse

<400> SEQUENCE: 52
actggaggaa gccggatg                                                18
```

LNCRNAS FOR THERAPY AND DIAGNOSIS OF ANGIOGENESIS

CROSS REFERENCE TO RELATED APPLICATIONS

This application is a U.S. National Phase of International Patent Application PCT/EP2015/058709, filed Apr. 22, 2015, which claims priority to European Patent Application No. 14165398.0, filed Apr. 22, 2014, the contents of each are hereby incorporated by reference in their entireties.

The present invention relates to a pharmaceutical composition comprising (i) a compound promoting the expression and/or the activity of one or more long non-coding RNAs (lncRNAs) selected from SEQ ID NOs 1 to 22, preferably selected from SEQ ID NOs 1 to 3 and 14; and/or (ii) a compound inhibiting the expression and/or the activity of one or more lncRNAs selected from SEQ ID NOs 23 to 42. The present invention also relates to a pharmaceutical composition comprising (i) a compound promoting the expression and/or the activity of one or more lncRNAs selected from SEQ ID NOs 23 to 42; and/or (ii) a compound inhibiting the expression and/or the activity of one or more long non-coding RNAs (lncRNAs) selected from SEQ ID NOs 1 to 22, preferably selected from SEQ ID NOs 1 to 3 and 14.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The era of non-coding RNA (ncRNA) research has been set after publishing the encyclopedia of DNA elements (ENCODE) in 2013. In fact, the majority of the genome is non-coding. The different classes of non-coding RNA comprise small microRNA (miR) and long non-coding RNA (lncRNA). To date, great effort has been taken to understand microRNA-dependent molecular mechanisms and to develop innovative therapeutic strategies. For lncRNA biology, however, very little is known. Next to well-studied miRs, lncRNAs are now in focus of different scientific disciplines.

In cancer research, the lncRNA HOTAIR has been characterized to be an oncogenic factor (Nakagawa et al., Biochem Biophys Res Comm, 2013; Kim et al., Oncogene, 2013). For example during lung cancer, HOTAIR is upregulated in patients (Nakagawa et al., Biochem Biophys Res Comm, 2013). Furthermore, asscociation of HOTAIR with Polycomb Repressor Complex 2 (PRC2) also drives pancreatic tumor expansion (Kim et al., Oncogene, 2013). In contrast, loss of XIST triggers blood cancer indicating that XIST potently inhibits cellular malformation (Yildirim et al., Cell, 2013). At a more mechanistical view, lncRNA-dependent regulation of translation has been demonstrated in breast cancer setting (Gumireddy et al., EMBO J, 2013).

The role of lncRNA Fendrr has recently been discovered and highlights the importance of lncRNA abundancy during cardiac development (Grote et al., Dev Cell, 2013; Grote and Herrmann RNA Biol, 2013). Loss of Fendrr also causes embryonal death emphasizing the crucial regulatory capacity of lncRNA. Another lncRNA termed "Braveheart" is going along with this observation (Klattenhoff et al., Cell, 2013). This is an additional activator for cardiac lineage commitment where mechanistic aspects have been deciphered. Angiotensin II (Ang II)-induced expression of lncRNA has also been investigated (Leung et al., Circ Res, 2013). Interestingly, loss of a single lncRNA reduced proliferative potential of smooth muscle cells (SMCs) and indicated participation of lncRNA for SMC-associated disease. Of great interest, non-coding ANRIL and coding gene CDKN2B could be linked in a longer study investigating leukocyte and platelet content in heart failure patients (Johnson et al., Circulation 2013).

However, the role of lncRNAs in angiogenic signalling is yet vastly unexplored. Angiogenesis is a central physiological process that establishes blood supply and oxygen supply to tissues, thereby enabling the growth and maintenance of nascent bodily structures. During angiogenesis, either pro- or anti-angiogenic signalling guides endothelial cells to sustain vascular integrity. Angiogenesis is necessary for wound healing, as well as recovery from ischemic insults. In such cases, it is beneficial to promote angiogenesis (Bahatia (2013), Mechanical and Chemical Signaling in Angiogenesis, Studies in Mechanobiology, Tissue Engineering and Biomaterials; 12(261-278)). Endothelial cell (EC) performance is of utmost importance for angiogenic signalling especially after hypoxic intervention (i.e. ischemia), e.g. myocardial infarction (MI). So far, to the best knowledge of the inventors nothing is known for the role of specific lncRNAs in ECs. On the other hand, angiogenesis is undesirable and pathological in the context of cancerous tumors, as well as diabetic retinopathy. In these cases, it is preferable to inhibit angiogenesis (Bahatia (2013), Mechanical and Chemical Signaling in Angiogenesis, Studies in Mechanobiology, Tissue Engineering and Biomaterials; 12(261-278)). Anti-angiogenic therapy is an established anti-cancer strategy that targets new blood vessels that grow to provide oxygen and nutrients to actively proliferating tumor cells (Kubota (2012); Keio J Med.; 61(2):47-56).

Currently, the most established approach for influencing angiogenesis is targeting the vascular endothelial growth factor (VEGF) pathway. As is evident from the above, there is, though, an ongoing need for further therapeutic pro-angiogenic and anti-angiogenic approaches. This need is addressed by the present invention. It was surprisingly found that specific lncRNAs are involved in angiogenic signalling and therefore can be used in novel therapeutic pro-angiogenic and anti-angiogenic approaches.

Accordingly, the present invention relates in a first aspect to a pharmaceutical composition comprising (i) a compound promoting the expression and/or the activity of one or more long non-coding RNAs (lncRNAs) selected from SEQ ID NOs 1 to 22, preferably selected from SEQ ID NOs 1 to 3 and 14; and/or (ii) a compound inhibiting the expression and/or the activity of one or more lncRNAs selected from SEQ ID NOs 23 to 42.

In accordance with the present invention, the term "pharmaceutical composition" relates to a composition for administration to a patient, preferably a human patient. The pharmaceutical composition of the invention comprises the compounds recited above. It may, optionally, comprise further molecules capable of altering the characteristics of the compounds of the invention thereby, for example, stabilizing, modulating and/or activating their function. The composition may be in solid, liquid or gaseous form and may be, inter alia, in the form of (a) powder(s), (a) tablet(s), (a) solution(s) or (an) aerosol(s). The pharmaceutical composition of the present invention may, optionally and additionally, comprise a pharmaceutically acceptable carrier or excipient. Examples of suitable pharmaceutical carriers and excipients are well known in the art and include phosphate buffered saline solutions, water, emulsions, such as oil/water emulsions, various types of wetting agents, sterile solutions, organic solvents including DMSO etc. Compositions comprising such carriers or excipients can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgement of the ordinary clinician or physician. Generally, the regimen as a regular administration of the pharmaceutical composition should be in the range of 1 μg to 5 g units per day. However, a more preferred dosage might be in the range of 0.01 mg to 100 mg, even more preferably 0.01 mg to 50 mg and most preferably 0.01 mg to 10 mg per day.

Furthermore, if for example said compound is an nucleic acid sequence, such as an siRNA, the total pharmaceutically effective amount of pharmaceutical composition administered will typically be less than about 75 mg per kg of body weight, such as for example less than about 70, 60, 50, 40, 30, 20, 10, 5, 2, 1, 0.5, 0.1, 0.05, 0.01, 0.005, 0.001, or 0.0005 mg per kg of body weight. More preferably, the amount will be less than 2000 nmol of nucleic acid sequence (e.g., about $4.4 \times 10^{16}$ copies) per kg of body weight, such as for example less than 1500, 750, 300, 150, 75, 15, 7.5, 1.5, 0.75, 0.15, 0.075, 0.015, 0.0075, 0.0015, 0.00075 or 0.00015 nmol of iRNA agent per kg of body weight.

The length of treatment needed to observe changes and the interval following treatment for responses to occur vary depending on the desired effect. The particular amounts may be determined by conventional tests which are well known to the person skilled in the art.

Pharmaceutical compositions of the invention preferably comprise a pharmaceutically acceptable carrier or excipient. By "pharmaceutically acceptable carrier or excipient" is meant a non-toxic solid, semisolid or liquid filler, diluent, encapsulating material or formulation auxiliary of any type (see also Handbook of Pharmaceutical Excipients 6ed. 2010, Published by the Pharmaceutical Press). The pharmaceutical composition may be administered, for example, orally, parenterally, such as subcutaneously, intravenously, intramuscularly, intraperitoneally, intrathecally, transdermally, transmucosally, subdurally, locally or topically via iontophoresis, sublingually, by inhalation spray, aerosol or rectally and the like in dosage unit formulations optionally comprising conventional pharmaceutically acceptable carriers or excipients.

The term "ncRNA" or "non-coding RNA" as used herein designates a functional RNA molecule that is not translated into a protein. The DNA sequence from which a non-coding RNA is transcribed is often called in the art an RNA gene. The term "lncRNA" or "long non-coding RNA" is commonly used in the art and designates an ncRNA comprising more than 200 nucleotides. SEQ ID NOs 1 to 22 and 23 to 42 comprise sequences ranging from 349 to 2517 nucleotides.

The compounds of the invention may be formulated as vesicles, such as liposomes. Liposomes have attracted great interest because of their specificity and the duration of action they offer from the standpoint of drug delivery. Liposomal delivery systems have been used to effectively deliver nucleic acids, such as siRNA in vivo into cells (Zimmermann et al. (2006) Nature, 441:111-114). Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are phagocytosed by macrophages and other cells in vivo.

The composition of the first aspect of the invention is a pro-angiogenic pharmaceutical composition.

A compound promoting the expression of one or more lncRNAs selected from SEQ ID NOs 1 to 22—as defined herein in item (i)—may be any compound enhancing or upregulating the transcription of an lncRNA selected from SEQ ID NOs 1 to 22. Non-limiting examples of such compounds are transcription factors enhancing the transcription of the genes encoding the lncRNAs selected from SEQ ID NOs 1 to 22 or a small molecule enhancing the expression of one or more lncRNAs selected from SEQ ID NOs 1 to 22. A transcription factor is a protein binding to specific DNA sequences, thereby controlling the transcription of genetic information from DNA to RNA. Transcription factors which enhance the expression of pro-angiogenic genes are known. A preferred example is HIF1a (hypoxia-inducible factor 1). Another regulatory role could be attributed to chromatin modifiers, e.g. modifiers that regulate the methylation status in CpG islands next to lncRNA genes. A small molecule is a low molecular weight compound which is by definition not a polymer. A compound promoting the activity of one or more lncRNAs selected from SEQ ID NOs 1 to 22—as defined herein in item (i)—may be any compound which causes that said lncRNA effectively performs its function in a cell. Hence, in the simplest form such a compound may be a recombinantly produced or isolated lncRNAs selected from SEQ ID NOs 1 to 22 or any precursor or fragment thereof. In this embodiment the administration of a recombinantly produced or isolated lncRNA increases the concentration of lncRNA in the subject to be treated. This higher concentration promotes the overall activity of the respective lncRNA in the subject. The fragments have to retain or essentially retain the function of the full-length lncRNA. Such a compound may also be a vector or host being capable of producing such an lncRNAs. Hence, the fragments have to be functional fragments. Also orthologous or homologous sequences of the lncRNA selected from SEQ ID NOs 1 to 22 from different species including precursors or functional fragments thereof may be used. Alternatively, such a compound may be a compound maintaining or even enhancing the activity of an lncRNA selected from SEQ ID NOs 1 to 22 by either directly or indirectly interacting with the lncRNA. For instance, such a compound may prevent an lncRNAs selected from SEQ ID NOs 1 to 22 from degeneration by RNases or may be an interaction partner, such as another lncRNA, which binds to and promotes the activity of an lncRNA selected from SEQ ID NOs 1 to 22. Compounds as defined herein in item (i) will be further detailed herein below.

The efficiency of a compound as defined herein in item (i) can also be quantified by methods comparing the level of expression and/or activity of an lncRNA selected from SEQ ID NOs 1 to 22 in the presence of a compound promoting the activity and/or expression of the lncRNA, such as a transcription factor, to that in the absence of said compound. For example, as an activity measure may be used: the change in amount of lncRNA formed. The method is preferably effected in high-throughput format as further detailed herein below.

A compound inhibiting the expression of one or more lncRNAs selected from SEQ ID NOs 23 to 42—as defined herein in item (ii)—is in accordance with the present invention a compound lowering or preventing the transcription of one or more of the genes encoding the lncRNAs selected of SEQ ID NOs 23 to 42. Such compounds include compounds interfering with the transcriptional machinery and/or its interaction with the promoter of said genes and/or with expression control elements remote from the promoter such as enhancers. The compound inhibiting the expression of an lncRNA selected from SEQ ID NOs 23 to 42 specifically inhibits the expression of said lncRNA, for example, by specifically interfering with the promoter region controlling the expression of the lncRNA. Preferably, the transcription of an lncRNA selected from SEQ ID NOs 23 to 42 is reduced by at least 50%, more preferred at least 75% such as at least 90% or 95%, even more preferred at least 98% and most preferred by about 100%. A compound inhibiting the activity of an lncRNAs selected from SEQ ID NOs 23 to 42—as defined herein in item (ii)—in accordance with the present invention causes said lncRNA to perform its function with lowered efficiency. The compound inhibiting the activity of an lncRNAs selected from SEQ ID NOs 23 to 42 specifically inhibits the activity of said lncRNA. Preferably, the activity of an lncRNAs selected from SEQ ID NOs 23 to 42 is reduced by at least 50%, more preferred at least 75% such as at least 90% or 95%, even more preferred at least 98%, and most preferably about 100%. Means and methods for determining the reduction of activity of RNA are established in the art and are described, for example, in Esau et al. (2004), JBC, 279:52361-52365 or Gribbings et al. (2009), Nature Cell Biology 11, 1143-1149. Compounds as defined herein in item (i) may be an antisense molecule, siRNA, shRNA, antibody, ribozyme, aptamer, or small molecule. These and other compounds will be further detailed herein below.

The efficiency of an inhibiting compound can be quantified by methods comparing the level of activity in the presence of the inhibitor to that in the absence of the inhibitor. For example, as an activity measure may be used: the change in amount of lncRNA formed. Such a method may be effected in high-throughput format in order to test the efficiency of several inhibiting compound simultaneously. High-throughput assays, independently of being biochemical, cellular or other assays, generally may be performed in wells of microtiter plates, wherein each plate may contain 96, 384 or 1536 wells. Handling of the plates, including incubation at temperatures other than ambient temperature, and bringing into contact of test compounds with the assay mixture is preferably effected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits the expected activity, said mixture of test compounds may be de-convoluted to identify the one or more test compounds in said mixture giving rise to said activity.

As is evident from the examples herein below, lncRNAs which are involved in angiogenic signalling were identified in an experimental setup, wherein the expression of lncRNAs was determined in Human Umbilical Vein Endothelial cells (HUVEC cells) which have been cultured under hypoxic conditions (i.e. 0.2% oxygen for 24 h) and compared to HUVEC control cells cultured under normal oxygen conditions. Hypoxia is a strong-pro-angiogenic stimulus (Pugh and Radcliffe (2003), Nat Med, 9(6):677-84). In simple terms, hypoxia drives tumor angiogenesis. The relationship between the two is often considered a matter of supply and demand. For example, ineffectively-vascularized tumor tissue becomes hypoxic, stimulating neoangiogenesis to improve the influx of oxygen, thereby diminishing the angiogenic drive (Moeller et al (2004), Semin Radiat Oncol; 14(3):215-21). Culturing HUVEC cells under hypoxic conditions is an established model for determining angiogenic responses and compounds involved in angiogenic signalling (for example, Veschini et al. (2007), Blood, 109: 2565-2570 and Calvani et al. (2007), Blood, 107(7):2705-2712).

The expression profile of lncRNAs under hypoxic conditions and normal oxygen (i.e. normoxic) conditions was determined by using the NCode Array technology as well as RNA-sequencing techniques (RNA-Seq). It was surprisingly found that certain lncRNAs are significantly differentially expressed after hypoxia in HUVECs. These lncRNAs are shown in Table 1. In more detail, lncRNAs corresponding to SEQ ID NO: 1 to 22 were found to be significantly upregulated under hypoxic conditions, while lncRNAs corresponding to SEQ ID NO: 23 to 42 were found to be significantly downregulated under hypoxic conditions. Because hypoxia is a strong-pro-angiogenic stimulus the lncRNAs of SEQ ID NOs 1 to 22 are pro-angiogenic factors. Hence, a compound promoting the expression and/or the activity of one or more long lncRNAs selected from SEQ ID NOs 1 to 22 will be beneficial in a pro-angiogenic therapy. On the other hand, lncRNAs of SEQ ID NO: 23 to 42 are anti-angiogenic factors. A compound inhibiting the expression and/or the activity of one or more (lncRNAs selected from SEQ ID NOs 23 to 42 will therefore be beneficial in pro-angiogenic therapy.

This principle has been further experimentally proven for the pro-angiogenic factors of SEQ ID NOs 1 to 3 and SEQ ID NO: 14.

SEQ ID NOs 1 to 3 are the three different isoforms of the lncRNA DSCAM-1. As defined herein, SEQ ID NO: 1 is the isoform 3, SEQ ID NO: 2 is the isoform 2, and SEQ ID NO: 3 is the isoform 1 of DSCAM-1. DSCAM-1 is also referred to herein as linc00323, linc323 or HSLINCR. The designation DSCAM-1 is in accordance with the LNCipedia database, the designation linc00323 or linc323 is in accordance with the Ensembl Genome Browser, and the designation HSLINCR is a designation of the inventors. SEQ ID NO: 1 (DSCAM-1, isoform 3) is also referred to herein as linc00323-003, HSLINCR-003 or lnc-DSCAM-1:2 (noting that in the LNCipedia database isoforms 2 and 3 are named the other way round as in the Ensembl Genome Browser). SEQ ID NO: 2 (DSCAM-1, isoform 2) is also designated herein as linc00323-002, HSLINCR-002 or lnc-DSCAM-1: 3. SEQ ID NO: 1 (DSCAM-1, isoform 1) is also named herein linc00323-001, HSLINCR-001 or lnc-DSCAM-1:1. All three isoforms share the sequence of SEQ ID NO: 43 and isoforms 2 and 3 additionally share the sequence of SEQ ID NO: 44 (see FIG. 1). The lncRNA DSCAM-1 is encoded on chromosome 21. The expression of all three isoforms is significantly upregulated under hypoxic conditions, most significantly the expression of lncRNA DSCAM-1 isoform 3 (SEQ ID NO: 1) (see FIG. 3). An siRNA directed against of lncRNA DSCAM-1 isoform 3 impairs the proliferation of ECs under normoxic conditions (see FIG. 5). Furthermore, the overexpression of lncRNA DSCAM-1 isoform 3 in ECs cells under normoxic conditions influences the expression of known angiogenesis-related genes. The expression of known pro-angiogenic factors, such as ICAM-1 and VEGF, was significantly increased upon the overexpression of DSCAM-1 isoform 3 in ECs under normoxic conditions (see FIG. 9). In addition, VEGF stimulates the expression of DSCAM-1 isoform 3 (see FIG. 10). This body of evidence confirms that the lncRNAs of SEQ ID NOs 1 to 3 are pro-angiogenic factors.

SEQ ID NO: 14 represents the lncRNA PLAC1-1. PLAC1-1 is also referred to in the LNCipedia database as NONHSAT138623 or NR_024607. Moreover, the lncRNA PLAC1-1 is named MIR503HG-002 in the Ensembl Genome Browser. The lncRNA PLAC1-1 is encoded on the X chromosome (see FIG. 12A). The expression of the lncRNA PLAC1-1 is significantly upregulated under hypoxic conditions both in the cytoplasmic as well as the nuclear compartment (see FIG. 11). When the lncRNA lnc-PLAC1-1 is silenced by a GapmeR construct in HUVECs scratch wound closure (and consequently angiogenesis) is impaired (see FIG. 12E). Moreover, a GapmeR against the lncRNA lnc-PLAC1-1 represses GATA2 on protein level (see FIG. 12G), noting that GATA2 is a key angiogenic factor. This body of evidence shows that also the lncRNA of SEQ ID NO: 14 is a pro-angiogenic factor.

Hypoxia is a strong pro-angiogenic stimulus and induces VEGF-mediated signalling in endothelial cells. The Examples provided herein below evidence that lncRNA expression in endothelial cells is strongly altered by hypoxia. The lncRNAs of SEQ ID NOs 1 to 42 were found to be highly sensitive towards hypoxia and to be crucial for endothelial angiogenic characteristics. As exemplarily shown for DSCAM-1 and PLAC1-1 silencing of these lncRNAs impairs function of endothelial cells via the block of proliferative pathways. To the best knowledge of the inventors none of the lncRNAs of SEQ ID NOs 1 to 42 has been described in endothelial biology and they have surprisingly been found to function as crucial factors to control endothelial cell behavior. The choice to further investigate DSCAM-1 and lnc-PLAC1-1 was dependent on their high deregulation in either microarray or RNA-Seq datasets. It can be expected that also the other so far not further characterized lncRNAs of SEQ ID NOs 4 to 13 and 15 to 42 are pro-angiogenic or anti-angiogenic factors which makes them likewise suitable for medical purposes, in particular the treatment of ischemia and the promotion of wound healing.

The present invention relates in a second aspect to a compound (i) promoting the expression and/or the activity of one or more lncRNAs selected from SEQ ID NOs 1 to 22, preferably selected from SEQ ID NOs 1 to 3 and 14; and/or (ii) inhibiting the expression and/or the activity of one or more lncRNAs selected from SEQ ID NOs 23 to 42 for use in treating or preventing ischemia, preferably cardiac ischemia and most preferably coronary artery disease, or for use in promoting wound healing.

Compounds as defined herein in items (i) and (ii) have been detailed herein above in connection with the first aspect of the invention. The same compounds can be used in connection with the second aspect of the invention.

Ischemia is a restriction in blood supply to tissues, causing a shortage of oxygen and glucose needed for cellular metabolism (to keep tissue alive). Ischemia is a vascular disease involving an interruption in the arterial blood supply to a tissue, organ, or extremity that, if untreated, can lead to tissue death. It can be caused by embolism, thrombosis of an atherosclerosis artery, or trauma. Venous problems like venous outflow obstruction and low-flow states can cause acute arterial ischemia. An aneurysm is one of the most frequent causes of acute arterial ischemia. Other causes are heart conditions including myocardial infarction, mitral valve disease, chronic atrial fibrillation, cardiomyopathies, and prosthesis, in all of which thrombi are prone to develop. Hence, an ischemia can occur in several organs and tissues, such as brain, limbs, bowel or heart. Cardiac ischemia may be asymptomatic or may cause chest pain, known as angina pectoris. It occurs when the heart muscle, or myocardium, receives insufficient blood flow. This most frequently results from atherosclerosis, which is the long-term accumulation of cholesterol-rich plaques in the coronary arteries. Ischemic heart disease is the most common cause of death in most Western countries and a major cause of hospital admissions. Coronary artery disease (CAD) also known as atherosclerotic heart disease, coronary heart disease, or ischemic heart disease (IHD), is the most common type of heart disease and cause of heart attacks. The disease is caused by plaque building up along the inner walls of the arteries of the heart, which narrows the arteries and reduces blood flow to the heart. Pro-angiogenic therapy is a known means to treat or prevent ischemia (Marti and Risau (1999), Thromb Haemost. September; 82 Suppl 1:44-52).

Wound healing is the intricate process whereby the skin (or another organ-tissue) repairs itself after injury. The cell proliferation phase during wound healing is characterized by angiogenesis, collagen deposition, granulation tissue formation, epithelialization, and wound contraction (Midwood et al (2004), The International Journal of Biochemistry & Cell Biology; 36(6):1031-1037). In angiogenesis, vascular endothelial cells form new blood vessels. Hence, a pro-angiogenic therapy is a means to promote wound healing (Bahatia (2013), Mechanical and Chemical Signaling in Angiogenesis, Studies in Mechanobiology, Tissue Engineering and Biomaterials; 12(261-278)).

In accordance with a preferred embodiment of the first and second aspect of the invention the compound as defined in (i) is (a) a nucleic acid sequence which comprises or consists of the nucleic acid sequence of one or more lncRNAs selected from SEQ ID NOs 1 to 22 or an nucleic acid sequence which is at least 70% identical thereto, (b) an expression vector expressing the nucleic acid sequence as defined in (a), preferably under the control of a heart-specific promoter, or (c) a host comprising the expression vector of (b).

As discussed above the three isoforms of SEQ ID NOs 1 to 3 share the sequence of SEQ ID NO: 43 and SEQ ID NO 1 and 2 additionally share the sequence of SEQ ID NO: 44. Hence, a nucleic acid sequence which is at least 70% identical to one of SEQ ID NOs 1 to 3 preferably retains the nucleotides corresponding to SEQ ID NO: 43 and more preferably a nucleic acid sequence which is at least 70% identical to one of SEQ ID NO 2 or 3 retains the nucleotides corresponding to SEQ ID NO: 43 and 44. In other terms, these nucleotides corresponding to SEQ ID NO: 43 or SEQ ID NO: 43 and 44 preferably remain unchanged and no amino acid changes are to be introduced in the subsequences.

The term "nucleic acid sequence" or "nucleotide sequence", in accordance with the present invention, includes DNA, such as cDNA or, in a preferred embodiment genomic DNA, and RNA. It is understood that the term "RNA" as used herein comprises all forms of RNA including, in a preferred embodiment, mRNA or miRNA. The term "nucleic acid sequence" is interchangeably used in accordance with the invention with the term "polynucleotide".

The nucleic acid sequence according to item (a) of this preferred embodiment may be a recombinantly produced or isolated lncRNAs selected from SEQ ID NOs 1 to 22, any precursor thereof or any fragment thereof as long as a sequence identity of at least 70% over the entire length of an lncRNA selected from SEQ ID NOs 1 to 22 is maintained. Also orthologous or homologous sequences of the lncRNA selected from SEQ ID NOs 1 to 22 from different species including precursors or functional fragments thereof may be used. The fragments have to retain or essentially retain the function of the full-length lncRNA. Hence, the fragments have to be functional fragments.

The sequence identity of the nucleic acid sequence according to item (a) to an lncRNA selected from SEQ ID NOs 1 to 22 is with increasing preference at least 75%, at least 80%, at least 85%, at least 90%, at least 95%, at least 98%, at least 99% and 100%. Means and methods for determining sequence identity are known in the art. Preferably, the BLAST (Basic Local Alignment Search Tool) program is used for determining the sequence identity with regard to one or more lncRNAs selected from SEQ ID NOs 1 to 22.

In accordance with items (b) and (c) of the above preferred embodiment such a compound may also be an expression vector or host being capable of producing an nucleic acid sequence as defined in item (a).

An expression vector may be a plasmid that is used to introduce a specific transcript into a target cell. Once the expression vector is inside the cell, the protein that is encoded by the gene is produced by the cellular-transcription and translation machinery ribosomal complexes. The plasmid is in general engineered to contain regulatory sequences that act as enhancer and/or promoter regions and lead to efficient transcription of the transcript. In accordance with the present invention the expression vector preferably contains a heart-specific promoter. Heart-specific promoters are known in the art, for example, from Boecker at al. (2004), Mol Imagin.; 3(2):69-75. This ensures that the nucleic acid sequence is only expressed in the heart and may avoid potential unwanted side effects by expression in other organs.

Non-limiting examples of expression vectors include prokaryotic plasmid vectors, such as the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRS-Vgpt, pRSVneo, pSV2-dhfr, plZD35, pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Intvitrogen). For the formulation of a pharmaceutical composition a suitable vector is selected in accordance with good manufacturing practice. Such vectors are known in the art, for example, from Ausubel et al, Hum Gene Ther. 2011 April; 22(4):489-97 or Allay et al., Hum Gene Ther. May 2011; 22(5): 595-604.

A typical mammalian expression vector contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. The lac promoter is a typical inducible promoter, useful for prokaryotic cells, which can be induced using the lactose analogue isopropylthiol-b-D-galactoside. ("IPTG"). For recombinant expression and secretion, the polynucleotide of interest may be ligated between e.g. the PelB leader signal, which directs the recombinant protein in the periplasm and the gene III in a phagemid called pHEN4 (described in Ghahroudi et al, 1997, FEBS Letters 414:521-526). Additional elements might include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Alternatively, the recombinant (poly)peptide can be expressed in stable cell lines that contain the gene construct integrated into a chromosome. The co-transfection with a selectable marker such as dhfr, gpt, neomycin, hygromycin allows the identification and isolation of the transfected cells. The transfected nucleic acid can also be amplified to express large amounts of the encoded (poly)peptide. The DHFR (dihydrofolate reductase) marker is useful to develop cell lines that carry several hundred or even several thousand copies of the gene of interest. Another useful selection marker is the enzyme glutamine synthase (GS) (Murphy et al. 1991, *Biochem J.* 227:277-279; Bebbington et al. 1992, *Bio/Technology* 10:169-175). Using these markers, the mammalian cells are grown in selective medium and the cells with the highest resistance are selected. As indicated above, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. For vector modification techniques, see Sambrook and Russel (2001), Molecular Cloning: A Laboratory Manual, 3 Vol. Generally, vectors can contain one or more origins of replication (ori) and inheritance systems for cloning or expression, one or more markers for selection in the host, e.g., antibiotic resistance, and one or more expression cassettes. Suitable origins of replication (ori) include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, promoters, enhancers, and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers, and/or naturally-associated or heterologous promoter regions. Preferably, the nucleotide sequence as defined in item (a) of the above preferred embodiment of the invention is operatively linked to such expression control sequences allowing expression in prokaryotic or eukaryotic cells.

The host may be a prokaryotic or eukaryotic cell. A suitable eukaryotic host may be a mammalian cell, an amphibian cell, a fish cell, an insect cell, a fungal cell or a plant cell. Representative examples of bacterial cells are *E. coli*, *Streptomyces* and *Salmonella typhimurium* cells; of fungal cells are yeast cells; and of insect cells are *Drosophila* S2 and *Spodoptera* Sf9 cells. It is preferred that the cell is a mammalian cell such as a human cell. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells. The cell may be a part of a cell line, preferably a human cell line. Appropriate culture mediums and conditions for the above-described host cells are known in the art. The host is preferably a host cell and more preferably an isolated host cell. The host is also preferably a non-human host.

In accordance with another preferred embodiment of the first and second aspect of the invention the compound as defined in (i) is (a) a transcription factor promoting the expression of one or more lncRNAs selected from SEQ ID NOs 1 to 22, and/or (b) a small molecule enhancing the expression of one or more lncRNAs selected from SEQ ID NOs 1 to 22.

The term "transcription factor" as used is connection with this embodiment defines a protein or peptide that binds to specific DNA sequences, thereby controlling the transcription of the genes encoding of one or more lncRNAs selected from SEQ ID NOs 1 to 22. The efficiency of a transcription factor in activating the expression of an lncRNA selected from SEQ ID NOs 1 to 22 can be quantified by methods comparing the level of the lncRNA in the presence of the transcription factor to that in the absence of the transcription factor. For example, as an activity measure the change in amount of lncRNA formed may be used. Such a method may be effected in high-throughput format in order to test the efficiency of several inhibiting compound simultaneously. High-throughput formats have been further detailed herein above.

The small molecule enhancing the expression of one or more lncRNAs selected from SEQ ID NOs 1 to 22 is a low molecular weight organic compound which is by definition not a polymer. The small molecule of the invention is preferably a molecule that binds with high affinity to an lncRNA of SEQ ID NOs 1 to 22 and in addition enhances the activity of an lncRNA of SEQ ID NOs 1 to 22. The upper molecular weight limit for a small molecule is preferably 1500 Da, more preferably 1000 Da and most preferably 800 Da which allows for the possibility to rapidly diffuse across cell membranes so that they can reach intracellular sites of action. Libraries of small organic molecules and high-throughput techniques for screening such libraries with a specific target molecule, in the present case an lncRNA selected from SEQ ID NOs 1 to 22, are established in the art.

In accordance with a further preferred embodiment of the first and second aspect of the invention the compound as defined in (ii) is (a) a nucleic acid sequence which comprises or consists of a nucleotide sequence being complementary to at least 12 continuous nucleotides of a lncRNAs selected from SEQ ID NOs 23 to 42, (b) a nucleic acid sequence which comprises or consists of a nucleotide sequence which is at least 70% identical to the complementary strand of one or more lncRNAs selected from SEQ ID NOs 23 to 42, (c) a nucleic acid sequence which comprises or consists of a nucleotide sequence according to (a) or (b), wherein U is replaced by T, (d) an expression vector expressing the nucleic acid sequence as defined in any one of (a) to (c), preferably under the control of a heart-specific promoter, or (e) a host comprising the expression vector of (d).

The nucleic acid sequences as defined in items (a) to (c) of this preferred embodiment comprise or consist of sequences that comprise or are complementary to nucleotides of a lncRNAs selected from SEQ ID NOs 23 to 42. Hence, these nucleic acid sequences comprise or are antisense nucleic acid sequences. The antisense technology for silencing the expression of a target gene is well-established and widely used in the art to treat various diseases.

The molecule according to item (a) of this preferred embodiment of the invention comprises or consists of a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, or all 23 nucleotides of SEQ ID NOs 23 to 42. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of SEQ ID NOs 23 to 42 i.e. the nucleotides are consecutive in the respective SEQ ID NO.

The molecule according to item (a) is preferably a "siRNA". The term "siRNA" in accordance with the present invention refers to small interfering RNA, also known as short interfering RNA or silencing RNA. siRNAs are a class of 18 to 30, preferably 20 to 25, most preferred 21 to 23 or 21 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome. siRNAs have a well defined structure: a short double-strand of RNA (dsRNA), advantageously with at least one RNA strand having an overhang. Each strand typically has a 5' phosphate group and a 3' hydroxyl (—OH) group. This structure is the result of processing by dicer, an enzyme that converts either long dsRNAs or small hairpin RNAs into siRNAs. siRNAs can also be exogenously (artificially) introduced into cells to bring about the specific knockdown of a gene of interest. Thus, any gene of which the sequence is known can in principle be targeted based on sequence complementarity with an appropriately tailored siRNA. The double-stranded RNA molecule or a metabolic processing product thereof is capable of mediating target-specific nucleic acid modifications, particularly RNA interference and/or DNA methylation. Also preferably at least one RNA strand has a 5'- and/or 3'-overhang. Preferably, one or both ends of the double-strand has a 3'-overhang from 1-5 nucleotides, more preferably from 1-3 nucleotides and most preferably 2 nucleotides. In general, any RNA molecule suitable to act as siRNA is envisioned in the present invention. The most efficient silencing was so far obtained with siRNA duplexes composed of 21-nt sense and 21-nt antisense strands, paired in a manner to have 2-nt 3'—overhangs. The sequence of the 2-nt 3' overhang makes a small contribution to the specificity of target recognition restricted to the unpaired nucleotide adjacent to the first base pair (Elbashir et al. Nature. 2001 May 24; 411(6836):494-8). 2'-deoxynucleotides in the 3' overhangs are as efficient as ribonucleotides, but are often cheaper to synthesize and probably more nuclease resistant. The siRNA according to the invention comprises an antisense strand which comprises or consists of a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, or all 23 nucleotides of SEQ ID NOs 23 to 42. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of SEQ ID NOs 23 to 42, i.e. the nucleotides are consecutive in the respective SEQ ID NO.

The molecule according to item (a) is also preferably a "shRNA". A "shRNA" in accordance with the present invention is a short hairpin RNA, which is a sequence of RNA that makes a (tight) hairpin turn that can also be used to silence gene expression via RNA interference. shRNA preferably utilizes the U6 promoter for its expression. The shRNA hairpin structure is cleaved by the cellular machinery into siRNA, which is then bound to the RNA-induced silencing complex (RISC). This complex binds to and cleaves mRNAs which match the shRNA that is bound to it. The shRNA according to the invention comprises or consists a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, or all 23 nucleotides of SEQ ID NOs 23 to 42. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of SEQ ID NOs 23 to 42, i.e. the nucleotides are consecutive in the respective SEQ ID NO.

An molecule according to item (b) of the above preferred embodiment of the invention is capable of interacting with, more specifically hybridizing with the target lncRNA. By formation of the hybrid the function of the lncRNA is reduced or blocked. Standard methods relating to such antisense technology have been described (see, e.g., Melani et al., Cancer Res. (1991) 51:2897-2901). The term "antisense molecule" in accordance with the present invention thus relates to a nucleic acid molecule, preferably a RNA molecule, that has a base sequence complementary to a given lncRNA, i.e. the "sense" sequence.

A particularly preferred example of the molecule according to item (b) is an Endoribonuclease-prepared siRNA (esiRNA). An esiRNA is a mixture of siRNA oligos resulting from cleavage of a long double-stranded RNA (dsRNA) according to item (b) with an endoribonuclease such as *Escherichia coli* RNase III or dicer. esiRNAs are an alternative concept to the usage of chemically synthesized siRNA for RNA Interference (RNAi). An esiRNAs is the enzymatic digestion of a long double stranded RNA in vitro. For the generation of esiRNAs a cDNA of an lncRNA template may be amplified by PCR and tagged with two bacteriophage-promotor sequences. RNA polymerase is then used to generate long double stranded RNA that is complentary to the target-gene cDNA. This complentary RNA may be subsequently digested with RNase III from *Escherichia coli* to generate short overlapping fragments of siRNAs with a length between 18-25 base pairs. This complex mixture of short double stranded RNAs is similar to the mixture generated by Dicer cleavage in vivo and is therefore called endoribonuclease-prepared siRNA or short esiRNA. Hence, esiRNA are a heterogeneous mixture of siRNAs that all target the same mRNA sequence. esiRNAs lead to highly specific and effective gene silencing.

The sequence identity of the antisense molecule according to item (b) to an lncRNA selected from SEQ ID NOs 23 to 42 is with increasing preference at least 75%, at least 80%, at least 85%, at least 90%, at least 95%, at least 98%, at least 99% and 100%. Means and methods for determining sequence identity are known in the art. Preferably, the BLAST (Basic Local Alignment Search Tool) program is used for determining the sequence identity with regard to one or more lncRNAs selected from SEQ ID NOs 23 to 42.

Antisense molecules, siRNAs and shRNAs of the present invention are preferably chemically synthesized using appropriately protected ribonucleoside phosphoramidites and a conventional RNA synthesizer. Suppliers of RNA synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK).

The ability of antisense molecules, siRNA, and shRNA to potently, but reversibly, silence lncRNA and genes in vivo makes these molecules particularly well suited for use in the pharmaceutical composition of the invention. Ways of administering siRNA to humans are described in De Fougerolles et al., Current Opinion in Pharmacology, 2008, 8:280-285. Such ways are also suitable for administering other small RNA molecules like shRNA. Accordingly, such pharmaceutical compositions may be administered directly formulated as a saline, via liposome based and polymer-based nanoparticle approaches, as conjugated or complexation pharmaceutical compositions, or via viral delivery systems. Direct administration comprises injection into tissue, intranasal and intratracheal administration. Liposome based and polymer-based nanoparticle approaches comprise the cationic lipid Genzyme Lipid (GL) 67, cationic liposomes, chitosan nanoparticles and cationic cell penetrating peptides (CPPs). Conjugated or complexation pharmaceutical compositions comprise PEI-complexed antisense molecules, siRNA, shRNA or miRNA. Further, viral delivery systems comprise influenza virus envelopes and virosomes.

The antisense molecules, siRNAs, shRNAs may comprise modified nucleotides such as locked nucleic acids (LNAs). The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. Such oligomers are synthesized chemically and are commercially available. The locked ribose conformation enhances base stacking and backbone pre-organization. This significantly increases the hybridization properties (melting temperature) of oligonucleotides. Particularly preferred example of siRNAs is GapmeR (LNA™ GapmeRs (Exiqon)). GapmeRs are potent antisense oligonucleotides used for highly efficient inhibition of mRNA and lncRNA function. GapmeRs contain a central stretch of DNA monomers flanked by blocks of LNAs. The GapmeRs are preferably 14-16 nucleotides in length and are optionally fully phosphorothioated. The DNA gap activates the RNAse H-mediated degradation of targeted RNAs and is also suitable to target transcripts directly in the nucleus. GapmeRs are used in the examples, e.g., to downregulate the lncRNA DSCAM-1 isoform 3 (LINC00323-003) (SEQ ID NO: 1) in HUVEC cells.

Examples of suitable expression vectors which may be used in connection with item (d) of the above-preferred embodiment have been detailed herein above.

In accordance with a different preferred embodiment of the first and second aspect of the invention the compound as defined in (ii) is an aptamer, a ribozyme, an antibody, a protein drug, or a small molecule inhibitor.

The aptamer, ribozyme, antibody, protein drug, or small molecule inhibitor of this embodiment specifically bind to one or more lncRNA selected from SEQ ID NOs 23 to 42, thereby inhibiting the activity of one or more lncRNA selected from SEQ ID NOs 23 to 42.

The term "aptamer" in accordance with the present invention refers to DNA or RNA molecules being either in the natural D-conformation or in the L-conformation ("spiegelmer") that have been selected from random pools based on their ability to bind other molecules. Aptamers have been selected which bind nucleic acid, proteins, small organic compounds, and even entire organisms. A database of aptamers is maintained at http://aptamericmb.utexas.edu/.

More specifically, aptamers can be classified as DNA or RNA aptamers or peptide aptamers. Whereas the former consist of (usually short) strands of oligonucleotides, the latter consist of a short variable peptide domain, attached at both ends to a protein scaffold. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. The molecular target envisaged by the present invention is a nucleic acid, namely an lncRNA selected from 23 to 42. Hence, aptamers can be produced against the target molecule of the invention. Peptide aptamers are peptides that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable loop length is typically comprised of 10 to 20 amino acids, and the scaffold may be any protein which has good solubility properties. Currently, the bacterial protein Thioredoxin-A is the most used scaffold protein, the variable loop being inserted within the reducing active site, which is a -Cys-Gly-Pro-Cys- loop in the wild protein, the two cysteines lateral chains being able to form a disulfide bridge. Peptide aptamer selection can be made using different systems, but the most used is currently the yeast two-hybrid system.

Aptamers offer the utility for biotechnological and therapeutic applications as they offer molecular recognition properties that rival those of the commonly used biomolecules, in particular antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Non-modified aptamers are cleared rapidly from the bloodstream, with a half-life of minutes to hours, mainly due to nuclease degradation and clearance from the body by the kidneys, a result of the aptamer's inherently low molecular weight. The rapid clearance of aptamers can be an advantage in applications such as in vivo diagnostic imaging. Several modifications, such as 2'-fluorine-substituted pyrimidines, polyethylene glycol (PEG) linkage, etc. are available to scientists with which the half-life of aptamers easily can be increased to the day or even week time scale.

The term "ribozymes" refers to RNA molecules that act as enzymes in the absence of proteins. These RNA molecules act catalytic or autocatalytic and are capable of cleaving e.g. other RNAs at specific target sites but they have also been found to catalyze the aminotransferase activity of the ribosome. Selection of appropriate target sites and corresponding ribozymes can be done as described for example in Zaher and Unrau (2007), RNA 13 (7): 1017-1026.

Examples of well-characterized small self-cleaving RNAs are the hammerhead, hairpin, hepatitis delta virus, and in vitro-selected lead-dependent ribozymes. The organization of these small catalysts is in contrast to that of larger ribozymes, such as the group I intron.

The principle of catalytic self-cleavage has become well established in the last 10 years. The hammerhead ribozymes are characterized best among the RNA molecules with ribozyme activity. Since it was shown that hammerhead structures can be integrated into heterologous RNA sequences and that ribozyme activity can thereby be transferred to these molecules, it appears that catalytic sequences for almost any target sequence can be created, provided the target sequence contains a potential matching cleavage site.

The basic principle of constructing hammerhead ribozymes is as follows: An interesting region of the RNA, which contains the GUC (or CUC) triplet, is selected. Two oligonucleotide strands, each with 6 to 8 nucleotides, are taken and the catalytic hammerhead sequence is inserted between them. Molecules of this type were synthesized for numerous target sequences. They showed catalytic activity in vitro and in some cases also in vivo. The best results are usually obtained with short ribozymes and target sequences. Since the target sequence is a short RNA sequence, namely an lncRNA selected from SEQ ID NOs 23 to 42. lncRNAs selected from SEQ ID NOs 23 to 42 are bona fide targets sequences for the generation of ribozymes being capable to specifically cleave an lncRNA selected from SEQ ID NOs 23 to 42.

Also the aptamers and ribozymes may comprise modified nucleotides, such as locked nucleic acids (LNAs).

The term "antibody" as used in accordance with the present invention comprises, for example, polyclonal or monoclonal antibodies. Furthermore, also derivatives or fragments thereof, which still retain the binding specificity, are comprised in the term "antibody". Antibody fragments or derivatives comprise, inter alia, Fab or Fab' fragments, Fd, F(ab')$_2$, Fv or scFv fragments, single domain $V_H$ or V-like domains, such as VhH or V-NAR-domains, as well as multimeric formats such as minibodies, diabodies, tribodies, tetrabodies or chemically conjugated Fab'-multimers (see, for example, Altshuler et al., 2010, Holliger and Hudson, 2005). The term "antibody" also includes embodiments such as chimeric (human constant domain, non-human variable domain), single chain and humanized (human antibody with the exception of non-human CDRs) antibodies.

Various techniques for the production of antibodies and fragments thereof are well known in the art and described, e.g. in Altshuler et al., 2010. Thus, polyclonal antibodies can be obtained from the blood of an animal following immunisation with an antigen in mixture with additives and adjuvans and monoclonal antibodies can be produced by any technique which provides antibodies produced by continuous cell line cultures. Examples for such techniques are described, e.g. Harlow and Lane (1988) and (1999) and include the hybridoma technique originally described by Kohler and Milstein, 1975, the trioma technique, the human B-cell hybridoma technique (see e.g. Kozbor, 1983; Li et al., 2006) and the EBV-hybridoma technique to produce human monoclonal antibodies (Cole et al., 1985). Furthermore, recombinant antibodies may be obtained from monoclonal antibodies or can be prepared de novo using various display methods such as phage, ribosomal, mRNA, or cell display. A suitable system for the expression of the recombinant (humanized) antibodies or fragments thereof may be selected from, for example, bacteria, yeast, insects, mammalian cell lines or transgenic animals or plants (see, e.g., U.S. Pat. No. 6,080,560; Holliger and Hudson, 2005). Further, techniques described for the production of single chain antibodies (see, inter alia, U.S. Pat. No. 4,946,778) can be adapted to produce single chain antibodies specific for the target of this invention. Surface plasmon resonance as employed in the BIAcore system can be used to increase the efficiency of phage antibodies.

The term "protein drugs" designates designer drugs that are derivatives of human proteins. These proteins are used as scaffold to create a protein drug by well-established screening procedures (see Tomlinson et at (2004), NATURE BIOTECHNOLOGY, 22(5): 521-522). Non-limiting examples of human proteins which serve as a scaffold for designing protein drugs are transferrin, C-type lectins, trinectins, domain antibodies, kunitz domains, lipocalins and the Fyn SH3 domain.

A small molecule inhibitor is a low molecular weight organic compound which is by definition not a polymer. The small molecule of the invention is preferably a molecule that binds with high affinity to an lncRNA of SEQ ID NOs 2 to 42 and in addition inhibits the activity of an lncRNA of SEQ ID NOs 2 to 42. The upper molecular weight limit for a small molecule is preferably 1500 Da, more preferably 1000 Da and most preferably 800 Da which allows for the possibility to rapidly diffuse across cell membranes so that they can reach intracellular sites of action. Libraries of small organic molecules and high-throughput techniques for screening such libraries with a specific target molecule, in the present case an lncRNA selected from SEQ ID NOs 2 to 42, are established in the art.

Antisense molecule, siRNA, shRNA, antibody, enzyme, ribozyme, aptamer, protein drug, or small molecule inhibitor may be fused to a lipid, such as a cholesterol. Means and methods to introduce lipid modifications and in particular a cholesterol modification to a nucleic acid molecule are described in Krutzfeldt et al. 2005 (Nature 438, 685-689). For example, a cholesterol may be linked through a hydroxylprolinol linkage to a nucleic acid molecule. Such modifications increase the efficiency of the uptake of a nucleic acid molecule and in particular of small RNAs into the cell.

The present invention relates in a third aspect to a pharmaceutical composition comprising (i) a compound promoting the expression and/or the activity of one or more lncRNAs selected from SEQ ID NOs 23 to 42; and/or (ii) a compound inhibiting the expression and/or the activity of one or more long non-coding RNAs (lncRNAs) selected from SEQ ID NOs 1 to 22, preferably selected from SEQ ID NOs 1 to 3 and 14.

The formulation and administration of the pharmaceutical composition of the invention have been detailed herein above in connection with the first aspect of the invention. The same formulations and administrations can be used in connection with the second aspect of the invention.

The composition of the third aspect of the invention is an anti-angiogenic pharmaceutical composition.

A compound promoting the expression of one or more lncRNAs selected from SEQ ID NOs 23 to 42—as defined herein in item (i)—may be any compound enhancing or upregulating the transcription of an lncRNA selected from SEQ ID NOs 23 to 42. Non-limiting examples of such compounds are transcription factors enhancing the transcription of the genes encoding the lncRNAs selected from SEQ ID NOs 23 to 42 or a small molecule enhancing the expression of one or more lncRNAs selected from SEQ ID NOs 23 to 42. A transcription factor is a protein binding to specific DNA sequences, thereby controlling the transcription of genetic information from DNA to RNA. A small molecule is a low molecular weight compound which is by definition not a polymer. A compound promoting the activity of one or more lncRNAs selected from SEQ ID NOs 23 to 42—as defined herein in item (i)—may be any compound which causes that said lncRNA effectively performs its function in a cell. Hence, in the simplest form such a compound may be a recombinantly produced or isolated lncRNA selected from SEQ ID NOs 23 to 42 or any precursor or fragment thereof. In this embodiment the administration of an recombinantly produced or isolated lncRNA increases the concentration of lncRNA in the subject to be treated. This higher concentration promotes the overall activity of the respective lncRNA in the subject. The fragments have to retain or essentially retain the function of the full-length lncRNA. Such a compound may also be a vector or host being capable of producing such an lncRNA. Hence, the fragments have to be functional fragments. Also orthologous or homologous sequences of the lncRNAs selected from SEQ ID NOs 23 to 42 from different species including precursors or functional fragments thereof may be used. Alternatively, such a compound may be a compound maintaining or even enhancing the activity of an lncRNA selected from SEQ ID NOs 23 to 42 by either directly or indirectly interacting with the lncRNA. For instance, such a compound may prevent an lncRNA selected from SEQ ID NOs 23 to 42 from degeneration by RNases or may be an interaction partner, such as another lncRNA, which binds to and promotes the activity of an lncRNA selected from SEQ ID NOs 23 to 42. Compounds as defined herein in item (i) will be further detailed herein below.

The efficiency of a compound as defined herein in item (ii) can also be quantified by methods comparing the level of expression and/or activity of an lncRNA selected from SEQ ID NOs 23 to 42 in the presence of an promotor of the lncRNA, such as a transcription factor, to that in the absence of the promotor. For example, as an activity measure the change in amount of lncRNA formed may be used. The method is preferably effected in high-throughput format as further detailed herein below.

A compound inhibiting the expression of one or more lncRNAs selected from SEQ ID NOs 1 to 22—as defined herein in item (ii)—is in accordance with the present invention a compound lowering or preventing the transcription of one or more of the genes encoding the lncRNAs selected of SEQ ID NOs 1 to 22. Such compounds include compounds interfering with the transcriptional machinery and/or its interaction with the promoter of said genes and/or with expression control elements remote from the promoter such as enhancers. The compound inhibiting the expression of an lncRNAs selected from SEQ ID NOs 1 to 22 specifically inhibits the expression of said lncRNA, for example, by specifically interfering with the promoter region controlling the expression of the lncRNA. Preferably, the transcription of an lncRNAs selected from SEQ ID NOs 1 to 22 is reduced by at least 50%, more preferred at least 75% such as at least 90% or 95%, even more preferred at least 98% and most preferred by about 100%. A compound inhibiting the activity of an lncRNA selected from SEQ ID NOs 1 to 22—as defined herein in item (ii)—in accordance with the present invention causes said lncRNA to perform its function with lowered efficiency. The compound inhibiting the activity of an lncRNA selected from SEQ ID NOs 1 to 22 specifically inhibits the activity of said lncRNA. Preferably, the activity of an lncRNA selected from SEQ ID NOs 1 to 22 is reduced by at least 50%, more preferred at least 75% such as at least 90% or 95%, even more preferred at least 98%, and most preferably about 100%. Means and methods for determining the reduction of activity of an RNA are established in the art and are described, for example, in Esau et al. (2004), JBC, 279:52361-52365 or Gribbings et al. (2009), Nature Cell Biology 11, 1143-1149. Compounds as defined herein in item (i) may be an antisense molecule, siRNA, shRNA, antibody, ribozyme, aptamer, or small molecule. These and other compounds will be further detailed herein below.

As discussed above, the three isoforms of SEQ ID NOs 1 to 3 share the sequence of SEQ ID NO: 43 and SEQ ID NO 1 and 2 additionally share the sequence of SEQ ID NO: 44. Hence, a compound specifically inhibiting the activity of the SEQ ID NOs 1 to 3 may be designed by targeting SEQ ID NO: 43, and a compound specifically inhibiting the activity of the SEQ ID NOs 1 and 2 may be designed by targeting SEQ ID NO: 44.

The efficiency of an inhibiting compound can be quantified by methods comparing the level of activity in the presence of the inhibitor to that in the absence of the inhibitor. For example, as an activity measure the change in amount of lncRNA formed may be used. Such a method may be effected in high-throughput format in order to test the efficiency of several inhibiting compound simultaneously. High-throughput assays, independently of being biochemical, cellular or other assays, generally may be performed in wells of microtiter plates, wherein each plate may contain 96, 384 or 1536 wells. Handling of the plates, including incubation at temperatures other than ambient temperature, and bringing into contact of test compounds with the assay mixture is preferably effected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits the expected activity, said mixture of test compounds may be de-convoluted to identify the one or more test compounds in said mixture giving rise to said activity.

As discussed in detail in connection with the first aspect of the invention, the lncRNAs of SEQ ID NOs 1 to 22 are pro-angiogenic factors. Hence, a compound inhibiting the expression and/or the activity of one or more lncRNAs selected from SEQ ID NOs 1 to 22 will be beneficial in an anti-angiogenic therapy. lncRNAs of SEQ ID NO: 23 to 42 are anti-angiogenic factors. Consequently, a compound promoting the expression and/or the activity of one or more lncRNAs selected from SEQ ID NOs 23 to 42 will be beneficial in an anti-angiogenic therapy.

The present invention relates in a fourth aspect to a compound (i) promoting the expression and/or the activity of one or more lncRNAs selected from SEQ ID NOs 23 to 42; and/or (ii) inhibiting the expression and/or the activity of one or more lncRNAs selected from SEQ ID NOs 1 to 22, preferably selected from SEQ ID NOs 1 to 3 and 14 for use in treating or preventing a tumor, preferably a hypoxic tumor, or for use in treating or preventing diabetic retinopathy.

Compounds as defined herein in items (i) and (ii) have been detailed herein above in connection with the third aspect of the invention. The same compounds can be used in connection with the fourth aspect of the invention.

The terms "tumor" and "cancer" are interchangeably used herein. Angiogenesis plays a critical role in the growth and spread of cancer (Nishida et al. (2006), Vasc Health Risk Management, 2(3): 213-219). A blood supply is necessary for tumors to grow beyond a few millimeters in size. Tumors can cause this blood supply to form by giving off chemical signals that stimulate angiogenesis. Tumors can also stimulate nearby normal cells to produce angiogenesis signalling molecules. The resulting new blood vessels "feed" growing tumors with oxygen and nutrients, allowing the cancer cells to invade nearby tissue, to move throughout the body, and to form new colonies of cancer cells, called metastases. Because tumors cannot grow beyond a certain size or spread without a blood supply, blocking tumor angiogenesis is a known anti-cancer therapy.

Diabetic retinopathy is retinopathy (damage to the retina) caused by complications of diabetes, which can eventually lead to blindness. As the disease progresses, severe nonproliferative diabetic retinopathy enters an advanced, or proliferative (PDR) stage. The blood vessels proliferate in order to supplement the lack of oxygen in the retina caused by the cell proliferation. The growth of the blood vessels may be inhibited by an anti-angiogenic therapy (Bahatia (2013), Mechanical and Chemical Signaling in Angiogenesis, Studies in Mechanobiology, Tissue Engineering and Biomaterials; 12(261-278)).

In accordance with a preferred embodiment of the third and fourth aspect of the invention the compound as defined in (i) is (a) a nucleic acid sequence which comprises or consists of the nucleic acid sequence of one or more lncRNAs selected from SEQ ID NOs 23 to 42 or an nucleic acid sequence which is at least 70% identical thereto, (b) an expression vector expressing the nucleic acid sequence as defined in (a), preferably under the control of a heart-specific promoter, or (c) a host comprising the expression vector of (b).

The nucleic acid sequence according to item (a) of this preferred embodiment may be a recombinantly produced or isolated lncRNA selected from SEQ ID NOs 23 to 42, any precursor thereof or any fragment thereof as long as a sequence identity of at least 70% over the entire length of an lncRNA selected from SEQ ID NOs 23 to 42 is maintained. Also orthologous or homologous sequences of the lncRNAs selected from SEQ ID NOs 23 to 42 from different species including precursors or a functionals fragment thereof may be used. The fragments have to retain or essentially retain the function of the full-length lncRNA. Hence, the fragments have to be functional fragments.

The sequence identity of the nucleic acid sequence according to item (a) to an lncRNA selected from SEQ ID NOs 23 to 42 is with increasing preference at least 75%, at least 80%, at least 85%, at least 90%, at least 95%, at least 98%, at least 99% and 100%. Means and methods for determining sequence identity are known in the art. Preferably, the BLAST (Basic Local Alignment Search Tool) program is used for determining the sequence identity with regard to one or more lncRNAs selected from SEQ ID NOs 23 to 42.

In accordance with items (b) and (c) of the above preferred embodiment such a compound may also be an expression vector or host being capable of producing an nucleic acid sequence as defined in item (a). Suitable expression vectors and hosts have been detailed herein above in connection with the first and second aspect of the invention. These expression vectors can also be used in connection with the third and fourth aspect of the invention.

In accordance with another preferred embodiment of the third and fourth aspect of the invention the compound as defined in (i) is (a) a transcription factor promoting the expression of one or more lncRNAs selected from SEQ ID NOs 23 to 42, and/or (b) a small molecule enhancing the expression of one or more lncRNAs selected from SEQ ID NOs 23 to 42.

The term "transcription factor" as used is connection with this embodiment defines a protein or peptide that binds to specific DNA sequences, thereby controlling the transcription of the genes encoding of one or more lncRNAs selected from SEQ ID NOs 23 to 42. The efficiency of a transcription factor in activating the expression of an lncRNA selected from SEQ ID NOs 23 to 42 can be quantified by methods comparing the level of the lncRNA in the presence of the transcription factor to that in the absence of the transcription factor. For example, as an activity measure the change in amount of lncRNA formed may be used. Such a method may be effected in high-throughput format in order to test the efficiency of several inhibiting compound simultaneously. High-throughput formats have been further detailed herein above.

The small molecule enhancing the expression of one or more lncRNAs selected from SEQ ID NOs 23 to 42 is a low molecular weight organic compound which is by definition not a polymer. The small molecule of the invention is preferably a molecule that binds with high affinity to an lncRNA of SEQ ID NOs 23 to 42 and in addition enhances the activity of an lncRNA of SEQ ID NOs 23 to 42. The upper molecular weight limit for a small molecule is preferably 1500 Da, more preferably 1000 Da and most preferably 800 Da which allows for the possibility to rapidly diffuse across cell membranes so that they can reach intracellular sites of action. Libraries of small organic molecules and high-throughput techniques for screening such libraries with a specific target molecule, in the present case an lncRNA selected from SEQ ID NOs 23 to 42, are established in the art.

In accordance with a preferred embodiment of the third and fourth aspect of the invention the compound as defined in (ii) is (a) a nucleic acid sequence which comprises or consists of a nucleotide sequence being complementary to at least 12 continuous nucleotides of a lncRNAs selected from SEQ ID NOs 1 to 22, (b) a nucleic acid sequence which comprises or consists of a nucleotide sequence which is at least 70% identical to the complementary strand of one or more lncRNAs selected from SEQ ID NOs 1 to 22, (c) a nucleic acid sequence which comprises or consists of a nucleotide sequence according to (a) or (b), wherein U is replaced by T, (d) an expression vector expressing the nucleic acid sequence as defined in any one of (a) to (c), preferably under the control of a heart-specific promoter, or (e) a host comprising the expression vector of (d).

The nucleic acid sequences as defined in items (a) to (c) of this preferred embodiment comprise or consist of sequences that comprise or are complementary to nucleotides of a lncRNAs selected from SEQ ID NOs 1 to 22. Hence, these nucleic acid sequences comprise or are antisense nucleic acid sequences.

The molecule according to item (a) of this preferred embodiment of the invention comprises or consists of a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, or all 23 nucleotides of SEQ ID NOs 1 to 22. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of SEQ ID NOs 1 to 22, i.e. the nucleotides are consecutive in the respective SEQ ID NO.

The molecule according to item (a) is preferably a "siRNA". siRNAs are a class of 18 to 30, preferably 20 to 25, most preferred 21 to 23 or 21 nucleotide-long double-stranded RNA molecules that play a variety of roles in biology. Also preferably at least one RNA strand has a 5'- and/or 3'-overhang. Preferably, one or both ends of the double-strand have a 3'-overhang from 1-5 nucleotides, more preferably from 1-3 nucleotides and most preferably 2 nucleotides. In general, any RNA molecule suitable to act as siRNA is envisioned in the present invention. The most efficient silencing was so far obtained with siRNA duplexes composed of 21-nt sense and 21-nt antisense strands, paired in a manner to have 2-nt 3'-overhangs. The siRNA according to the invention comprises an antisense strand which comprises or consists of a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, or all 23 nucleotides of SEQ ID NOs 1 to 22. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of SEQ ID NOs 1 to 22, i.e. the nucleotides are consecutive in the respective SEQ ID NO.

The molecule according to item (a) is also preferably a "shRNA". shRNA preferably utilizes the U6 promoter for its expression. The shRNA according to the invention comprises or consists a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, or all 23 nucleotides of SEQ ID NOs 1 to 22. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of SEQ ID NOs 1 to 22, i.e. the nucleotides are consecutive in the respective SEQ ID NO.

An molecule according to item (b) of the above preferred embodiment of the invention is capable of interacting with, more specifically hybridizing with the target lncRNA. By formation of the hybrid the function of the lncRNA is reduced or blocked. Standard methods relating to such antisense technology have been described (see, e.g., Melani et al., Cancer Res. (1991) 51:2897-2901). The term "antisense molecule" in accordance with the present invention thus relates to a nucleic acid molecule, preferably a RNA molecule, that has a base sequence complementary to a given lncRNA, i.e. the "sense" sequence.

A particularly preferred example of the molecule according to item (b) is an Endoribonuclease-prepared siRNA (esiRNA).

The sequence identity of the antisense molecule according to item (b) to an lncRNA selected from SEQ ID NOs 1 to 22 is with increasing preference at least 75%, at least 80%, at least 85%, at least 90%, at least 95%, at least 98%, at least 99% and 100%. Means and methods for determining sequence identity are known in the art. Preferably, the BLAST (Basic Local Alignment Search Tool) program is used for determining the sequence identity with regard to one or more lncRNAs selected from SEQ ID NOs 1 to 22.

Antisense molecules, siRNAs and shRNAs of the present invention are preferably chemically synthesized using appropriately protected ribonucleoside phosphoramidites and a conventional RNA synthesizer. Suppliers of RNA synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK).

As discussed in greater detail herein above, the ability of antisense molecules, siRNA, and shRNA to potently, but reversibly, silence lncRNA and genes in vivo makes these molecules particularly well suited for use in the pharmaceutical composition of the invention.

The antisense molecules, siRNAs, shRNAs may comprise modified nucleotides such as locked nucleic acids (LNAs). LNA nucleotides can be mixed with DNA or RNA residues in the oligonucleotide whenever desired. Particularly, preferred example of siRNAs is GapmeR (LNA™ GapmeRs (Exiqon)). The GapmeRs are preferably 14-16 nucleotides in length and are optionally fully phosphorothioated.

Examples of suitable expression vector which may be used in connection with item (d) of the above-preferred embodiment have been detailed herein above.

In accordance with a preferred embodiment of the third and fourth aspect of the invention the compound as defined in (ii) is an aptamer, a ribozyme, an antibody, a protein drug, or a small molecule inhibitor.

The aptamer, ribozyme, antibody, protein drug, or small molecule inhibitor of this embodiment specifically bind to one or more lncRNA selected from SEQ ID NOs 1 to 22, thereby inhibiting the activity of one or more lncRNA selected from SEQ ID NOs 1 to 22. The terms "aptamer", "ribozyme", "antibody", "protein drug", and "small molecule inhibitor" have been defined herein above in connection with the first and second aspect of the invention and apply mutatis mutandis to the third and fourth aspect of the invention.

The present invention relates in a fifth aspect to a method for diagnosing hypoxia in a patient, comprising (a) detecting the expression level of one or more lncRNAs selected from SEQ ID NOs 1 to 42, preferably selected from SEQ ID NOs 1 to 3 and 14 in a sample obtained from said patient; and (b) comparing said expression level of the one or more lncRNAs with the expression level of these one or more lncRNAs in a sample obtained from healthy subjects, wherein a greater than 2-fold upregulation of one or more lncRNAs selected from SEQ ID NOs 1 to 22; and/or a greater than 2-fold downregulation of one or more lncRNAs selected from SEQ ID NOs 23 to 42 is indicative for hypoxia in the patient.

The method according to the fifth aspect of the invention may also encompass detecting and comparing the expression level of one or more lncRNAs being with increased preference at least 90%, at least 92%, at least 94%, at least 96%, at least 98%, at least 99%, and at least 99.5% identical to any one of SEQ ID NOs 1 to 22 and/or 23 to 42. Means and methods for determining sequence identity are known in the art. Preferably, the BLAST (Basic Local Alignment Search Tool) program is used for determining the sequence identity with regard to one or more lncRNAs selected from SEQ ID NOs 1 to 22 and/or 23 to 42. The method according to the fifth aspect of the invention may furthermore encompass detecting and comparing the expression level of one or more lncRNAs differing with increasing preference by no more than 10, such as 5, 4, 3, 2 or 1 nucleotide(s) from any one of SEQ ID NOs 1 to 22 and/or 23 to 42. The nucleotide differences may be the addition, deletion and/or substitution of nucleotide(s). The sequences the expression of which is compared, while being homologous, may also differ from each other with increasing preference by no more than 10, such as 5, 4, 3, 2 or 1 nucleotide(s).

The term "hypoxia" designates a pathological condition in which the body or a region of the body is deprived of an adequate oxygen supply. Hypoxia may be classified as either generalized, affecting the whole body, or local, affecting a region of the body. Hypoxia occurs in tumors. Tumor hypoxia is the situation where tumor cells have been deprived of oxygen. As a tumor grows, it rapidly outgrows its blood supply, leaving portions of the tumor with regions where the oxygen concentration is significantly lower than in healthy tissues. Ischemia, meaning insufficient blood flow to a tissue, also results in hypoxia. Hence, the above method is preferably used for diagnosing tumor hypoxia and/or ischemic hypoxia.

The term "sample" designates a tissue sample or a body fluid sample. The body fluid sample is preferably selected from blood, serum, plasma, urine, salvia, amniotic fluid, cerebrospinal fluid and lymph. The tissue sample is preferably an organ sample, such as a heart, liver or kidney sample. Because in the examples provided herein below the expression of the lncRNA has been detected in Human Umbilical Vein Endothelial Cells (HUVECs) the sample preferably comprises or consists of endothelial cells, or at least comprises the lncRNAs from endothelial cells. More preferably the sample comprises or consists of human endothelial cells, or at least comprises the lncRNAs from human endothelial cells. The sample comprises in general the lncRNA of whole cells but may also only comprise the lncRNA of the cytoplasmic compartment or the nuclear compartment. The examples herein below exemplarily show for the lncRNAs DSCAM-1 and PLAC1-1 that lncRNA expression can be detected in the cytoplasmic compartment as well as the nuclear compartment (see FIGS. 3 and 11). In case the sample only comprises the lncRNAs of a particular cellular compartment, the cytoplasmic compartment is preferred. As far as the method is applied to a body fluid sample it is to be understood that the expression level of an lncRNA corresponds to the concentration of the lncRNA, because lncRNAs are not directly expressed in the body fluid but secreted from the cells, said cells expressing the lncRNAs, into the body fluids.

The "patient" or "subject" referred to herein is human.

The term "detecting the expression level of lncRNA" means determining the amount or yield of the lncRNA. The lncRNAs are initially expressed within a cell. It was found in accordance with the present invention that the lncRNAs of SEQ ID NOs 1 to 22 and/or 23 to 42 can be detected in the sample of a patient, in particular in various tissues including heart tissue. An lncRNA being "expressed in a sample" is therefore a lncRNA whose expression level can be detected in the sample by means and methods being further detailed herein below. An ncRNA is upregulated in a test sample if the amount or yield of the ncRNA is significantly greater as compared to the amount or yield of the corresponding ncRNA in a control sample. Likewise, an ncRNA is downregulated in a test sample if the amount or yield of the ncRNA is significantly less as compared to the amount or yield of the corresponding ncRNA in a control sample. In this context the term "corresponding ncRNA" means, for example, that the expression level of the lncRNA of SEQ ID NO: 1 in the test sample is compared to the expression level of the lncRNA of SEQ ID NO: 1 in the control sample, or likewise that the expression level of the lncRNA of SEQ ID NO: 2 in the test sample is compared to the expression level of the lncRNA of SEQ ID NO: 2 in the control sample. This applies mutatis mutandis for scenarios where the expression of more than one lncRNA selected from SEQ ID NOs 1 to 22 and/or 23 to 42 is determined. For instance, if the expression level of all lncRNAs of SEQ ID 1 to 22 and/or 23 to 42 is determined in the test sample it is compared to the expression level of all lncRNAs of SEQ ID NOs 1 to 22 and/or 23 to 42 in the control sample.

The expression level in the samples can be quantified by any suitable means and methods available from the art. In general relative and absolute quantification means and methods can be used. In absolute quantification no known standards or controls are needed. The expression level can be directly quantified. As well-known in the art, absolute quantification may rely on a predetermined standard curve. In relative quantification the expression level is quantified relative to a reference (such as known control expressions levels). Also in the absence of controls, one can relatively quantify the expression level when comparing e.g. fluorescence intensities.

Methods to assess RNA concentration may, for example, comprise measuring the fluorescence intensity of dyes that bind to nucleic acids and selectively fluorescence when bound. Such methods comprise a reverse transcription reaction and the production of cDNA, wherein the amount of the cDNA is determined thereby indirectly determining the amount of the RNA. The fluorescent-based method is particularly useful for cases where the RNA concentration is too low to accurately assess some with spectrophotometry and/ or in cases where contaminants absorbing at 260 nm make accurate quantification by spectrophotometry difficult or impossible.

When comparing the expression level of the one or more lncRNAs between different samples reliability of the comparison is preferably improved by including an invariant endogenous control (expression of a reference gene) to correct for potential sample to sample variations. Such normalization with respect to an invariant endogenous control is routinely performed in the art. For example, means and methods for expression level normalization, e.g. in real-time RT-PCR (see, for example, Bustin, Journal of Molecular Endocrinology, (2002) 29, 23-39) or micro-array expression analysis (see, for example, Calza and Balwitan, Methods Mol Biol. 2010; 673:37-52) are well-established. Also methods for normalization of the expression levels of small RNA sequences are established (see, for example, Mestdagh et al. (2009) Genome Biol.; 10(6):R64). In case RT-PCR or a micro-array is used to determine the expression levels in accordance with the present invention, the expression levels are preferably normalized to a spiked-in RNA (see, for example, McCormick et al. (2011), Silence, 2:2). Known amounts of a spiked-in RNA are mixed with the sample during preparation. More preferably the RNA is externally spiked-in to plasma and/or serum before the RNA isolation process is carried out, in which case the samples are plasma and/or serum. The spiked-in RNA technology is well-known and commercial kits are available from a number of manufacturers. The spiked-in RNA is preferably a spiked-in C. elegans RNA.

As evident from the examples herein below, the deregulation of the levels of one or more lncRNAs selected from 1 to 22 and/or 23 to 42, are indicative for hypoxia. Thus, determining the expression levels of one or more lncRNAs selected from 1 to 22 and/or 23 to 42 can be expected to be of prognostic value for diagnosing a hypoxia in a patient. The lncRNAs selected from 1 to 22 and/or 23 to 42 may be combined with further diagnostic markers for hypoxia in order to enhance the confidentially of the diagnostic method. High-expression level of the lncRNAs selected from 1 to 22 and low expression level of the lncRNAs selected from 23 to 42 is indicative for hypoxia.

In the examples herein below the primer sequences of SEQ ID NOs 45 to 52 were employed in order to detect the expression level of the three different isoforms of DSCAM-1 (SEQ ID NOs 1 to 3) and PLAC1-1, wherein the uneven numbers are forward primers and the even numbers are reverse primers. Consecutive numbers, such as SEQ ID NOs 45 and 46, SEQ ID NOs 47 and 48 etc. are a primer pair. As defined herein, SEQ ID NO: 1 is the isoform 3, SEQ ID NO: 2 is the isoform 2, and SEQ ID NO: 3 is the isoform 1 of DSCAM-1. The primer pair of SEQ ID NOs 45/46 is for the detection of the expression level of isoform 1 of DSCAM-1, SEQ ID NOs 47/48 is for isoform-2 of DSCAM-1, and SEQ ID NOs 49/50 is for isoform-3 of DSCAM-1. The primer pair of SEQ ID NOs 51/52 is for the detection of the expression level of the lncRNA PLAC1-1 (SEQ ID NO: 14).

One or more of these primer pairs are preferably used in the diagnostic method according to the third aspect of the invention. One or more of these primer pairs are likewise preferably incorporated into the kit of the invention being described herein below.

The greater than 2-fold downregulation is with increasing preference greater than 3-fold downregulation, greater than 4-fold downregulation, greater than 5-fold downregulation, greater than 6-fold downregulation, greater than 7-fold downregulation and greater than 8-fold downregulation. Likewise the greater than 2-fold upregulation is with increasing preference greater than 3-fold upregulation, greater than 4-fold upregulation, greater than 5-fold upregulation, greater than 6-fold upregulation, greater than 7-fold upregulation and greater than 8-fold upregulation. The higher thresholds for the up- and downregulation may increase the reliability of the method of the third aspect of the invention.

In accordance with a preferred embodiment of the fifth aspect of the invention the sample is a blood sample or blood-derived sample.

The blood-derived sample is preferably plasma or serum.

In accordance with another preferred embodiment of the fifth aspect of the invention the sample is a tissue sample. The tissue sample comprises preferably heart tissue, and more preferably ECs of the heart.

In accordance with a further preferred embodiment of the fifth aspect of the invention the detection of the expression level of the one or more lncRNAs comprises (a) quantitative PCR, preferably quantitative real time PCR, or (b) a template/RNA amplification method followed by determining the expression level of the one or more lncRNAs using a fluorescence- or luminescence-based quantification method.

In quantitative PCR (qPCR), the amount of amplified product is linked to fluorescence intensity using a fluorescent reporter molecule. The point at which the fluorescent signal is measured in order to calculate the initial template quantity can either be at the end of the reaction (endpoint semi-quantitative PCR) or while the amplification is still progressing (real-time qPCR).

In endpoint semi-quantitative PCR, fluorescence data are collected after the amplification reaction has been completed, usually after 30-40 cycles, and this final fluorescence is used to back-calculate the amount of template present prior to PCR.

The more sensitive and reproducible method of real-time qPCR measures the fluorescence at each cycle as the amplification progresses. This allows quantification of the template to be based on the fluorescence signal during the exponential phase of amplification, before limiting reagents, accumulation of inhibitors, or inactivation of the polymerase have started to have an effect on the efficiency of amplification. Fluorescence readings at these earlier cycles of the reaction will measure the amplified template quantity where the reaction is much more reproducible from sample to sample than at the endpoint.

A non-limiting example of a template/RNA amplification method followed by determining the expression level of the one or more lncRNAs using a fluorescence- or luminescence-based quantification method is a method combining transcription mediated amplification (TMA) and a hybridization protection assay (HPA). In more detail, such a method may comprise hybridizing one or more oligonucleotides ("capture oligonucleotides") that are complementary to any of SEQ ID NOs 1 to 22 or 23 to 42. In case two or more of SEQ ID NOs 1 to 22 and 23 to 42 are targeted, a separate capture oligonucleotides is used for each sequence selected from 1 to 22 and 23 to 42. The hybridized target sequences are then captured onto magnetic microparticles that are separated from the sample in a magnetic field. Wash steps may be utilized to remove extraneous components. Target amplification typically occurs via TMA, which is a transcription-based nucleic acid amplification method that utilizes two enzymes, Moloney murine leukemia virus (MMLV) reverse transcriptase and T7 RNA polymerase. A unique set of primers is used for each target sequence selected from 1 to 22 and 23 to 42. The reverse transcriptase is used to generate a DNA copy (containing a promoter sequence for T7 RNA polymerase) of the target sequence. T7 RNA polymerase produces multiple copies of RNA amplicon from the DNA copy. Detection of lncRNA expression level is achieved by HPA using single-stranded, chemiluminescent-labeled nucleic acid probes that are complementary to the one or more amplicon. Preferably, distinguishably labelled probes are used for each target amplicon. The labeled nucleic acid probes hybridize specifically to the amplicon. A "selection reagent" then differentiates between hybridized and unhybridized probes by inactivating the label on unhybridized probes. During the detection step, the chemiluminescent signal produced by the hybridized probe is measured in a luminometer and is reported as "Relative Light Units" (RLU), thereby quantifying the lncRNA expression level.

In accordance with a still further preferred embodiment of the fifth aspect of the invention the method comprises prior to the detection of the expression level of the long non-coding RNA a pre-amplification step of the RNA within the test patient's sample and/or the control patient's sample.

Performing a pre-amplification step is of particular advantage in case only a low amount of (test and/or control) sample is available. The pre-amplification step allows increasing the amount of RNA within the sample before proceeding to the analysis of the expression level. Means and methods for the pre-amplification of RNA are well known in the art (see, e.g., Vermeulen et al (2009) BMC Res Notes., 2:235). In case both the RNA in the test and control sample is pre-amplified preferably the same method for the pre-amplification step is used such that the relative amount of RNA of the test sample as compared to the control sample is maintained. In case only the RNA of the test or control sample is pre-amplified or the two RNA samples are pre-amplified by different methods, the expression level data may have to be normalized for pre-amplification step; see, e.g. Mestdagh et al. (2009), *Genome Biology* 2009, 10:R64.

The present invention relates in a sixth aspect to a kit for diagnosing hypoxia in a patient, said kit comprising means for the detection of the expression level of one or more lncRNAs selected from SEQ ID NOs 1 to 42, preferably selected from SEQ ID NOs 1 to 3 and 14 and instructions how to use the kit.

The instructions how to use the kit preferably inform inter alia that high-expression level of the lncRNAs selected from 1 to 22 and low expression level of the lncRNAs selected from 23 to 42 is indicative for hypoxia.

The means for the detection of the expression level of one or more lncRNAs selected from SEQ ID NOs 1 to 22 and 23 to 42 are preferably the means required for (i) a quantitative PCR, preferably quantitative real time PCR, or (ii) a template/RNA amplification method followed by determining the expression level of the one or more lncRNAs using a fluorescence- or luminescence-based quantification method. These means have been further detailed herein above in connection with the fifth aspect of the invention, and may be comprised in the kit. Hence, the means preferably comprise oligonucleotides, such as fluorescent hybridization probes or primers, which specifically hybridize to one or more lncRNAs selected from SEQ ID NOs SEQ ID NOs 1 to 22 and 23 to 42. Additional ingredients of the kits may be florescent or luminescent dyes, preferably coupled to said oligonucleotides. Also, additional ingredients of the kits may be enzymes, such as a reverse transcriptase and/or a polymerase.

In accordance with the kit of the invention the means for the detection of the expression level of one or more lncRNAs selected from SEQ ID NOs SEQ ID NOs 1 to 22 and 23 to 42 preferably comprise means for the detection of the lncRNA of SEQ ID NOs 1 to 3.

The various components of the kit may be packaged in one or more containers such as one or more vials. The vials may, in addition to the components, comprise preservatives or buffers for storage.

In accordance with a preferred embodiment of the sixth aspect of the invention, the means are primer pairs used for the specific detection of the expression level of one or more lncRNAs selected from SEQ ID NOs SEQ ID NOs 1 to 22 and 23 to 42.

In accordance with a preferred embodiment of all six aspects of the invention the one or more lncRNAs are at least 3 lncRNAs, and preferably at least 5 lncRNAs.

Employing at least 3 lncRNAs, preferably at least 5 lncRNAs, more preferably at least 10 lncRNAs, even more preferably at least 20 lncRNAs and most preferably all lncRNAs of SEQ ID NOs 1 to 22 and 23 to 42 will additionally increase the effectively of the pharmaceutical compositions, medical uses, methods and kits of the invention. Employing these numbers of lncRNAs may balance potential differences associated with particular compounds, probes or methods used in connection with the methods and kits of the invention. In the pharmaceutical compositions and medical uses of the invention these numbers of lncRNAs may increase the beneficial effect for the subject to be treated.

In accordance with a preferred embodiment of all six aspects of the invention the one or more lncRNAs is or comprises the lncRNA of SEQ ID NO: 1.

As discussed herein above SEQ ID NO: 1 is the lncRNA DSCAM-1 isoform 3. The pro-angiogenic nature of lncRNA DSCAM-1 isoform 3 is demonstrated in the example herein by expression profiling and over-/under-expression experiments in HUVEC cells.

The figures show.

Figure 1:
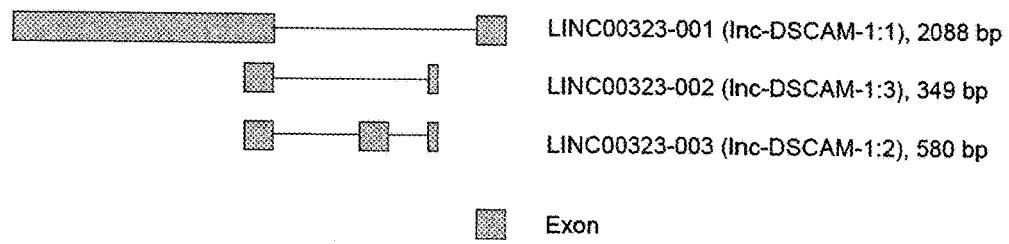

FIG. 1: The three isoforms of the lncRNA DSCAM-1 (also designated herein LINC00323 or lnc323 or HSLINCR).

FIG. 2: (A) Differential lncRNA expression after hypoxia in HUVECs (RNA-sequencing data). (B) HUVECs treated with VEGF (50 ng/ml) for 24 h. N=3.

FIG. 3: Validation of NCode array data for lnc-DSCAM-1 (LINC00323) in fractionated RNA.

FIG. 4: Tissue distribution of lnc-DSCAM-1 (LINC00323).

Figure 5:
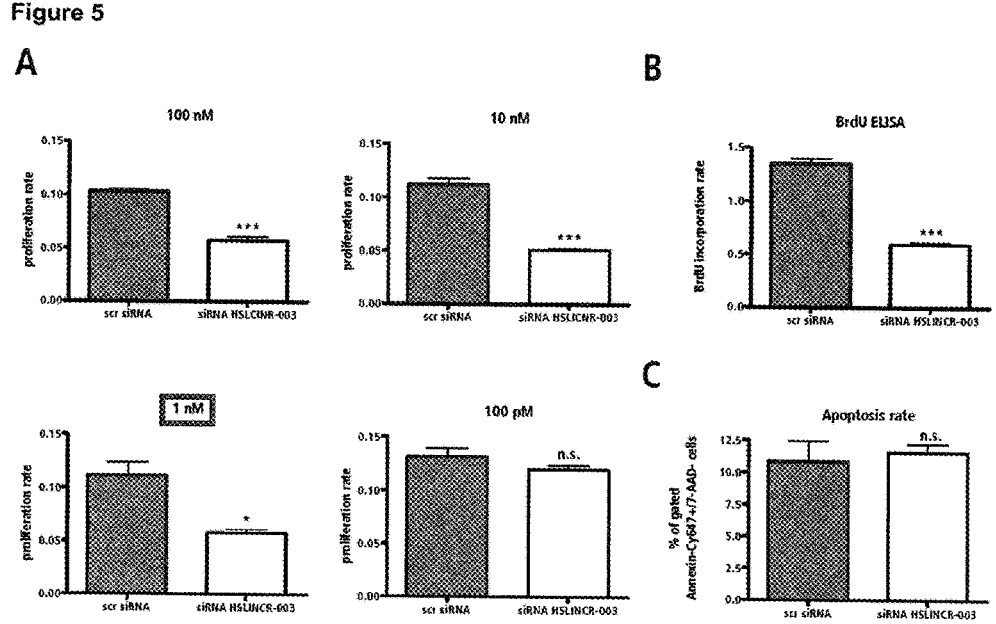

FIG. 5: siRNA against lnc-DSCAM-1 isoform 3 (HSLINCR-003, SEQ ID NO: 1) impairs HUVEC proliferation.

FIG. 6: Downstream signalling triggered by loss of lnc-DSCAM-1 isoform 3 (HSLINCR-003).

Figure 7:
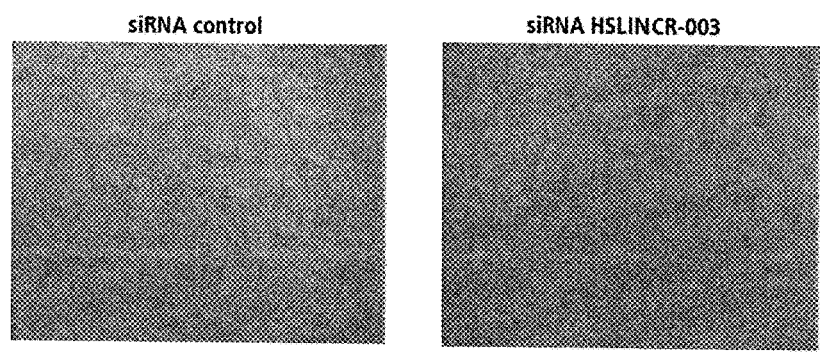
Figure 7:
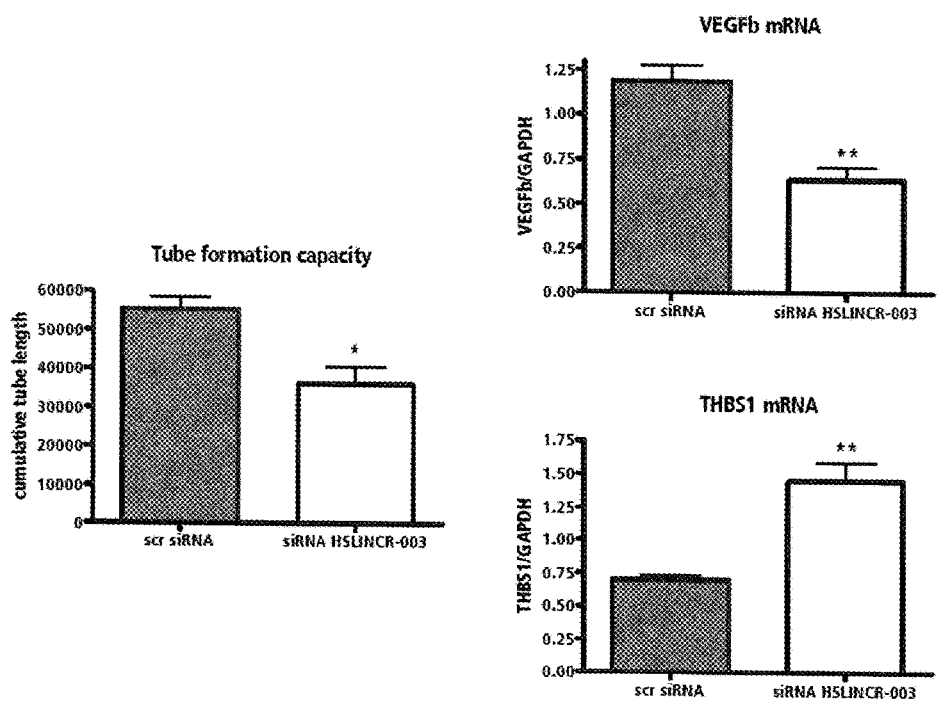

FIG. 7: Effect of lnc-DSCAM-1 isoform 3 (HSLINCR-003) knockdown on capillary growth.

Figure 8:
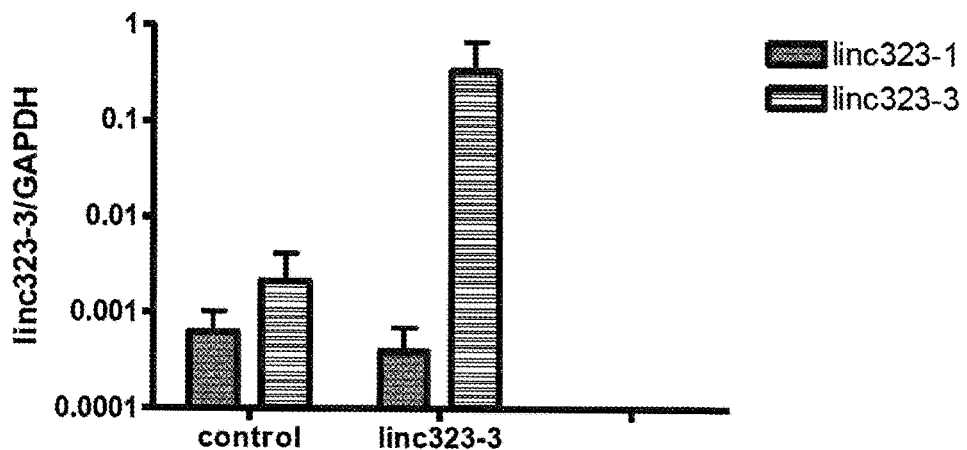

FIG. 8: Overexpression of lnc-DSCAM-1, isoforms 1 and 3 (linc323-1 and linc323-3) in the human endothelial cell line Ea.Hy926.

Figure 9:
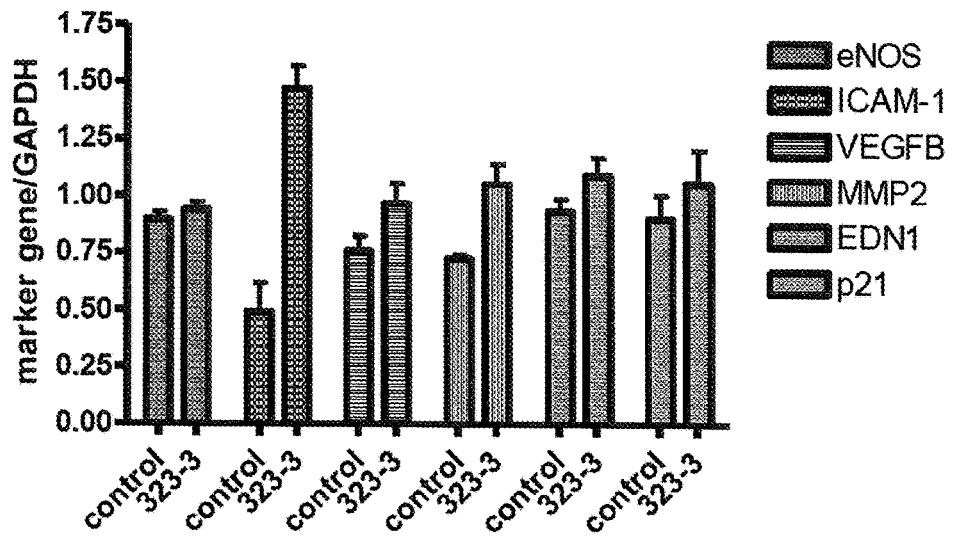

FIG. 9: Angiogenic gene expression pattern upon overexpression of lnc-DSCAM-1 isoform 3 (linc323-3) in the human endothelial cell line Ea.Hy926.

Figure 10:
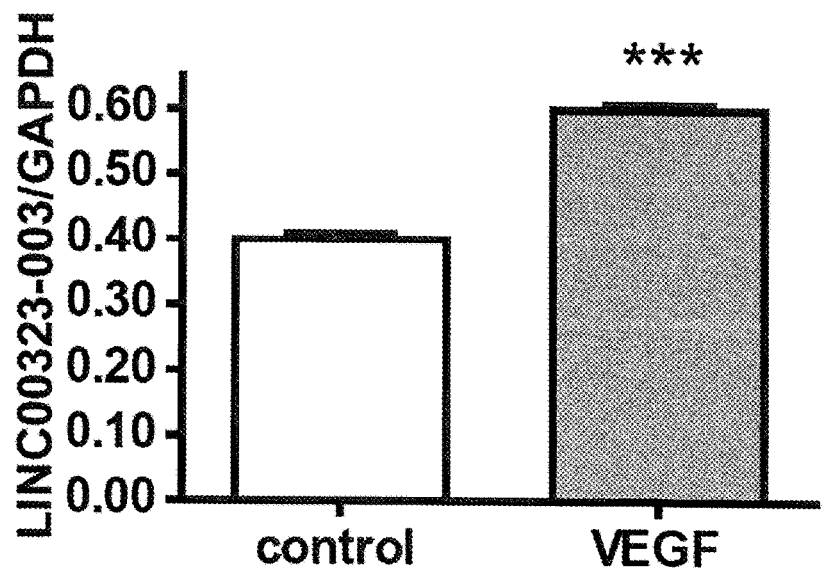

FIG. 10: Endothelial lncRNA lnc-DSCAM-1 isoform 3 (LIN000323-003; SEQ ID NO: 1) expression is crucial for endothelial cellular function. HUVECs treated with VEGF (50 ng/ml) for 24 h. N=3.

Figure 11:
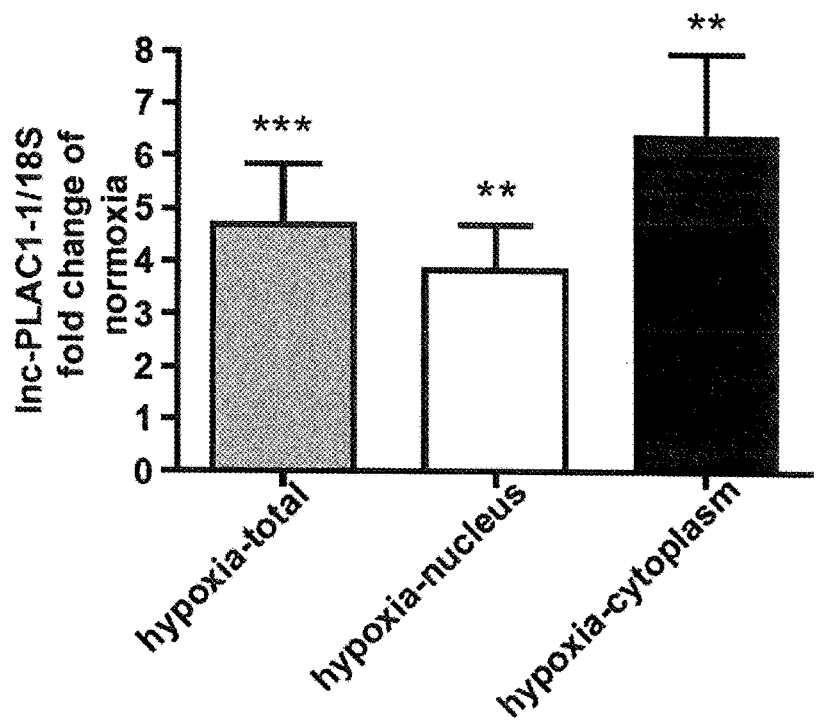

FIG. 11: Validation of the lncRNA lnc-PLAC1-1 (SEQ ID NO: 14) in subcellular RNA (total, nuclear, cytoplasmic) from HUVECs subjected to normoxia and hypoxia. Fold-change of normoxia is plotted. N=3/4. *=p<0.05, =p<0.01, *=p<0.001

FIG. 12: Endothelial lncRNA lnc-PLAC1-1 (SEQ ID NO: 14) is transcriptionally regulated with miR-503 after hypoxia and its loss deteriorates HUVEC function. (A) Genomic localization of lnc-PLAC1-1, adapted from NCBI Map Viewer. (B) Primary transcript of miR-503 (pri-miR-503) and processed, mature miR-503 are upregulated after 24 h hypoxia in HUVECs determined by qRT-PCR. N=4. (C) GapmeR-mediated knockdown of the lncRNA lnc-PLAC1-1 efficiently lowers endogenous expression level in HUVECs detected by qRT-PCR. N=3. (D) Loss of lnc-PLAC1-1 causes impairment in BrdU incorporation rate monitored by ELISA. N=3. (E) Scratch wound closure is impaired when the lncRNA lnc-PLAC1-1 is silenced in HUVEC. N=3. (F) Increase in cell cycle inhibitor p21 expression detected by qRT-PCR. N=3. (G) GapmeR against the lncRNA lnc-PLAC1-1 represses GATA2 on protein level. N=4. (H) Migration index is improved in transgenic Ea.Hy926 cells overexpressing LINC00323-003 and lnc-PLAC1-1 as compared to the control. N=5. *=p<0.05, =p<0.01, *=p<0.001

The examples illustrate the invention.

EXAMPLE 1

Identification of Hypoxia-Sensitive lncRNAs

It was studied if long non-coding RNAs (lncRNAs) would be differentially expressed after hypoxic treatment in human umbilical vein endothelial cells (HUVECs). For RNA deep sequencing analysis total RNA derived from human umbilical vein endothelial cells (HUVECs) that underwent in vitro cultivation under normoxic or hypoxic (0.2% $O_2$) conditions for 24 h was generated. Taking into account biological variations within the groups, N=3 per group for HUVECs were employed.

Hypoxia-sensitive non-coding RNA (ncRNA) expression was detected via two approaches; (a) microarray- and (b) RNA-sequencing (RNA-seq) techniques.

NCode (Invitrogen) microarray was performed to analyze differential expression of noncoding RNA during hypoxia of human umbilical vein endothelial cells (HUVECs). Evaluation of this data revealed appearance of hypoxia-sensitive lncRNAs (FIG. 2A). These lncRNAs are shown in Table 1 and SEQ ID NOs 1 to 42 of the application as filed. The hypoxia-sensitive lncRNAs are significantly deregulated under hypoxic conditions. SEQ ID NOs 1 to 22 were found to be upregulated, while EQ ID NOs 1 to 22 were found to be downregulated.

TABLE 1

Hypoxia-sensitive lncRNAs

| lncRNA name | feature length | baseMean | log2FoldChar | pvalue | padj |
|---|---|---|---|---|---|
| lnc-WDR74-1 | 3756 | 1175.3957 | −1.4277703 | 7.94E−94 | 5.67E−91 |
| lnc-SAMD14-2 | 4290 | 1266.7685 | −0.9997163 | 7.25E−96 | 6.21E−93 |
| lnc-AKR1C2-4 | 4450 | 1561.2652 | −0.9389733 | 3.14E−69 | 1.28E−66 |
| lnc-SEBOX-2 | 2662 | 1722.7503 | −0.9144215 | 4.12E−71 | 1.96E−68 |
| lnc-C9orf69-1 | 3389 | 1462.7341 | −0.9012412 | 1.20E−44 | 2.45E−42 |
| lnc-SERPINC1-1 | 3631 | 1809.521 | −0.7581272 | 5.52E−19 | 3.94E−17 |
| lnc-GJA10-3 | 9544 | 1416.5181 | −0.7563964 | 1.03E−69 | 4.64E−67 |
| lnc-ANKRD12-l | 1050 | 1229.3493 | −0.7283248 | 1.89E−22 | 1.60E−20 |
| lnc-MRPS25-1 | 5131 | 4034.2832 | −0.5751249 | 2.04E−88 | 1.34E−85 |
| lnc-B3GAT2-3 | 6609 | 1065.9363 | −0.4584332 | 7.04E−25 | 6.34E−23 |
| lnc-C6orf146-3 | 7070 | 1845.0425 | 0.4459623 | 2.89E−30 | 3.75E−28 |
| lnc-DLK1-4 | 13388 | 9850.0601 | 0.5521516 | 2.80E−122 | 3.42E−119 |
| lnc-IDS-1 | 4581 | 1341.6273 | 0.563006 | 9.63E−50 | 2.84E−47 |
| lnc-ZCCHC7-2 | 4375 | 1363.4439 | 0.6099449 | 2.86E−41 | 5.10E−39 |
| lnc-AK1-1 | 1160 | 1363.16 | 0.8456338 | 1.10E−56 | 3.92E−54 |
| lnc-C14orf166B-1 | 721 | 1312.6298 | 0.9946821 | 2.96E−42 | 5.64E−40 |
| lnc-LCN6-1 | 4345 | 1649.2145 | 1.0725203 | 5.15E−35 | 7.36E−33 |
| lnc-FN1-3 | 5628 | 7159.3619 | 1.1548762 | 0 | 0 |
| lnc-PLAC1-1 | 1678 | 1049.2302 | 2.141139 | 1.04E−261 | 2.96E−258 |
| lnc-TMEM30B-5 | 533 | 439.7136 | 5.09995 | 1.25E−158 | 2.68E−155 |
| lnc-C11orf35-2 | 2321 | 136.0999 | 4.0410731 | 2.19E−55 | 7.46E−53 |

TABLE 1-continued

Hypoxia-sensitive lncRNAs

| lncRNA name | feature length | baseMean | log2FoldChar | pvalue | padj |
|---|---|---|---|---|---|
| lnc-ATXN7-8 | 7232 | 244.68909 | 3.0583206 | 6.07E−79 | 3.71E−76 |
| lnc-ARRDC3-1 | 11246 | 109.93138 | 3.033384 | 5.37E−59 | 2.00E−56 |
| lnc-BLCAP-1 | 2138 | 601.59313 | 2.7153192 | 3.54E−128 | 5.06E−125 |
| lnc-ACER2-1 | 1965 | 702.82234 | 2.655259 | 1.06E−274 | 4.54E−271 |
| lnc-JAK1-1 | 4326 | 113.11347 | 2.6471848 | 3.13E−47 | 7.89E−45 |
| lnc-AC021860.1-2 | 3101 | 114.24598 | 2.4725645 | 3.95E−47 | 9.67E−45 |
| lnc-PTTG1-1 | 2301 | 158.884 | 2.340892 | 2.08E−51 | 6.35E−49 |
| lnc-PLOD2-2 | 2095 | 292.66698 | 2.3222268 | 2.29E−102 | 2.18E−99 |
| lnc-POLR1E-1 | 1571 | 88.112301 | −1.815099 | 1.88E−27 | 2.13E−25 |
| lnc-KIAA0513-2 | 777 | 43.331816 | −1.8986651 | 7.10E−13 | 3.09E−11 |
| lnc-EPCAM-1 | 13458 | 91.303344 | −1.9138273 | 9.79E−18 | 6.40E−16 |
| lnc-DRD5-10 | 2449 | 71.845142 | −1.9563842 | 3.10E−27 | 3.45E−25 |
| lnc-ACOT1-2 | 2428 | 397.2283 | −1.9701526 | 7.03E−116 | 7.52E−113 |
| lnc-PGRMC2-1 | 1623 | 276.22509 | −2.3054837 | 3.86E−94 | 3.00E−91 |
| lnc-ZNF276-1 | 1753 | 77.561264 | −2.4417613 | 4.24E−29 | 5.18E−27 |
| lnc-CTD-2517M22.14.1-2 | 4248 | 494.95654 | −2.5229731 | 2.40E−138 | 4.11E−135 |
| lnc-TBC1D12-1 | 645 | 88.433128 | −2.8220783 | 3.51E−39 | 5.78E−37 |
| lnc-HMOX1-1 | 557 | 57.6028 | −3.4966215 | 2.18E−37 | 3.33E−35 |
| lnc-DSCAM-1 | 2432 | 29.239401 | 2.1091475 | 6.09E−12 | 2.46E−10 |

Moreover, RNA-seq data identified 774 (404 up, 371 down) significantly deregulated lncRNAs (FIG. 2B). In order to obtain the RNA-seq data 2 µg of total RNA— isolated from HUVEC cells cultured under normoxic or hypoxic conditions, respectively for 24 h—was subjected to RNA-Seq analysis (N=3). After extracting the total RNA from the samples, rRNA was removed from the total RNA. By using the fragmentation buffer, the remaining RNA was fragmented into short fragments. The first strand cDNA was synthesized by random hexamer-primer using the remaining RNA fragments as templates. Buffer, dNTPs, RNase H and DNA polymerase I were added to synthesize the second strand. The double strand cDNA was purified with QiaQuick PCR extraction kit and washed with EB buffer for end repair and poly (A) addition. Finally, sequencing adaptors were ligated to the fragments. The fragments were purified by agarose gel electrophoresis and enriched by PCR amplification. The library products were sequenced via Illumina HiSeq™ 2000.

The log 2-fold expression changes derived from the two different technologies—NCode (Invitrogen) microarray data and RNA-seq data—were significantly correlated both for lncRNAs (Pearson correlation coefficient: 0.43; p-value<2.2e-16) and for protein-coding genes (Pearson correlation coefficient: 0.74; p-value<2.2e-16). RNA-Seq also confirmed enhanced expression of LINC00323 (lnc-DSCAM-1) under hypoxia. In addition, from the RNA-Seq data another hypoxia-sensitive lncRNA lnc-PLAC1-1 (SEQ ID NO: 14 or MIR503HG-002) was identified based on the following criteria: (a) minimal 4-fold upregulation, (b) base mean>1000, and c) intergenic annotation. Based on these stringent criteria lnc-PLAC1-1 was identified as high propriety candidate. The subsequent validation experiments being described in the following examples 2 and 3 confirm the hypoxia-dependent upregulation of the two microarray- or RNA-seq derived lncRNAs LINC00323 and lnc-PLAC1-1.

EXAMPLE 2

Functional Experiments Followed to Decipher Endothelial Function of the lncRNA DSCAM-1 (LINC00323 or HSLINCR)

As can be taken from Table 1 the long intergenic non-coding RNA (LINCRNA) 323 was upregulated in the microarray data. DSCAM-1 has three transcript variants (lncRNA323-1 (SEQ ID NO: 3), lncRNA323-2 (SEQ ID NO: 2), and lncRNA323-3 (SEQ ID NO: 1)).

HUVECs were cultured under normoxic or hypoxic (0.2% O2, 24 h) conditions and total RNA was analyzed by microarray and next generation RNA-sequencing analysis (see Example 1). Total RNA was fractionated to a cytoplasmic and nuclear fraction and expression levels of hypoxiasensitive lncRNAs were validated via qPCR. Loss-of-function-experiments using siRNA against specific lncRNAs was applied to determine proliferation, apoptosis, capillary tube formation and gene or protein expression analysis. Gain-of-function-approaches via lentiviral delivery was applied to characterize functional lncRNA overexpression.

EXAMPLE 2.1 qPCR Analysis of Endothelial lnc-DSCAM-1 Transcripts

Endothelial lnc-DSCAM-1 transcripts were validated to be hypoxia-sensitive via qPCR analysis. Of note, endothelial lnc-DSCAM-1 transcript expression was upregulated in the cytoplasmic RNA fraction after hypoxia. N=3 experiments per group (FIG. 3).

EXAMPLE 2.2

Tissue Distribution of Lnc-DSCAM-1 Transcripts

Human lnc-DSCAM-1 transcript variants were detected in several organ tissues. DSCAM-1 is ubiquitously expressed with highest expression in vascularized tissue such as kidney or lung (FIG. 4). Of note, DSCAM-1 transcript 2 (SEQ ID NO: 2) is not expressed in every tissue.

EXAMPLE 2.3 siRNA Against Lnc-DSCAM-1 Isoform 3 lnc-DSCAM-1 isoform 3 (LINC00323-003, HSLINCR-003, SEQ ID NO: 1) knockdown deteriorates HUVEC function by inhibiting proliferative pathways. (FIG. 5A)

WST1-activity is reduced in HSLINCR siRNA-transfected HUVECs. (FIG. 5B) BrdU incorporation rate is impaired in DSCAM-1 isoform 3-deficient HUVECs. (FIG. 5C) HSLINCR (LINC00323-003) loss has no effect on apoptosis rate. N=3 experiments per group. *=p<0.05, ***=p<0.001.

EXAMPLE 2.4

Downstream Signalling Triggered by Loss of Lnc-DSCAM-1

(FIG. 6A) Growth factor-related ERK/Akt signalling is decreased by low lnc-DSCAM-1 (LINC00323-003, HSLINCR) expression contributing to the defective functional phenotype. Representative Western Blot is shown. (FIG. 6B) Cell cycle inhibitors p21 and p27 are upregulated after siRNA against DSCAM-1 (LINC00323-003). (FIG. 6C) Pro-angiogenic GATA2 and SIRT1 are repressed after loss of DSCAM-1 (LINC00323-003). N=3/4 experiments per group. *=p<0.05, **=p<0.01

EXAMPLE 2.5 lnc-DSCAM-1 Knockdown and Capillary Growth

Lnc-DSCAM-1 isoform 3 (LINC00323-003, HSLINCR-003) knockdown inhibits capillary growth (FIG. 7). (FIG. 7A) Endogenous modulation of HSLINCR (LINC00323-003) triggers angiogenic defects in a matrigel-based tube forming assay. (FIG. 7B) Pro- and anti-angiogenic cytokines VEGFB and THBS1 are affected by lnc-DSCAM-1 modulation. N=3 experiments per group. *=p<0.05, **=p<0.01

EXAMPLE 2.6 lnc-DSCAM-1 Overexpression Studies in Human Endothelial Cell Line Ea.Hy926 lnc-DSCAM-1 isoform 3(LINC00323-003) transcripts were cloned into a lentiviral backbone to generate viral particles for overexpression studies.

qPCR analysis was performed to study lnc-DSCAM-1 (being a LINCRNA) overexpression. FIG. 8 shows the lnc-DSCAM-1, isoforms 1 and 3 expression rate in human endothelial cell line Ea.Hy926.

EXAMPLE 2.7

Angiogenic Gene Expression Pattern Upon Overexpression of lnc-DSCAM-1, Isoform 3

Angiogenic gene expression pattern in human endothelial cell line Ea.Hy926 constitutively overexpressing lnc-DSCAM-1, isoform 3 in comparison to control cells.

EXAMPLE 2.8

VEGF-Dependent Induction of Lnc-DSCAM-1 Expression

VEGF treatment increased lnc-DSCAM-1, isoform 3 (LINC00323-003) expression (FIG. 10).

EXAMPLE 3

Functional Experiments Followed to Decipher Endothelial Function of the lncRNA lnc-PLAC1-1 (MIR503HG-002, NONHSAT138623 or NR_024607)

EXAMPLE 3.1

Hypoxia-Dependent Enhanced Expression of lnc-PLAC1-1 in the Nuclear and Cytoplasmic Compartment Cell compartment-specific RNA analysis revealed hypoxia-dependent enhanced expression, of lnc-PLAC1-1 in both the nuclear and cytoplasmic compartment (FIG. 11). High purity of subcellular compartment preparations was proven by screening expression of the nuclear enriched lncRNA XIST.

EXAMPLE 3.2

Endothelial Functions of Hypoxia-Sensitive lncRNA lnc-PLAC1-1

The RNA-seq derived lncRNA PLAC1-1 is located at chromosome X, harbors a coding sequence of miR-503 and is adjacent to miR-424 (FIG. 12A). Indeed, analysis of pri-miR-503 and mature miR-503 expression after hypoxia showed a similar increase of expression reflecting same regulatory mechanisms for transcriptional activation (FIG. 12B). Both miR-503 and the lncRNA PLAC1-1 modulations had different effects on endothelial cell function; whereas transfection of miR-503 precursors resulted in negative effects on endothelial cell viability, knockdown of lnc-PLAC1-1 suppressed endothelial proliferation independent of alterations of apoptosis (FIGS. 12C and D). lnc-PLAC1-1 silencing via GapmeR technology led to reduced miR-503 expression. In contrast, transfection of miR-503 precursors did not alter lnc-PLAC1-1 expression suggesting dependency of miR-503 expression on lnc-PLAC1-1 but not vice versa. Migratory capacity of lnc-PLAC1-1-deficient endothelial cells was additionally inhibited (FIG. 12E). The proliferative and migratory functional defects in endothelial cells after lnc-PLAC1-1 silencing were paralleled by a strong upregulation of cell cycle inhibitor p21 (FIG. 12F). Silencing of lnc-PLAC1-1 repressed expression of the key angiogenic factor GATA2 (FIG. 3G).

EXAMPLE 4

Enhanced Expression of Pro-Angiogenic lncRNAs Improves Migratory Capacity

To study the role of enhanced lncRNA expression in endothelial cells, hypoxia-sensitive lncRNAs lnc-DSCAM-1, isoform 3 (LINC00323-003) and lnc-PLAC1-1 were both overexpressed by generation of stable GFP-expressing endothelial cell lines (Ea.Hy926). The migration index is improved in transgenic Ea.Hy926 cells overexpressing LINC00323-003 and lnc-PLAC1-1 as compared to the control. Transgenic Ea.Hy926 constitutively overexpressing LINC00323-003 even revealed an significantly improved endothelial healing in the scratch wound assay presumably triggered by enhanced cyto-protective HMOX1 expression (FIG. 12H).

The invention claimed is:

1. An isolated nucleic acid comprising a nucleotide sequence at least 85% identical to one or more long non-coding RNAs (lncRNAs) selected from SEQ ID NOs 1, 2, and 3, wherein the nucleic acid is functionally coupled to a heart-specific promoter.

2. The nucleic acid of claim 1, wherein the nucleotide sequence is at least 90% identical to one or more long non-coding RNAs (lncRNAs) selected from SEQ ID NOs 1, 2, and 3.

3. The nucleic acid of claim 1, wherein the nucleotide sequence is at least 95% identical to one or more long non-coding RNAs (lncRNAs) selected from SEQ ID NOs 1, 2, and 3.

4. An expression vector comprising the nucleic acid of claim 1.

5. An isolated host cell comprising the expression vector of claim 4.

6. A pharmaceutical composition comprising the nucleic acid of claim 1.

7. The pharmaceutical composition of claim 6, wherein the nucleic acid is formulated as a vesicle.

8. A pharmaceutical composition comprising the expression vector of claim 4.

* * * * *